(12) United States Patent
Hope et al.

(10) Patent No.: US 9,139,554 B2
(45) Date of Patent: Sep. 22, 2015

(54) AMINO LIPIDS AND METHODS FOR THE DELIVERY OF NUCLEIC ACIDS

(75) Inventors: Michael J. Hope, Vancouver (CA); Sean C. Semple, Delta (CA); Jianxin Chen, Vancouver (CA); Thomas D. Madden, Vancouver (CA); Pieter R. Cullis, Vancouver (CA); Marco A. Ciufolini, Vancouver (CA); Barbara Low Shoud Mui, Vancouver (CA)

(73) Assignees: Tekmira Pharmaceuticals Corporation, Burnaby (CA); The University of British Columbia, Vancouver (CA)

(*) Notice: Subject to any disclaimer, the term of this patent is extended or adjusted under 35 U.S.C. 154(b) by 442 days.

(21) Appl. No.: 13/123,307

(22) PCT Filed: Oct. 9, 2009

(86) PCT No.: PCT/US2009/060251
§ 371 (c)(1),
(2), (4) Date: Jul. 1, 2011

(87) PCT Pub. No.: WO2010/042877
PCT Pub. Date: Apr. 15, 2010

(65) Prior Publication Data
US 2011/0256175 A1    Oct. 20, 2011

Related U.S. Application Data

(60) Provisional application No. 61/104,212, filed on Oct. 9, 2008, provisional application No. 61/104,219, filed on Oct. 9, 2008, provisional application No. 61/220,666, filed on Jun. 26, 2009.

(51) Int. Cl.
*C07D 317/28* (2006.01)
*A61K 9/127* (2006.01)
*C07D 319/06* (2006.01)

(52) U.S. Cl.
CPC ............ *C07D 317/28* (2013.01); *A61K 9/1271* (2013.01); *C07D 319/06* (2013.01)

(58) Field of Classification Search
CPC ... A61K 9/1271; C07D 319/06; C07D 317/28
USPC ............... 424/283.1, 450, 489; 544/152, 374; 549/373, 451
See application file for complete search history.

(56) References Cited

U.S. PATENT DOCUMENTS

| | | | |
|---|---|---|---|
| 3,687,808 A | 8/1972 | Merigan, Jr. et al. | |
| 3,993,754 A | 11/1976 | Rahman et al. | |
| 4,145,410 A | 3/1979 | Sears | |
| 4,224,179 A | 9/1980 | Schneider | |
| 4,235,871 A | 11/1980 | Papahadjopoulos et al. | |
| 4,394,448 A | 7/1983 | Szoka, Jr. et al. | |
| 4,438,052 A | 3/1984 | Weder et al. | |
| 4,469,863 A | 9/1984 | Ts'o et al. | |
| 4,476,301 A | 10/1984 | Imbach et al. | |
| 4,515,736 A | 5/1985 | Deamer | |
| 4,522,803 A | 6/1985 | Lenk et al. | |
| 4,588,578 A | 5/1986 | Fountain et al. | |
| 4,598,051 A | 7/1986 | Papahadjopoulos et al. | |
| 4,603,044 A | 7/1986 | Geho et al. | |
| 4,737,323 A | 4/1988 | Martin et al. | |
| 4,839,175 A * | 6/1989 | Guo et al. ..................... | 424/450 |
| 4,845,205 A | 7/1989 | Huynh Dinh et al. | |
| 4,897,355 A | 1/1990 | Eppstein et al. | |
| 4,957,773 A | 9/1990 | Spencer et al. | |
| 4,981,957 A | 1/1991 | Lebleu et al. | |
| 4,987,071 A | 1/1991 | Cech et al. | |
| 5,013,556 A | 5/1991 | Woodle et al. | |
| 5,023,243 A | 6/1991 | Tullis | |
| 5,034,506 A | 7/1991 | Summerton et al. | |
| 5,118,800 A | 6/1992 | Smith et al. | |
| 5,130,302 A | 7/1992 | Spielvogel et al. | |
| 5,134,066 A | 7/1992 | Rogers et al. | |
| 5,166,315 A | 11/1992 | Summerton et al. | |
| 5,171,678 A | 12/1992 | Behr et al. | |
| 5,175,273 A | 12/1992 | Bischofberger et al. | |

(Continued)

FOREIGN PATENT DOCUMENTS

| | | |
|---|---|---|
| EP | 0360257 | 11/1996 |
| EP | 0519463 | 10/1998 |

(Continued)

OTHER PUBLICATIONS

Wang G-W, Preparation, properties and applications of vesicle forming cleavable surfactants with a 1.3-Dioxane ring, J Colloid and Interface Science, 1995, 173, 49-54.*
Moss R, Relation of surfactant monomer structure to flip-flop dynamics in surface differentiated synthetic bilayer membranes, 1990, 112, 6391-6392.*
Gong and Lin, "A glassy carbon supported bilayer lipid-like membrane of 5,5- diteradecyl-2-(2-trimethyl-ammonioethyl)-1,3-dioxane bromide for electrochemical sensing of epinephrine," *Electrochimica Acta*, 49:4351-4357 (2004).
Wang et al., "Preparation, Properties, and Applications of Vesicle-Forming Cleavable Surfactants with a 1,3-Dioxane Ring," *Journal of Colloid and Interface Science*, 173:49-54 (1995).

(Continued)

*Primary Examiner* — Janet Epps-Smith
(74) *Attorney, Agent, or Firm* — Viksnins Harris & Padys PLLP

(57) ABSTRACT

The present invention provides superior compositions and methods for the delivery of therapeutic agents to cells. In particular, these include novel lipids and nucleic acid-lipid particles that provide efficient encapsulation of nucleic acids and efficient delivery of the encapsulated nucleic acid to cells in vivo. The compositions of the present invention are highly potent, thereby allowing effective knock-down of specific target proteins at relatively low doses. In addition, the compositions and methods of the present invention are less toxic and provide a greater therapeutic index compared to compositions and methods previously known in the art.

1 Claim, 9 Drawing Sheets

(56) References Cited

U.S. PATENT DOCUMENTS

| | | | |
|---|---|---|---|
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,208,036 A | 5/1993 | Eppstein et al. |
| 5,214,134 A | 5/1993 | Weis et al. |
| 5,216,141 A | 6/1993 | Benner |
| 5,225,212 A | 7/1993 | Martin et al. |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,264,618 A | 11/1993 | Felgner et al. |
| 5,276,019 A | 1/1994 | Cohen et al. |
| 5,278,302 A | 1/1994 | Caruthers et al. |
| 5,279,833 A | 1/1994 | Rose |
| 5,283,185 A | 2/1994 | Epand et al. |
| 5,286,634 A | 2/1994 | Stadler et al. |
| 5,286,717 A | 2/1994 | Cohen et al. |
| 5,319,080 A | 6/1994 | Leumann |
| 5,320,906 A | 6/1994 | Eley et al. |
| 5,321,131 A | 6/1994 | Agrawal et al. |
| 5,334,711 A | 8/1994 | Sproat et al. |
| 5,334,761 A | 8/1994 | Gebeyehu et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,532,130 A | 7/1996 | Alul |
| 5,534,499 A | 7/1996 | Ansell |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,412 A | 8/1996 | Eppstein et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,567,811 A | 10/1996 | Misiura et al. |
| 5,571,799 A | 11/1996 | Tkachuk et al. |
| 5,576,427 A | 11/1996 | Cook et al. |
| 5,578,475 A | 11/1996 | Jessee |
| 5,587,361 A | 12/1996 | Cook et al. |
| 5,587,469 A | 12/1996 | Cook et al. |
| 5,591,317 A | 1/1997 | Pitts, Jr. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,288 A | 3/1997 | Rubenstein |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,627,159 A | 5/1997 | Shih et al. |
| 5,631,359 A | 5/1997 | Chowrira et al. |
| 5,633,360 A | 5/1997 | Bischofberger et al. |
| 5,639,873 A | 6/1997 | Barascut et al. |
| 5,641,662 A | 6/1997 | Debs et al. |
| 5,646,265 A | 7/1997 | McGee |
| 5,656,743 A | 8/1997 | Busch et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,674,908 A | 10/1997 | Haces et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,703,055 A | 12/1997 | Felgner et al. |
| 5,705,385 A | 1/1998 | Bally et al. |
| 5,714,331 A | 2/1998 | Buchardt et al. |
| 5,718,709 A | 2/1998 | Considine et al. |
| 5,719,262 A | 2/1998 | Buchardt et al. |
| 5,736,392 A | 4/1998 | Hawley-Nelson et al. |
| 5,739,119 A | 4/1998 | Galli et al. |
| 5,747,470 A | 5/1998 | Becherer et al. |
| 5,753,613 A | 5/1998 | Ansell et al. |
| 5,759,829 A | 6/1998 | Shewmaker et al. |
| 5,783,683 A | 7/1998 | Morrison |
| 5,785,992 A | 7/1998 | Ansell et al. |
| 5,789,573 A | 8/1998 | Baker et al. |
| 5,801,154 A | 9/1998 | Baracchini et al. |
| 5,820,873 A | 10/1998 | Choi et al. |
| 5,877,220 A | 3/1999 | Schwartz et al. |
| 5,885,613 A | 3/1999 | Holland et al. |
| 5,958,901 A | 9/1999 | Dwyer et al. |
| 5,976,567 A | 11/1999 | Wheeler et al. |
| 5,981,501 A | 11/1999 | Wheeler et al. |
| 6,020,202 A | 2/2000 | Jessee |
| 6,020,526 A | 2/2000 | Schwartz et al. |
| 6,027,726 A | 2/2000 | Ansell |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,110,745 A | 8/2000 | Zhang et al. |
| 6,172,049 B1 | 1/2001 | Dwyer et al. |
| 6,235,310 B1 * | 5/2001 | Wang et al. .................. 424/450 |
| 6,251,939 B1 | 6/2001 | Schwartz et al. |
| 6,287,591 B1 | 9/2001 | Semple et al. |
| 6,320,017 B1 | 11/2001 | Ansell |
| 6,339,173 B1 | 1/2002 | Schwartz et al. |
| 6,376,248 B1 | 4/2002 | Hawley-Nelson et al. |
| 6,406,705 B1 | 6/2002 | Davis et al. |
| 6,543,484 B1 | 4/2003 | Highsmith |
| 6,586,410 B1 | 7/2003 | Wheeler et al. |
| 6,638,529 B2 | 10/2003 | Schwartz et al. |
| 6,649,780 B1 | 11/2003 | Eibl et al. |
| 6,670,393 B2 | 12/2003 | Schwartz et al. |
| 6,743,171 B1 | 6/2004 | Bowles et al. |
| 6,815,432 B2 | 11/2004 | Wheeler et al. |
| 6,835,395 B1 | 12/2004 | Semple et al. |
| 6,852,334 B1 | 2/2005 | Cullis et al. |
| 6,858,224 B2 | 2/2005 | Wheeler et al. |
| 6,858,225 B2 * | 2/2005 | Semple et al. ................ 424/450 |
| 7,094,423 B1 | 8/2006 | Maurer et al. |
| 7,166,745 B1 | 1/2007 | Chu et al. |
| 7,189,705 B2 | 3/2007 | Lam et al. |
| 7,223,887 B2 | 5/2007 | Gaucheron et al. |
| 7,341,738 B2 | 3/2008 | Semple et al. |
| 7,422,902 B1 | 9/2008 | Wheeler et al. |
| 7,479,573 B2 | 1/2009 | Chu et al. |
| 7,601,872 B2 | 10/2009 | Chu et al. |
| 7,687,070 B2 | 3/2010 | Gebeyehu et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,807,815 B2 | 10/2010 | MacLachlan et al. |

(56) References Cited

U.S. PATENT DOCUMENTS

| | | | |
|---|---|---|---|
| 7,901,708 | B2 | 3/2011 | MacLachlan et al. |
| 7,915,450 | B2 | 3/2011 | Chu et al. |
| 7,982,027 | B2 | 7/2011 | MacLachlan et al. |
| 8,034,376 | B2 | 10/2011 | Manoharan et al. |
| 8,058,068 | B2 | 11/2011 | Hawley-Nelson et al. |
| 8,058,069 | B2 * | 11/2011 | Yaworski et al. ............ 435/458 |
| 8,101,741 | B2 | 1/2012 | MacLachlan et al. |
| 8,158,827 | B2 | 4/2012 | Chu et al. |
| 2003/0069173 | A1 | 4/2003 | Hawley-Nelson et al. |
| 2003/0077829 | A1 | 4/2003 | MacLachlan |
| 2003/0125263 | A1 | 7/2003 | Gold et al. |
| 2003/0143732 | A1 | 7/2003 | Fosnaugh et al. |
| 2003/0229037 | A1 * | 12/2003 | Massing et al. ................ 514/44 |
| 2004/0063654 | A1 | 4/2004 | Davis et al. |
| 2004/0142025 | A1 | 7/2004 | MacLachlan et al. |
| 2004/0142892 | A1 | 7/2004 | Finn et al. |
| 2004/0253723 | A1 | 12/2004 | Tachas et al. |
| 2004/0259247 | A1 | 12/2004 | Tuschl et al. |
| 2005/0260757 | A1 | 11/2005 | Gebeyehu et al. |
| 2006/0051405 | A1 | 3/2006 | MacLachlan et al. |
| 2006/0083780 | A1 * | 4/2006 | Heyes et al. ................ 424/450 |
| 2006/0105976 | A1 | 5/2006 | Soutschek et al. |
| 2006/0134189 | A1 | 6/2006 | MacLachlan et al. |
| 2006/0147514 | A1 | 7/2006 | Gebeyehu et al. |
| 2006/0228406 | A1 | 10/2006 | Chiou et al. |
| 2007/0042031 | A1 | 2/2007 | MacLachlan et al. |
| 2007/0202598 | A1 | 8/2007 | Chu et al. |
| 2007/0202600 | A1 | 8/2007 | Chu et al. |
| 2009/0143583 | A1 | 6/2009 | Chu et al. |
| 2010/0159593 | A1 | 6/2010 | Chu et al. |
| 2011/0071208 | A1 | 3/2011 | MacLachlan et al. |
| 2011/0117125 | A1 | 5/2011 | Hope et al. |
| 2011/0195127 | A1 | 8/2011 | Lee et al. |
| 2012/0136073 | A1 | 5/2012 | Yang et al. |
| 2012/0238747 | A1 | 9/2012 | Chu et al. |

FOREIGN PATENT DOCUMENTS

| | | |
|---|---|---|
| WO | WO 91/03162 | 3/1991 |
| WO | WO 91/16024 | 10/1991 |
| WO | WO 92/07065 | 4/1992 |
| WO | WO 93/05162 | 3/1993 |
| WO | WO 93/12240 | 6/1993 |
| WO | WO 93/12756 | 7/1993 |
| WO | WO 93/15187 | 8/1993 |
| WO | WO 93/23569 | 11/1993 |
| WO | WO 93/24640 | 12/1993 |
| WO | WO 93/25673 | 12/1993 |
| WO | WO 94/02595 | 2/1994 |
| WO | WO 94/13688 | 6/1994 |
| WO | WO 95/02698 | 1/1995 |
| WO | WO 95/35301 | 12/1995 |
| WO | WO 96/02655 | 2/1996 |
| WO | WO 96/10390 | 4/1996 |
| WO | WO 96/11266 | 4/1996 |
| WO | WO 96/41873 | 12/1996 |
| WO | WO 01/05374 | 1/2001 |
| WO | WO 01/15726 | 3/2001 |
| WO | WO 02/34236 | 5/2002 |
| WO | WO 02/069369 | 9/2002 |
| WO | WO 02/087541 | 11/2002 |
| WO | WO 03/097805 | 11/2003 |
| WO | WO 2004/065546 | 8/2004 |
| WO | WO 2004/110499 | 12/2004 |
| WO | WO 2005/007196 | 1/2005 |
| WO | Wo 2005/026372 | 3/2005 |
| WO | WO 2005/120152 | 12/2005 |
| WO | WO 2005/121348 | 12/2005 |
| WO | WO 2006/074546 | 7/2006 |
| WO | WO 2006/138380 A2 | 12/2006 |
| WO | WO 2009/086558 | 7/2009 |
| WO | WO 2009/088891 | 7/2009 |
| WO | WO 2009/099942 | 8/2009 |
| WO | WO 2009/127060 | 10/2009 |
| WO | WO 2010/042877 | 4/2010 |
| WO | WO 2011/000106 | 1/2011 |
| WO | WO 2011/000107 | 1/2011 |
| WO | WO 2011/000108 | 1/2011 |
| WO | WO 2011/066651 | 6/2011 |
| WO | WO 2011/141703 | 11/2011 |
| WO | WO 2011/141704 | 11/2011 |
| WO | WO 2011/141705 | 11/2011 |
| WO | WO 2012/000104 | 1/2012 |

OTHER PUBLICATIONS

European Search Report for European Application No. EP2224912, mailed Dec. 2, 2011.
International Preliminary Report on Patentability for International Application No. PCT/US2008/088676, mailed Jul. 6, 2010.
International Search Report and Written Opinion for International Application No. PCT/US2008/088676, mailed Feb. 27, 2009.
International Preliminary Report on Patentability for International Application No. PCT/US2009/060251, mailed Apr. 12, 2011.
International Search Report and Written Opinion for International Application No. PCT/US2009/060251, mailed Dec. 3, 2009.
Abra, R. M. et al., "The Next Generation of Liposome Delivery Systems: Recent Experience with Tumor-Targeted, Sterically-Stabilized Immunoliposomes and Active-Loading Gradients," Journal of Liposome Research, 12(1&2):1-3 (2002).
Agrawal, S., "Antisense Oligonucleotides: Towards Clinical Trials," Trends in Biotechnology, 14:376-387 (1996).
Akinc, A. et. al., "A Combinatorial Library of Lipid-Like Materials for Delivery of RNAi Therapeutics," Nat. Biotechnol., 26(5):561-569 (2008).
Akinc, A. et al., "Development of Lipidoid-siRNA Formulations for Systemic Delivery to the Liver," Molecular Therapy, 17(5):872-879 (2009).
Allen, T. M. et al., "A New Strategy for Attachment of Antibodies to Sterically Stabilized Liposomes Resulting in Efficient Targeting to Cancer Cells," Biochimica et Biophysica Acta, 1237:99-108 (1995).
Arpicco, S. et al., "Preparation and Characterization af Novel Cationic Lipids Developed for Gene Transfection," Proceedings of the International Symposium on Controlled Release of Bioactive Materials, 26:759-760 (1999).
Arpicco, S. et al., "Synthesis, Characterization and Transfection Activity of New Saturated and Unsaturated Cationic Lipids," IL Farmaco, 59(11): 869-878 (2004).
Bailey, A. L. et al., "Modulation af Membrane Fusion by Asymmetric Transbilayer Distributions of Amino Lipids," Biochemistry, 33(42):12573-12580 (1994).
Ballas, N. et al., "Liposomes Bearing a Quartemary Ammonium Detergent as an Efficient Vehicle for Functional Transfer of TMV-RNA Into Plant Protoplasts," Biochimica et Biophysica Acta, 939:8-18 (1988).
Baringa, M., "Step Taken Toward Improved Vectors for Gene Transfer," Science, 266:1326 (1994).
Basha, G. et al., "influence of Cationic Lipid Composition on Gene Silencing Properties of Lipid Nanoparticle Formulations of siRNA in Antigen-Presenting Cells," Molecular Therapy, 19(12):2186-2200 (2011).
Baumann, W. J. et al. "Reactions of Aliphatic Methanesulfonates. I. Syntheses of Long-Chain Glyceryl-(I) Ethers," J. Org. Chem., 29:3055-3057 (1964).
Beale, G., et al. "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 11(7):449-456 (2003).
Behr, J-P, "Scientific Gene-Transfer Vectors," Acc. Chem. Res., 26(5):274-278 (1993).
Bennett, C. F. et al., "Cationic Lipids Enhance Cellular Uptake and Activity of Phosphorothioate Antisense Oligonucleotides," Molecular Pharmacology, 41:1023-1033 (1992).
Bligh, E. G. et al., "A Rapid Method of Total Lipid Extraction and Purification," Canadian Journal of Biochemistry and Physiology, 37(8).911-917 (1959).
Blume, G. et al., "Specific Targeting with Poly(ethylene glycol)-Modified Liposomes: Coupling of Homing Devices to the Ends of the

(56) References Cited

OTHER PUBLICATIONS

Polymeric Chains Combines Effective Target Binding with Long Circulation Times," Biochimica et Biophysica Acta, 1149:180-184 (1993).
Brigham, K. L. et al., "Rapid Communication: In vivo Transfection of Murine Lungs with a Functioning Prokaryotic Gene Using a Liposome Vehicle," The American Journal of the Medical Sciences, 298(4):278-281 (1989).
Brummelkamp, T. R. et al., "A System for Stable Expression of Short Interfering RNAs in Mammalian Cells," Science, 296:550-553 (2002).
Caplen, N. J. et al., "Specific inhibition of Gene Expression by Small Double-Stranded RNAs in Invertebrate and Vertebrate Systems," Proc. Natl. Acad. Sci. USA, 98(17).9742-9747 (2001).
Cech, T, R. et al,, "In Vitro Splicing of the Ribosomal RNA Precursor of Tetrahymena: Involvement of a Guanosine Nucleotide in the Excision of the Intervening Sequence," Cell, 27(3 Pt 2):487-496 (1981).
Cevc, G., "How Membrane Chain-Melting Phase-Transition Temperature is Affected by Lipid CHain Asymmetry and Degree of Unsaturation. An Effective Chain Length Model," Biochemestry, 30(29): 7186-7193 (1991).
Collins, R. A. et al., "Reaction Conditions and Kinetics of Self-Cleavage of a Ribozyme Derived from Neurospora VS RNA," Biochemistry, 32(11).2795-2799 (1993).
Cortesi, R. et al., "Effect of Cationic Liposome Composition on In Vitro Cytotoxicity and Protective Effect on Carried DNA," International Journal of Pharmaceutics, 139:69-78 (1996).
Crystal, R. G. "Transfer of Genes to Humans: Early Lessons and Obstacles to Success," Science, 270:404-410 (1995).
Cullis, P. R. et al., "The Polymorphic Phase Behaviour of Phosphatidylethanolamines of Natural and Synthetic Origin," Biochimica et Biophysica Acta, 513:31-42 (1978).
Cullis, P. R. et al., "Lipid Polymorphism and the Roles of Lipids in Membranes," Chemistry and Physics of Lipids, 40:127-144 (1986).
Semple, S. C. et al., "Interactions of Liposomes and Lipid-Based Carrier Systems with Blood Proteins: Relation to Clearance Behaviour In Vivo," Advanced Drug Delivery Reviews, 32:3-17 (1998).
Culver, K. W., "The First Human Gene Therapy Experiment," Chapter 4 in Gene Therapy: A Handbook for Physicians, Mary Ann Liebert, Inc. Publishers, pp. 33-40 (1994).
De Fougerolles, A. et al., "Interfering with Disease: A Progress Report on siRNA-Based Therapeutics," Nature Reviews, 6:443-453 (2007).
Defrees, S. A. et al., "Sialyl Lewis x Liposomes as a Multivalent Ligand and Inhibitor of E-Selectin Mediated Cellular Adhesion," Journal of the American Chemisty Society, 118:6101-6104 (1996).
Duzgunes, N., "Membrane Fusion," Chapter 5 in Subcellular Biochemistry, Roodyn, D. B. (Ed.), Plenum Press, New York and London, vol. 11, pp. 195-286 (1985).
Dwarki, V. J. et al., "Cationic Liposome-Mediated RNA Transfection," Methods in Enzymology, 217:644-654 (1993).
Elbashir, S. M. et al., "Duplexes of 21-Nucleotide RNAs Mediate RNA Interference in Cultured Mammalian Cells," Nature, 411:494-498 (2001).
Elbashir, S. M. et al., "Functional Anatomy of siRNAs for Mediating Efficient RNAi in Drosophila Melanogaster Embryo Lysate," The EMBO Journal, 20(23):6877-6888 (2001).
Enoch, H. G. et al., "Formation and Properties of 1000-Å-Diameter, Single-Bilayer Phospholipid Vesicles," Proc. Natl. Acad. Sci. USA, 76(1):145-149 (1979).
Epand, R. M. et al., "Dependence of the Bilayer to Hexagonal Phase Transition on Amphiphile Chain Length," Biochemistry, 28:9398-9402 (1989).
Felgner, P. L., "Nonviral Strategies for Gene Therapy," Scientific American, 276(6):102-106 (1997).
Felgner, P. L. et al., "Lipofection: A Highly Efficient, Lipid-Mediated DNA-Transfection Procedure," Proc. Natl. Acad. Sci. USA, 84:7413-7417 (1987).

Felgner, J. H. et al., "Enhanced Gene Delivery and Mechanism Studies with a Novel Series of Cationic Lipid Formulations," Journal of Biological Chemistry, 269(4):2550-2561 (1994).
Felgner, J. et al., "Cationic Lipid-Mediated Transfection in Mammalian Cells: 'Lipofection,'" J. Tiss. Cult. Meth., 15:63-68 (1993).
Felgner, P. L. et al., "Cationic Liposome Mediated Transfection," Proc. West. Pharmacol. Soc., 32:115-121 (1989).
Forster, A. C. et al., "Self-Cleavage of Plus and Minus RNAs of a Virusoid and a Structural Model for the Active Sites," Cell, 49(2):211-220 (1987).
Galbraith, W. M. et al., "Complement Activation and Hemodynamic Changes Following Intravenous Administration of Phosphorothioate Oligonucleotides in the Monkey," Antisense Research and Development, 4:201-206 (1994).
Gao, X. et al., "A Novel Cationic Liposome Reagent for Efficient Transfection of Mammalian Cells," Biochemical and Biophysical Research Communications, 179(1):280-285 (1991).
Gershon, H. et al., "Mode of Formation and Structural Feature of DNA-Cationic Liposome Complexes Used for Transfection," Biochemistry, 32(28):7143-7151 (1993).
Goodfellow, P. N., "Steady Steps Lead to the Gene," Nature, 341:102-103 (1989).
Griffiths-Jones, S. et al., "miRBase: microRNA Sequences, Targets and Gene Nomenclature," Nucleic Acids Research, Database Issue, 34:D140-D144 (2006).
Griffiths-Jones, S., "The microRNA Registry," Nucleic Acids Research, Database Issue, 32:D109-D111 (2004).
Guerrier-Takada, C. et al., "The RNA Moiety of Ribonuclease P Is the Catalytic Subunit of the Enzyme," Cell, 35(Part 2):849-857 (1983).
Guy-Caffey, J. K. et al., "Novel Polyaminolipids Enhance the Cellular Uptake of Oligonucleotides," The Journal of Biological Chemistry, 270(54:31391-31396 (1995).
Hafez, I. M. et al., "Roles of Lipid Polymorphism in Intracellular Delivery," Advanced Drug Delivery Reviews, 47:139-148 (2001).
Hafez, I. M. et al., "On the Mechanism Whereby Cationic Lipids Promote Intracellular Delivery of Polynucleic Acids," Gene Therapy, 8:1188-1196 (2001).
Hall, A. H. S. et al., "RNA interference Using Boranophosphate siRNAs: Structure-Activity Relationships," Nucleic Acids Research, 32(20):5991-6000 (2004).
Hampel, A. et al., "RNA Catalytic Properties of the Minimum (−)sTRSV Sequence," Biochemistry, 28(12):4929-4933 (1989).
Hampel, A. et al., "'Hairpin' Catalytic RNA Model: Evidence for Helices and Sequence Requirement for Substrate RNA," Nucleic Acids Research, 18(2):299-304 (1990).
Hawley-Nelson, P. et al., "LipofectAMINE™ Reagent: A New, Higher Efficiency Polycationic Liposome Transfection Reagent," Focus, 15(3)73-80(1993).
Heyes, J. A. et al., "Synthesis of Novel Cationic Lipids: Effect of Structural Modification on the Efficiency of Gene Transfer," Journal of Medicinal Chemistry, 45(1).99-114 (2002).
Heyes, J. et al., "Cationic Lipid Saturation Influences Intracellular Delivery of Encapsulated Nucleic Acids," Journal of Controlled Release, 107(2):276-287 (2005).
Heyes, J. et al., "Synthesis and Characterization of Novel Poly(ethylene glycol)-lipid Conjugates Suitable for Use in Drug Delivery," Journal of Controlled Release, 112:280-290 (2006).
Holen, T. et al., "Similar Behaviour of Single-Strand and Double-Strand siRNAs Suggests They Act Through a Common RNAi Pathway," Nucleic Acids Research, 31(9):2401-2407 (2003).
Hope, M. J. et al., "Production of Large Unilamellar Vesicles by a Rapid Extrusion Procedure. Characterization of Size Distribution, Trapped Volume and Ability to Maintain a Membrane Potential," Biochimica et Biophysica Acta, 812:55-65 (1985).
Hyde, S. C. et al., "Correction of the Ion Transport Defect in Cystic Fibrosis Transgenic Mice by Gene Therapy," Nature, 362:250-255 (1993).
Jaeger, D. A. et al., "Preparation and Characterization af Glycerol-Based Cleavable Surfactants and Derived Vesicles," Journal Am. Chem. Soc., 111(8):3001-3006 (1989).

(56) References Cited

OTHER PUBLICATIONS

Jaskulski, D. et al., "Inhibition of Cellular Proliferation by Antisense Oligodeoxynucleotides to PCNA Cyclin," Science, 240(4858):1544-1546 (1988).
Jeffs, L. B. et al., "A Scalable, Extrusion-Free Method for Efficient Liposomal Encapsulation af Plasmid DNA," Pharmaceutical Research, 22(3).362-372 (2005).
Jiang, L. et al., "Comparison of Protein Precipitation Methods for Sample Preparation Prior to Proteomic Analysis," Journal of Chromatography A, 1023(2):317-320 (2004).
John, M. et al., "Effective RNAi-Mediated Gene Silencing Without Interruption of the Endogenous MicroRNA Pathway," Nature, 449(7163):745-747 (2007).
Juliano, R. L. et al., "The Effect of Particle Size and Charge on the Clearance Rates of Liposomes and Liposome Encapsulated Drugs," Biochemical and Biophysical Research Communications, 63(3):651-658 (1975).
Keough, K. M. W., "influence of Chain Unsaturation and Chain Position on Thermotropism and Intermolecular Interactions in Membranes," Biochemical Society Transactions, 18(5):835-837 (1990).
Kim, S-H. et al., "Three-Dimensional Model of the Active Site of the Self-Splicing rRNA Precursor of Tetrahymena," Proc. Natl. Acad. Sci. USA, 84(24):8788-8792 (1987).
Kirpotin, D. et al., "Liposomes with Detachable Polymer Coating: Destabilization and Fusion of Dioleoylphosphatidylethanolamine Vesicles Triggered by Cleavage of Surface-Grafted Poly(ethylene glycol)," FEBS Letters, 388:115-118 (1996).
Klibanov, A. L. et al., "Long-Circulating Liposomes: Development and Perspectives," Journal of Liposome Research, 2(3).321-334 (1992).
Kunkel, L. M. et al., "Duchenne/Becker Muscular Dystrophy: A Short Overview of the Gene, the Protein, and Current Diagnostics," British Medical Bulletin, 45(3):630-643 (1989).
Kurreck, J., "Antisense technologies, Improvement through novel chemical modifications," Eur J Biochem., 270:1628-1644 (2003).
Lamberton, J. S. et al., "Varying the Nucleic Add Composition of siRNA Molecules Dramatically Varies the Duration and Degree of Gene Silencing," Molecular Biotechnology, 24:111-119 (2003).
Lee, J. B. et al., "Lipid Nanoparticle siRNA Systems for Silencing the Androgen Receptor in Human Prostate Cancer In Vivo," International Journal of Cancer, pp. 1-10 (2011).
Legendre, J-Y. et al., "Delivery of Plasmid DNA into Mammalian Cell Lines Using pH-Sensitive Liposomes: Comparison with Cationic Liposomes," Pharmaceutical Research, 9(10):1235-1242 (1992).
Leonetti, J-P. et al., "Antibody-Targeted Liposomes Containing Oligodeoxyribonucleotides Complementary to Viral RNA Selectively Inhibit Viral Replication," Proc. Natl. Acad. Sci. USA, 87;2448-2451 (1990).
Leventis, R. et al., "Interactions of Mammalian Cells with Lipid Dispersions Containing Novel Metabolizable Cationic Amphiphiles," Biochimica et Biophysica Acta, 1023:124-132 (1990).
Liu, D. et al., "Synthesis of Carbamate-Linked Lipids for Gene Delivery," Bioorganic & Medicinal Chemistry Letters, 15:3147-3150 (2005).
Manoharan, M., "RNA interference and chemically modified small interfering RNAs," Curr Opin Chem Biol., 8:570-579 (2004).
Mannino, R. J. et al., "Liposome Mediated Gene Transfer," Biotechniques, 6(7):682-690 (1988).
Marshall, E., "Gene Therapy's Growing Pains," Science, 269:1050-1055 (1995).
Martin, V. P., Helvetica Chimica Acta, 78:486-504 (1995).
Martin, B. et al., "The Design af Cationic Lipids for Gene Delivery," Current Pharmaceutical Design, 11,375-394 (2005).
Mashek, D. G. et al., "Short communication: net uptake of nonesterified long chain fatty acids by the perfused caudate lobe of the caprine liver," Journal of Dairy Science, 86(4):1218-1220 (2003).
Maurer, N. et al., "Spontaneous Entrapment of Polynucleotides upon Electrostatic Interaction with Ethanol-Destabilized Cationic Liposomes," Biophysical Journal, 80(5):2310-2326 (2001).
Michel, F, et al., "Modelling of the Three-Dimensional Architecture of Group I Catalytic Introns Based on Comparative Sequence Analysis," Journal of Molecular Biology, 216(3):585-610 (1990).
Moss, R. A. et al., "Relation of Surfactant Monomer Structure to Flip-Flop Dynamics in Surface-Differentiated Synthetic Bilayer Membranes," J. Am. Chem. Soc., 112:6391-6392 (1990).
Mui, B. et al., "Immune Stimulation by a CpG-Containing Oligodeoxynucleotide Is Enhanced When Encapsulated and Delivered in Lipid Particles," The Journal of Pharmacology and Experimental Therapeutics, 298(3):1185-1192 (2001).
Nicolau, C. et al., "Liposomes as Carriers of DNA," Crit. Rev. Ther. Drug Carrier Syst., 6(3):239-271 (1989).
Nielsen, P. E. et al., "Sequence-Selective Recognition of DNA by Strand Displacement with a Thymine-Substituted Polyamide," Science, 254:1497-1500 (1991).
Orkin, S, H. et al., "Report and Recommendations of the Panel to Assess the NIH Investment in Research on Gene Therapy," NIH Report (Dec. 7, 1995).
Paddison, P. J. et al., "Short Hairpin RNAs (shRNAs) Induce Sequence-Specific Silencing in Mammalian Cells," Genes & Development, 16(8):948-958 (2002).
Paddison, P. J. et al., "Stable Suppression of Gene Expression of RNAi in Mammalian Cells," Proc. Natl. Acad. Sci. USA, 99(3):1443-1448 (2002).
Paul, C. P. et al., "Effective Expression of Small Interfering RNA in Human Cells," Nature Biotechnology, 29:505-508 (2002).
Peris, J. et al., "Antisense Inhibition of Striatal $GABA_A$ Receptor Proteins Decreases GABA-Stimulated Chloride Uptake and Increases Cocaine Sensitivity in Rats," Molecular Brain Research, 57(2):310-320 (1998).
Been, M. D. et al., "Secondary Structure of the Self-Cleaving RNA of Hepatitis Delta Virus: Applications to Catalytic RNA Design," Biochemistry, 31(47):11843-11852 (1992).
Prakash, T. P. et al., "Positional Effect of Chemical Modifications on Short Interference RNA Activity in Mammalian Cells," J Med Chem., 48:4247-4253 (2005).
Puyal, C. et al., "A New Cationic Liposome Encapsulating Genetic Material: A Potential Delivery System for Polynucleotides," Eur. J. Biochem., 228:697-703 (1995).
Reinhold-Hurek, B. et al., "Self-Splicing Introns in tRNA Genes of Widely Divergent Bacteria," Nature, 357(6374):173-176 (1992).
Renneisen, K. et al., "Inhibition of Expression of Human Immunodeficiency Virus-1 in Vitro by Antibody Targeted Liposomes Containing Antisense RNA to the Env Region," The Journal of Biological Chemisty, 265(27):16337-16342 (1990).
Sapra, P. et al., "Ligand-Targeted Liposomal Anticancer Drugs," Progress in Lipid Research, 42(5):439-462 (2003).
Saville, B. J. et al., "A Site-Specific Self-Cleavage Reaction Performed by a Novel RNA in Neurospora Mitochondria," Cell, 61(4):685-696 (1990).
Saville, B. J. et al., "RNA-Mediated Ligation of Self-Cleavage Products of a Neurospora Mitochondriai Plasmid Transcript," Proc Natl Acad Sci USA, 88(19):8826-8830 (1991).
Semple, S. C. et al., "Lipid-Based Formulations of Antisense Oliganucleotides for Systemic Delivery Applications," Chapter 18 in Methods in Enzymology, Antisense Technology, Part A General Methods, Methods of Delivery, and RNA Studies, Phillips, M. I. (Ed.), vol. 313, pp. 322-341, Academic Press (2000).
Semple, S. C. et al., "Efficient Encapsulation of Antisense Oligonucleotides in Lipid Vesicles Using Ionizable Aminolipids: Formation of Novel Small Multilamellar Vesicle Structures," Biochimica et Biophysica Acta, 1510:152-166 (2001).
Semple, S. C. et al., "Rational Design of Cationic Lipids for siRNA Delivery," Nature Biotechnology, 28(2):172-176 (2010).
Spagnou, S. et al.; "Lipidic Carriers of siRNA: Differences in the Formulation, Cellular Uptake, and Delivery with Plasmid DNA," Biochemistry, 43(42):13348-13356 (2004).
Stamatatos, L. et al., "Interactions of Cationic Lipid Vesicles with Negatively Charged Phospholipid Vesicles and Biological Membranes," Biochemistry, 27(11):3917-3925 (1988).

(56) References Cited

OTHER PUBLICATIONS

Straubinger, R. M. et al., "Liposomes as Carriers for Intracellular Delivery of Nucelic Acids," Chapter 32 in Methods in Enzymology, Recombinant DNA, Part C, Wu, R. et al. (Eds.), vol. 101, pp. 512-527, Academic Press (1983).

Szoka, F. et al., "Comparative Properties and Methods of Preparation of Lipid Vesicles (Liposomes)," Ann. Rev. Biophys. Bioeng., 9:467-508 (1980).

Szoka, F. et al., "Procedure for Preparation of Liposomes With Large Internal Aqueous Space and High Capture by Reverse-Phase Evaporation," Proc. Natl. Acad. Sci. USA, 75(9):4194-4198 (1978).

Taylor, N. R. et al., "Chimeric DNA-RNA Hammerhead Ribozymes Have Enhanced In Vitro Catalytic Efficiency and Increased Stability In Vivo," Nucleic Acids Research, 20(17):4559-4565 (1992).

Uhlmann, E. et al., "Antisense: Chemical Modifications," In Encyclopedia of Cancer, vol. X, pp. 64-81, Academic Press Inc. (1997).

Van Der Woude, I. et al., "Parameters Influencing the Introduction of Plasmid DNA Into Cells by the Use of Synthetic Amphiphiles as a Carrier System," Biochimica et Biophysica Acta, 1240:34-40 (1995).

Vasanthakumar, G. et al., "Modulation of Drug Resistance in a Daunorubicin Resistant Subline with Oligonucleoside Methylphosphonates," Cancer Communications, 1(4):225-232 (1989).

Vigh, L. et al., "Does the membrane's physical state control the expression of heat shock and other genes?" TIBS, 23:369-374 (1998).

Vlassov, V. V. et al., "Transport of Oligonucleotides Across Natural and Model Membranes," Biochimica et Biophysics Acta, 1197;95-108 (1994).

Wilson, R. W. et al., "Counterion-Induced Condensation of Deoxyribonucleic Acid. A Light-Scattering Study," Biochemistry, 18(11):2192-2196 (1979).

Woodle, M. C. et al., "Versatility in Lipid Compositions Showing Prolonged Circulation with Sterically Stabilized Liposomes," Biochimica et Biophysica Acta, 1105:193-200 (1992).

Xu, Y. et al., "Mechanism of DNA Release from Cationic Liposome/DNA Complexes Used in Cell Transfection," Biochemistry, 35:5616-5623 (1996).

Yamamoto, S. et al., "Unique Palindromic Sequences in Synthetic Oligonucleotides are Required to Induce INF and Augment INF-Mediated Natural Killer Activity," The Journal of Immunology, 148:4072-4076 (1992).

Zalipsky, S., "Synthesis of an End-Group Emotionalized Polyethylene Glycol-Lipid Conjugate for Preparation of Polymer-Grafted Liposomes," Bioconjugate Chemistry, 4:296-299 (1993).

Zalipsky, S. et al., "Long Circulating, Cationic Liposomes Containing Amino-PEG-Phosphatidylethanolamine," FEBS Letters, 353:71-74 (1994).

Zelphati, O. et al., "Inhibition of HIV-1 Replication in Cultured Cells with Antisense Oligonucleotides Encapsulated in Immunoliposomes," Antisense Research and Development, 3:323-338 (1993).

Zelphati, O. et al., "Liposomes as a Carrier for Intracellular Delivery of Antisense Oligonucleotides: a Real or Magic Bullet?" Journal of Controlled Release, 41:99-119 (1996).

Zhang. H-Y. et al,, "RNA interference with Chemically. Modified siRNA," Current Topics in Medicinal Chemistry, 6:893-900 (2006).

Zhu, N. et al., "Systemic Gene Expression After Intravenous DNA Delivery into Adult Mice," Science, 261:209-211 (1993).

Zimmermann, T. S. et al., "RNAi-Mediated Gene Silencing in Non-Human Primates," Nature, 441:1-4 (2006).

\* cited by examiner

SEQUENCE LISTING

```
<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 1
tccatgacgt tcctgacgtt                                                   20

<210> SEQ ID NO 2
<211> LENGTH: 16
<212> TYPE: DNA
<213> ORGANISM: Artificial Sequence
<220> FEATURE:
<223> OTHER INFORMATION: Immunostimulatory oligonucleotide

<400> SEQUENCE: 2
taacgttgag gggcat                                                       16

<210> SEQ ID NO 3
<211> LENGTH: 16
<212> TYPE: DNA
<213> ORGANISM: Artificial Sequence
<220> FEATURE:
<223> OTHER INFORMATION: Immunostimulatory oligonucleotide

<400> SEQUENCE: 3
taagcatacg gggtgt                                                       16
```

```
<210> SEQ ID NO 4
<211> LENGTH: 16
<212> TYPE: DNA
<213> ORGANISM: Artificial Sequence
<220> FEATURE:
<223> OTHER INFORMATION: Immunostimulatory oligonucleotide
<220> FEATURE:
<221> NAME/KEY: modified_base
<222> LOCATION: 4
<223> OTHER INFORMATION: Methylated

<400> SEQUENCE: 4
taacgttgag gggcat                                                        16

<210> SEQ ID NO 5
<211> LENGTH: 6
<212> TYPE: DNA
<213> ORGANISM: Artificial Sequence
<220> FEATURE:
<223> OTHER INFORMATION: Immunostimulatory oligonucleotide

<400> SEQUENCE: 5 aacgtt                                                                    6

<210> SEQ ID NO 6
<211> LENGTH: 24
<212> TYPE: DNA
<213> ORGANISM: Artificial Sequence
<220> FEATURE:
<223> OTHER INFORMATION: Immunostimulatory oligonucleotide

<400> SEQUENCE: 6
gatgctgtgt cggggtctcc gggc                                               24

<210> SEQ ID NO 7
<211> LENGTH: 24
<212> TYPE: DNA
<213> ORGANISM: Artificial Sequence
<220> FEATURE:
<223> OTHER INFORMATION: Immunostimulatory oligonucleotide

<400> SEQUENCE: 7
tcgtcgtttt gtcgttttgt cgtt                                               24

<210> SEQ ID NO 8
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 8
tccaggactt ctctcaggtt                                                    20

<210> SEQ ID NO 9
<211> LENGTH: 18
<212> TYPE: DNA
<213> ORGANISM: Artificial Sequence
<220> FEATURE:
<223> OTHER INFORMATION: Immunostimulatory oligonucleotide

<400> SEQUENCE: 9
tctcccagcg tgcgccat                                                      18

<210> SEQ ID NO 10
```

```
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 10
tgcatccccc aggccaccat                                           20

<210> SEQ ID NO 11
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 11
gcccaagctg gcatccgtca                                           20

<210> SEQ ID NO 12
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 12
gcccaagctg gcatccgtca                                           20

<210> SEQ ID NO 13
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 13
ggtgctcact gcggc                                                15

<210> SEQ ID NO 14
<211> LENGTH: 16
<212> TYPE: DNA
<213> ORGANISM: Artificial Sequence
<220> FEATURE:
<223> OTHER INFORMATION: Immunostimulatory oligonucleotide

<400> SEQUENCE: 14
aaccgttgag gggcat                                               16

<210> SEQ ID NO 15
<211> LENGTH: 24
<212> TYPE: DNA
<213> ORGANISM: Artificial Sequence
<220> FEATURE:
<223> OTHER INFORMATION: Immunostimulatory oligonucleotide

<400> SEQUENCE: 15
tatgctgtgc cggggtcttc gggc                                      24

<210> SEQ ID NO 16
<211> LENGTH: 18
<212> TYPE: DNA
<213> ORGANISM: Artificial Sequence
<220> FEATURE:
<223> OTHER INFORMATION: Immunostimulatory oligonucleotide

<400> SEQUENCE: 16
```

```
gtgccggggt cttcgggc                                              18

<210> SEQ ID NO 17
<211> LENGTH: 18
<212> TYPE: DNA
<213> ORGANISM: Artificial Sequence
<220> FEATURE:
<223> OTHER INFORMATION: Immunostimulatory oligonucleotide

<400> SEQUENCE: 17
ggaccctcct ccggagcc                                              18

<210> SEQ ID NO 18
<211> LENGTH: 18
<212> TYPE: DNA
<213> ORGANISM: Artificial Sequence
<220> FEATURE:
<223> OTHER INFORMATION: Immunostimulatory oligonucleotide

<400> SEQUENCE: 18
tcctccggag ccagactt                                              18

<210> SEQ ID NO 19
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 19
aacgttgagg ggcat                                                 15

<210> SEQ ID NO 20
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 20
ccgtggtcat gctcc                                                 15

<210> SEQ ID NO 21
<211> LENGTH: 21
<212> TYPE: DNA
<213> ORGANISM: Artificial Sequence
<220> FEATURE:
<223> OTHER INFORMATION: Immunostimulatory oligonucleotide

<400> SEQUENCE: 21
cagcctggct caccgccttg g                                          21

<210> SEQ ID NO 22
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 22
cagccatggt tccccccaac                                            20

<210> SEQ ID NO 23
<211> LENGTH: 20
<212> TYPE: DNA
```

<213> ORGANISM: Artificial Sequence
<220> FEATURE:
<223> OTHER INFORMATION: Immunostimulatory oligonucleotide

<400> SEQUENCE: 23
gttctcgctg gtgagtttca                                              20

<210> SEQ ID NO 24
<211> LENGTH: 18
<212> TYPE: DNA
<213> ORGANISM: Artificial Sequence
<220> FEATURE:
<223> OTHER INFORMATION: Immunostimulatory oligonucleotide

<400> SEQUENCE: 24
tctcccagcg tgcgccat                                                18

<210> SEQ ID NO 25
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 25
gtgctccatt gatgc                                                   15

<210> SEQ ID NO 26
<211> LENGTH: 33
<212> TYPE: DNA
<213> ORGANISM: Artificial Sequence
<220> FEATURE:
<223> OTHER INFORMATION: Immunostimulatory oligonucleotide

<400> SEQUENCE: 26
gaguucugau gaggccgaaa ggccgaaagu cug                               33

<210> SEQ ID NO 27
<211> LENGTH: 6
<212> TYPE: DNA
<213> ORGANISM: Artificial Sequence
<220> FEATURE:
<223> OTHER INFORMATION: Immunostimulatory oligonucleotide

<400> SEQUENCE: 27 rrcgyy                                                              6

<210> SEQ ID NO 28
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 28
aacgttgagg ggcat                                                   15

<210> SEQ ID NO 29
<211> LENGTH: 16
<212> TYPE: DNA
<213> ORGANISM: Artificial Sequence
<220> FEATURE:
<223> OTHER INFORMATION: Immunostimulatory oligonucleotide

<400> SEQUENCE: 29
caacgttatg gggaga                                                  16

-continued

```
<210> SEQ ID NO 30
<211> LENGTH: 16
<212> TYPE: DNA
<213> ORGANISM: Artificial Sequence
<220> FEATURE:
<223> OTHER INFORMATION: Immunostimulatory oligonucleotide

<400> SEQUENCE: 30
taacgttgag gggcat                                                          16

<210> SEQ ID NO 31
<211> LENGTH: 20
<212> TYPE: DNA
<213> ORGANISM: Artificial Sequence
<220> FEATURE:
<223> OTHER INFORMATION: Immunostimulatory oligonucleotide
<220> FEATURE:
<221> NAME/KEY: modified_base
<222> LOCATION: 8, 17
<223> OTHER INFORMATION: Methylated

<400> SEQUENCE: 31
tccatgacgt tcctgacgtt                                                      20

<210> SEQ ID NO 32
<211> LENGTH: 24
<212> TYPE: DNA
<213> ORGANISM: Artificial Sequence
<220> FEATURE:
<223> OTHER INFORMATION: Immunostimulatory oligonucleotide
<220> FEATURE:
<221> NAME/KEY: modified_base
<222> LOCATION: 2, 5, 13, 21
<223> OTHER INFORMATION: Methylated

<400> SEQUENCE: 32
tcgtcgtttt gtcgttttgt cgtt                                                 24

<210> SEQ ID NO 33
<211> LENGTH: 21
<212> TYPE: DNA
<213> ORGANISM: Artificial Sequence
<220> FEATURE:
<223> OTHER INFORMATION: si-FVII sense olignucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: modified_base
<222> LOCATION: 4, 5, 7, 8, 9, 10, 14, 15, 16, 17, 19
<223> OTHER INFORMATION: 2'-F-modified nucleotide

<400> SEQUENCE: 33
ggaucaucuc aagucuuact t                                                    21

<210> SEQ ID NO 34
<211> LENGTH: 21
<212> TYPE: DNA
<213> ORGANISM: Artificial Sequence
<220> FEATURE:
<223> OTHER INFORMATION: si-FVII antisense oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: modified_base
<222> LOCATION: 2, 7, 8, 9, 14, 17, 18, 19
```

<223> OTHER INFORMATION: 2'-F-modified nucleotide

<400> SEQUENCE: 34
guaagacuug agaugaucct t                                              21

<210> SEQ ID NO 35
<211> LENGTH: 21
<212> TYPE: DNA
<213> ORGANISM: Artificial Sequence
<220> FEATURE:
<223> OTHER INFORMATION: si-Luc sense oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: modified_base
<222> LOCATION: 1, 2, 3, 5, 7, 8, 12, 14, 15, 16, 17
<223> OTHER INFORMATION: 2'-O-Me-modified nucleotide

<400> SEQUENCE: 35
cuuacgcuga guacuucgat t                                              21

<210> SEQ ID NO 36
<211> LENGTH: 21
<212> TYPE: DNA
<213> ORGANISM: Artificial Sequence
<220> FEATURE:
<223> OTHER INFORMATION: si-Luc antisense oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: modified_base
<222> LOCATION: 7, 11, 16
<223> OTHER INFORMATION: 2-O-Me-modified nucleotide

<400> SEQUENCE: 36
ucgaaguacu cagcguaagt t                                              21

<210> SEQ ID NO 37
<211> LENGTH: 21
<212> TYPE: DNA
<213> ORGANISM: Artificial Sequence
<220> FEATURE:
<223> OTHER INFORMATION: siTTR sense oligonucleotide
<220> FEATURE:
<221> NAME/KEY: misc_RNA
<222> LOCATION: (1)...(19)
<223> OTHER INFORMATION: siRNA
<220> FEATURE:
<221> NAME/KEY: modified_base
<222> LOCATION: 2, 5, 6, 12, 14, 15, 16, 17, 19
<223> OTHER INFORMATION: 2'-O-Me-modified nucleotides

<400> SEQUENCE: 37
guaaccaaga guauuccaut t                                              21

<210> SEQ ID NO 38
<211> LENGTH: 21
<212> TYPE: DNA
<213> ORGANISM: Artificial Sequence
<220> FEATURE:
<223> OTHER INFORMATION: siTTR antisense oligonucleotide
<220> FEATURE:
<221> NAME/KEY: misc_RNA -continued
```
<222> LOCATION: (1)...(19)
<223> OTHER INFORMATION: siRNA
<220> FEATURE:
<221> NAME/KEY: modified_base
<222> LOCATION: 7, 17
<223> OTHER INFORMATION: 2'-O-Me-Modified nucleotides
<400> SEQUENCE: 38
auggaauacu cuugguuact t                                              21
```

AMINO LIPIDS AND METHODS FOR THE DELIVERY OF NUCLEIC ACIDS

CROSS-REFERENCE(S) TO RELATED APPLICATION(S)

This application claims the benefit under 35 U.S.C. §119 (e) of U.S. Provisional Patent Application No. 61/104,219 filed Oct. 9, 2008; U.S. Provisional Patent Application No. 61/104,212 filed Oct. 9, 2008; and U.S. Provisional Patent Application No. 61/220,666 filed Jun. 26, 2009, where these (three) provisional applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480208_461PC—SEQUENCE_LISTING.txt. The text file is 9 KB, was created on Oct. 9, 2009, and is being submitted electronically via EFS-Web.

BACKGROUND

1. Technical Field

The present invention relates to the field of therapeutic agent delivery using lipid particles. In particular, the present invention provides cationic lipids and lipid particles comprising these lipids, which are advantageous for the in vivo delivery of nucleic acids, as well as nucleic acid-lipid particle compositions suitable for in vivo therapeutic use. Additionally, the present invention provides methods of making these compositions, as well as methods of introducing nucleic acids into cells using these compositions, e.g., for the treatment of various disease conditions.

2. Description of the Related Art

Therapeutic nucleic acids include, e.g., small interfering RNA (siRNA), micro RNA (miRNA), antisense oligonucleotides, ribozymes, plasmids, and immune stimulating nucleic acids. These nucleic acids act via a variety of mechanisms. In the case of siRNA or miRNA, these nucleic acids can down-regulate intracellular levels of specific proteins through a process termed RNA interference (RNAi). Following introduction of siRNA or miRNA into the cell cytoplasm, these double-stranded RNA constructs can bind to a protein termed RISC. The sense strand of the siRNA or miRNA is displaced from the RISC complex providing a template within RISC that can recognize and bind mRNA with a complementary sequence to that of the bound siRNA or miRNA. Having bound the complementary mRNA the RISC complex cleaves the mRNA and releases the cleaved strands. RNAi can provide down-regulation of specific proteins by targeting specific destruction of the corresponding mRNA that encodes for protein synthesis.

The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by siRNA or miRNA constructs are, first, their susceptibility to nuclease digestion in plasma and, second, their limited ability to gain access to the intracellular compartment where they can bind RISC when administered systemically as the free siRNA or miRNA. These double-stranded constructs can be stabilized by incorporation of chemically modified nucleotide linkers within the molecule, for example, phosphothioate groups. However, these chemical modifications provide only limited protection from nuclease digestion and may decrease the activity of the construct. Intracellular delivery of siRNA or miRNA can be facilitated by use of carrier systems such as polymers, cationic liposomes or by chemical modification of the construct, for example by the covalent attachment of cholesterol molecules [reference]. However, improved delivery systems are required to increase the potency of siRNA and miRNA molecules and reduce or eliminate the requirement for chemical modification.

Antisense oligonucleotides and ribozymes can also inhibit mRNA translation into protein. In the case of antisense constructs, these single stranded deoxynucleic acids have a complementary sequence to that of the target protein mRNA and can bind to the mRNA by Watson-Crick base pairing. This binding either prevents translation of the target mRNA and/or triggers RNase H degradation of the mRNA transcripts. Consequently, antisense oligonucleotides have tremendous potential for specificity of action (i.e., down-regulation of a specific disease-related protein). To date, these compounds have shown promise in several in vitro and in vivo models, including models of inflammatory disease, cancer, and HIV (reviewed in Agrawal, *Trends in Biotech.* 14:376-387 (1996)). Antisense can also affect cellular activity by hybridizing specifically with chromosomal DNA. Advanced human clinical assessments of several antisense drugs are currently underway. Targets for these drugs include the bcl2 and apolipoprotein B genes and mRNA products.

Immune-stimulating nucleic acids include deoxyribonucleic acids and ribonucleic acids. In the case of deoxyribonucleic acids, certain sequences or motifs have been shown to illicit immune stimulation in mammals. These sequences or motifs include the CpG motif, pyrimidine-rich sequences and palindromic sequences. It is believed that the CpG motif in deoxyribonucleic acids is specifically recognized by an endosomal receptor, toll-like receptor 9 (TLR-9), which then triggers both the innate and acquired immune stimulation pathway. Certain immune stimulating ribonucleic acid sequences have also been reported. It is believed that these RNA sequences trigger immune activation by binding to toll-like receptors 6 and 7 (TLR-6 and TLR-7). In addition, double-stranded RNA is also reported to be immune stimulating and is believe to activate via binding to TLR-3.

One well known problem with the use of therapeutic nucleic acids relates to the stability of the phosphodiester internucleotide linkage and the susceptibility of this linker to nucleases. The presence of exonucleases and endonucleases in serum results in the rapid digestion of nucleic acids possessing phosphodiester linkers and, hence, therapeutic nucleic acids can have very short half-lives in the presence of serum or within cells. (Zelphati, O., et al., *Antisense. Res. Dev.* 3:323-338 (1993); and Thierry, A. R., et al., pp 147-161 in Gene Regulation: Biology of Antisense RNA and DNA (Eds. Erickson, R P and Izant, J G; Raven Press, NY (1992)). Therapeutic nucleic acid being currently being developed do not employ the basic phosphodiester chemistry found in natural nucleic acids, because of these and other known problems.

This problem has been partially overcome by chemical modifications that reduce serum or intracellular degradation. Modifications have been tested at the internucleotide phosphodiester bridge (e.g., using phosphorothioate, methylphosphonate or phosphoramidate linkages), at the nucleotide base (e.g., 5-propynyl-pyrimidines), or at the sugar (e.g., 2'-modified sugars) (Uhlmann E., et al. Antisense: Chemical Modifications. Encyclopedia of Cancer, Vol. X., pp 64-81 Academic Press Inc. (1997)). Others have attempted to improve stability using 2'-5' sugar linkages (see, e.g., U.S. Pat. No. 5,532,130). Other changes have been attempted. However, none of these solutions have proven entirely satisfactory, and in vivo free therapeutic nucleic acids still have only limited efficacy.

In addition, as noted above relating to siRNA and miRNA, problems remain with the limited ability of therapeutic nucleic acids to cross cellular membranes (see, Vlassov, et al., *Biochim. Biophys. Acta* 1197:95-1082 (1994)) and in the problems associated with systemic toxicity, such as complement-mediated anaphylaxis, altered coagulatory properties, and cytopenia (Galbraith, et al., *Antisense Nucl. Acid Drug Des.* 4:201-206 (1994)).

To attempt to improve efficacy, investigators have also employed lipid-based carrier systems to deliver chemically modified or unmodified therapeutic nucleic acids. In Zelphati, O. and Szoka, F. C., *J. Contr. Rel.* 41:99-119 (1996), the authors refer to the use of anionic (conventional) liposomes, pH sensitive liposomes, immunoliposomes, fusogenic liposomes, and cationic lipid/antisense aggregates. Similarly siRNA has been administered systemically in cationic liposomes, and these nucleic acid-lipid particles have been reported to provide improved down-regulation of target proteins in mammals including non-human primates (Zimmermann et al., *Nature* 441: 111-114 (2006)).

In spite of this progress, there remains a need in the art for improved nucleic acid-lipid particles and compositions that are suitable for general therapeutic use. Preferably, these compositions would encapsulate nucleic acids with high-efficiency, have high drug:lipid ratios, protect the encapsulated nucleic acid from degradation and clearance in serum, be suitable for systemic delivery, and provide intracellular delivery of the encapsulated nucleic acid. In addition, these nucleic acid-lipid particles should be well-tolerated and provide an adequate therapeutic index, such that patient treatment at an effective dose of the nucleic acid is not associated with significant toxicity and/or risk to the patient. The present invention provides such compositions, methods of making the compositions, and methods of using the compositions to introduce nucleic acids into cells, including for the treatment of diseases.

BRIEF SUMMARY

The present invention provides novel amino lipids, as well as lipid particles comprising the same. These lipid particles may further comprise an active agent and be used according to related methods of the invention to deliver the active agent to a cell.

In one embodiment, the present invention includes an amino lipid having the following structure (I):

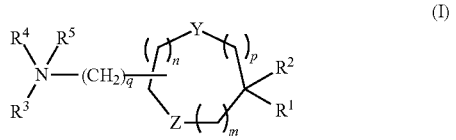

(I)

or salts thereof, wherein $R^1$ and $R^2$ are either the same or different and independently optionally substituted $C_{12}$-$C_{24}$ alkyl, optionally substituted $C_{12}$-$C_{24}$ alkenyl, optionally substituted $C_{12}$-$C_{24}$ alkynyl, or optionally substituted $C_{12}$-$C_{24}$ acyl;

$R^3$ and $R^4$ are either the same or different and independently optionally substituted $C_1$-$C_6$ alkyl, optionally substituted $C_1$-$C_6$ alkenyl, or optionally substituted $C_1$-$C_6$ alkynyl or $R^3$ and $R^4$ may join to form an optionally substituted heterocyclic ring of 4 to 6 carbon atoms and 1 or 2 heteroatoms chosen from nitrogen and oxygen;

$R^5$ is either absent or hydrogen or $C_1$-$C_6$ alkyl to provide a quaternary amine;

m, n, and p are either the same or different and independently either 0 or 1 with the proviso that m, n, and p are not simultaneously 0;

q is 2, 3, or 4; and

Y and Z are either the same or different and independently O, S, or NH.

In one embodiment, the amino lipid is the amino lipid having structure (I) wherein q is 2.

In certain embodiments, the amino lipid has the following structure (II):

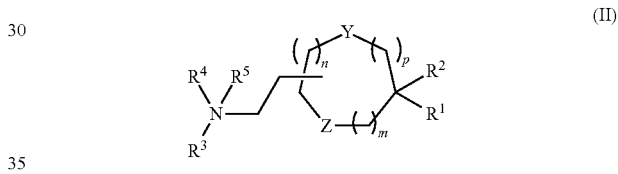

(II)

or salts thereof, wherein $R^1$ and $R^2$ are either the same or different and independently optionally substituted $C_{12}$-$C_{24}$ alkyl, optionally substituted $C_{12}$-$C_{24}$ alkenyl, optionally substituted $C_{12}$-$C_{24}$ alkynyl, or optionally substituted $C_{12}$-$C_{24}$ acyl;

$R^3$ and $R^4$ are either the same or different and independently optionally substituted $C_1$-$C_6$ alkyl, optionally substituted $C_1$-$C_6$ alkenyl, or optionally substituted $C_1$-$C_6$ alkynyl or $R^3$ and $R^4$ may join to form an optionally substituted heterocyclic ring of 4 to 6 carbon atoms and 1 or 2 heteroatoms chosen from nitrogen and oxygen;

$R^5$ is either absent or is hydrogen or $C_1$-$C_6$ alkyl to provide a quaternary amine;

m, n, and p are either the same or different and independently either 0 or 1 with the proviso that m, n, and p are not simultaneously 0;

Y and Z are either the same or different and independently O, S, or NH.

In particular embodiments, the amino lipid has the following structure (III):

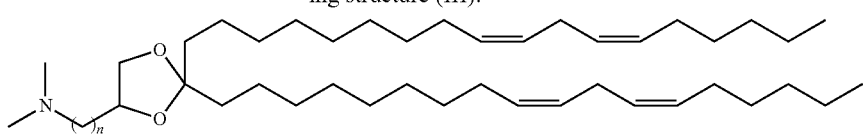

wherein n is 2, 3, or 4.

In one particular embodiment, the amino lipid has the structure:

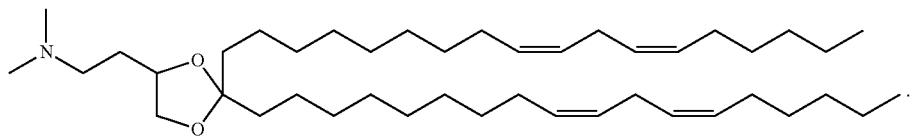

DLin-K-C2-DMA

In one particular embodiment, the amino lipid has the structure:

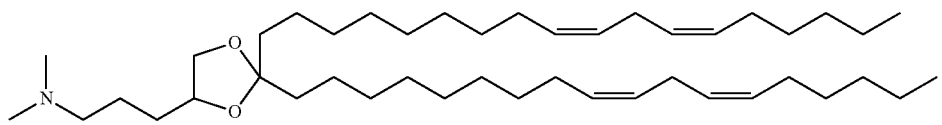

DLin-K-C3-DMA

In one particular embodiment, the amino lipid has the structure:

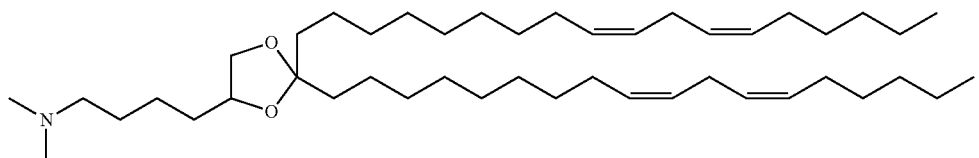

DLin-K-C4-DMA

In another embodiment, the present invention provides an amino lipid having the structure:

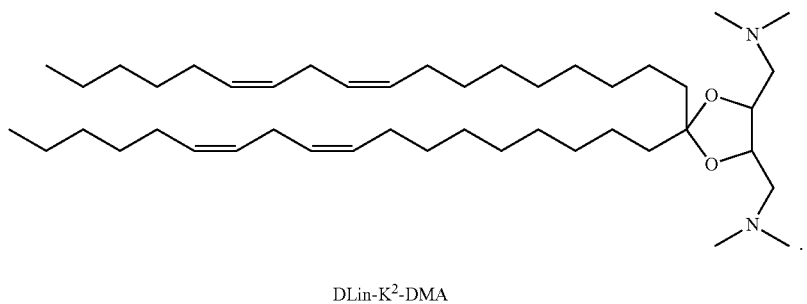 [SMILES: CCCCC/C=C\C/C=C\CCCCCCCCC1(CCCCCCCC/C=C\C/C=C\CCCCC)OC(CN(C)C)C(CN(C)C)O1]

DLin-K$^2$-DMA

In further related embodiments, the present invention includes a lipid particle comprising one or more of the above amino lipids of the present invention. In certain embodiments, the particle further comprises a neutral lipid and a lipid capable of reducing particle aggregation. In one particular embodiment, the lipid particle consists essentially of: (i) DLin-K-C2-DMA; (ii) a neutral lipid selected from DSPC, POPC, DOPE, and SM; (iii) cholesterol; and (iv) PEG-S-DMG, PEG-C-DOMG or PEG-DMA, in a molar ratio of about 20-60% DLin-K-C2-DMA:5-25% neutral lipid:25-55% Chol:0.5-15% PEG-S-DMG, PEG-C-DOMG or PEG-DMA. In one particular embodiment, the lipid particle consists essentially of: (i) DLin-K$^2$-DMA; (ii) a neutral lipid selected from DSPC, POPC, DOPE, and SM; (iii) cholesterol; and (iv) PEG-S-DMG, PEG-C-DOMG or PEG-DMA, in a molar ratio of about 20-60% DLin-K$^2$-DMA:5-25% neutral lipid:25-55% Chol:0.5-15% PEG-S-DMG, PEG-C-DOMG or PEG-DMA.

In additional related embodiments, the present invention includes lipid particles of the invention that further comprise a therapeutic agent. In one embodiment, the therapeutic agent is a nucleic acid. In various embodiments, the nucleic acid is a plasmid, an immunostimulatory oligonucleotide, a siRNA, a microRNA, an antisense oligonucleotide, or a ribozyme.

In yet another related embodiment, the present invention includes a pharmaceutical composition comprising a lipid particle of the present invention and a pharmaceutically acceptable excipient, carrier, or diluent.

The present invention further includes, in other related embodiments, a method of modulating the expression of a polypeptide by a cell, comprising providing to a cell a lipid particle or pharmaceutical composition of the present invention. In particular embodiments, the lipid particle comprises a therapeutic agent selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof, such that the expression of the polypeptide is reduced. In another embodiment, the nucleic acid is a plasmid that encodes the polypeptide or a functional variant or fragment thereof, such that expression of the polypeptide or the functional variant or fragment thereof is increased.

In yet a further related embodiment, the present invention includes a method of treating a disease or disorder characterized by overexpression of a polypeptide in a subject, comprising providing to the subject a lipid particle or pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In another related embodiment, the present invention includes a method of treating a disease or disorder characterized by underexpression of a polypeptide in a subject, comprising providing to the subject the pharmaceutical composition of the present invention, wherein the therapeutic agent is a plasmid that encodes the polypeptide or a functional variant or fragment thereof.

In a further embodiment, the present invention includes a method of inducing an immune response in a subject, comprising providing to the subject the pharmaceutical composition of the present invention, wherein the therapeutic agent is an immunostimulatory oligonucleotide. In particular embodiments, the pharmaceutical composition is provided to the patient in combination with a vaccine or antigen.

In a related embodiment, the present invention includes a vaccine comprising the lipid particle of the present invention and an antigen associated with a disease or pathogen. In one embodiment, the lipid particle comprises an immunostimulatory nucleic acid or oligonucleotide. In a particular embodiment, the antigen is a tumor antigen. In another embodiment, the antigen is a viral antigen, a bacterial antigen, or a parasitic antigen.

The present invention further includes methods of preparing the lipid particles and pharmaceutical compositions of the present invention, as well as kits useful in the preparation of these lipid particle and pharmaceutical compositions.

In particle embodiments, any of the compositions or methods of the present invention may comprise any of the other cationic lipids of the present invention, as described herein, as the cationic lipid. In particular embodiments, the cationic lipid is DLin-$K^2$-DMA or DLin-K6-DMA.

BRIEF DESCRIPTION OF THE SEVERAL VIEWS OF THE DRAWINGS

FIG. 2A depicts the silencing activity of DLinDAP (▼), DLinDMA (▲), DLin-K-DMA (■) and DLin-K-C2-DMA (●) formulations in the mouse FVII model. All nucleic acid-lipid particles were prepared using the preformed vesicle (PFV) method and were composed of ionizable cationic lipid, DSPC, cholesterol and PEG-lipid (40/10/40/10 mol/mol) with a FVII siRNA-to-total lipid ratio of ~0.05 (wt/wt). Data points are expressed as a percentage of PBS control animals and represent group mean (n=5)±s.d, and all formulations were compared within the same study. FIG. 2B demonstrates the influence of headgroup extensions on the activity of DLin-K-DMA. DLin-K-DMA (■) had additional methylene groups added between the DMA headgroup and the ketal ring linker to generate DLin-K-C2-DMA (●), DLin-K-C3-DMA (▲) and DLin-K-C4-DMA (▼). The activity of PFV formulations of each lipid was assessed in the mouse FVII model. Data points are expressed as a percentage of PBS control animals and represent group mean (n=4)±s.d.

FIG. 9A is a graph showing the improved efficacy of KC2-SNALP versus a DLin-K-C2-DMA PFV formulation in mice. The in vivo efficacy of KC2-SNALP (○) was compared to that of the un-optimized DLin-KC2-DMA PFV formulation (●) in the mouse FVII model. Data points are expressed as a percentage of PBS control animals and represent group mean (n=5)±s.d. FIG. 9B depicts the efficacy of KC2-SNALP in non-human primates. Cynomolgus monkeys (n=3 per group) received either 0.03, 0.1, 0.3 or 1 mg/kg siTTR, or 1 mg/kg siApoB formulated in KC2-SNALP or PBS as 15 minute intravenous infusions (5 mL/kg) via the cephalic vein. Animals were sacrificed at 48 hours post-administration. TTR mRNA levels relative to GAPDH mRNA levels were determined in liver samples. Data points represent group mean±s.d. *=P<0.05; **=P<0.005.

DETAILED DESCRIPTION

Figure 1:
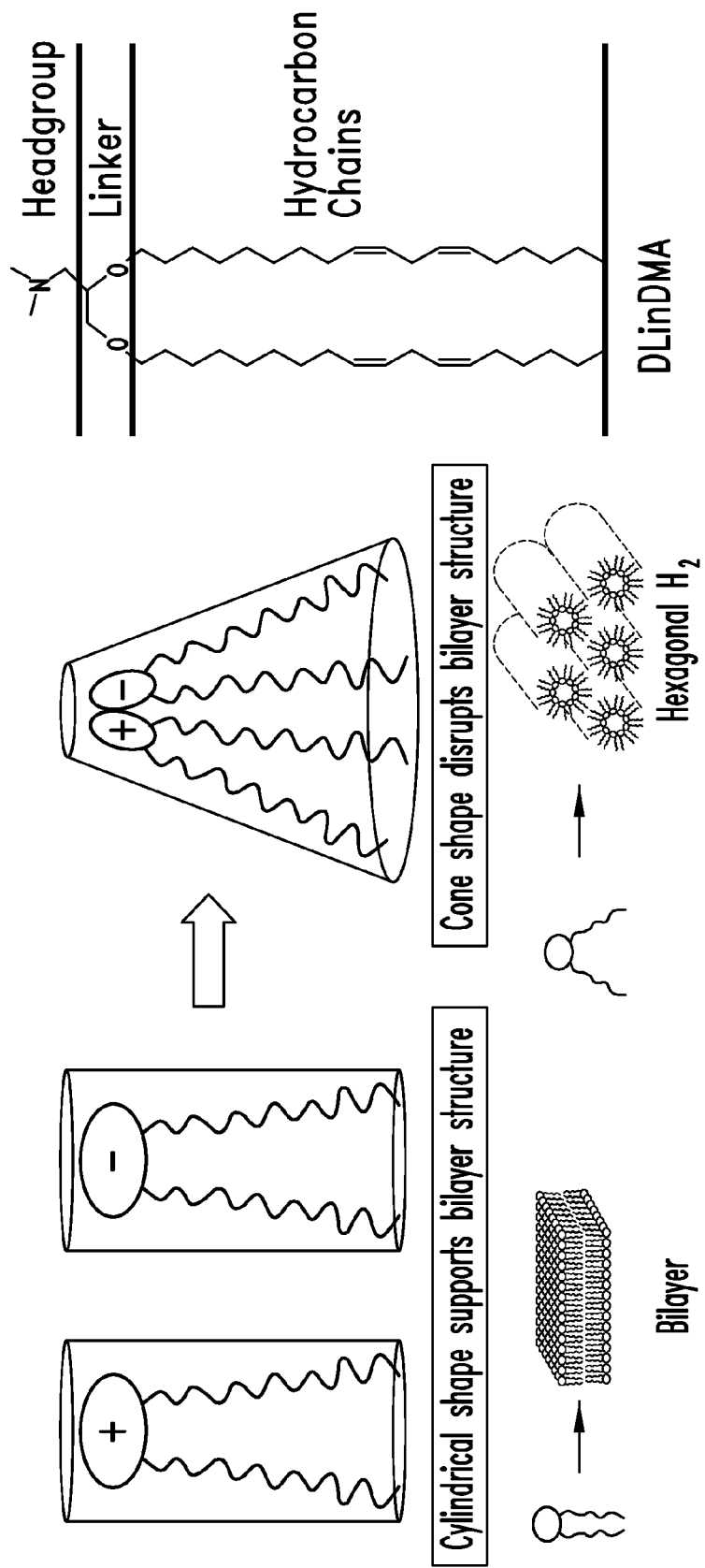
FIG. 1 is a diagram of a proposed mechanism of action for the membrane disruptive effects of cationic lipids and a structural diagram of DLinDMA divided into headgroup, linker and hydrocarbon chain domains. In isolation, cationic lipids and endosomal membrane anionic lipids such as phosphatidylserine adopt a cylindrical molecular shape, which is compatible with packing in a bilayer configuration. However, when cationic and anionic lipids are mixed together, they combine to form an ion pairs where the cross-sectional area of the combined headgroup is less than that of the sum of individual headgroup areas in isolation. The ion pair therefore adopts a molecular "cone" shape, which promotes the formation of inverted, non-bilayer phases such as the hexagonal $H_{II}$ phase illustrated. Inverted phases do not support bilayer structure and are associated with membrane fusion and membrane disruption (Hafez, I. M., et al., *Gene Ther* 8, 1188-1196 (2001) and Cullis, P. R., et al., *Chem Phys Lipids* 40, 127-144 (1986)).

The present invention is based, in part, upon the identification of novel cationic lipids that provide superior results when used in lipid particles for the in vivo delivery of a therapeutic agent. In particular, the present invention provides nucleic acid-lipid particle compositions (also referred to as formulations or liposomal formulations) comprising a cationic lipid according to the present invention that provide increased activity of the nucleic acid and significant tolerability of the compositions in vivo, which is expected to correlate with a significant increase in therapeutic index as compared to nucleic acid-lipid particle compositions previously described.

As described in the accompanying Examples, a rational design approach was employed for the discovery of novel lipids for use in next-generation lipid particle systems to deliver nucleic acids, including, e.g., RNAi therapeutics. Using this approach, important structure-activity considerations for ionizable cationic lipids were described, and multiple lipids based on the DLinDMA structure were designed and characterized. Nucleic acid-lipid particles comprising the cationic lipid termed DLin-K-C2-DMA were shown to be well-tolerated in both rodent and non-human primates and exhibited in vivo activity at siRNA doses as low as 0.01 mg/kg in rodents, as well as silencing of a therapeutically significant gene (TTR) in non-human primates. Notably, the TTR silencing achieved in this work ($ED_{50}$~0.3 mg/kg), represents a significant improvement in activity relative to previous reports of LNP-siRNA mediated silencing in non-human primates. The efficacy observed in this study is believed to represent the highest level of potency observed for an RNAi therapeutic in non-human primates to date.

Accordingly, in certain embodiments, the present invention specifically provides for improved compositions for the delivery of siRNA molecules. It is shown herein that these compositions are effective in down-regulating the protein levels and/or mRNA levels of target proteins. The lipid particles and compositions of the present invention may be used for a variety of purposes, including the delivery of associated or encapsulated therapeutic agents to cells, both in vitro or in vivo. Accordingly, the present invention provides methods of treating diseases or disorders in a subject in need thereof, by contacting the subject with a lipid particle of the present invention associated with a suitable therapeutic agent.

As described herein, the lipid particles of the present invention are particularly useful for the delivery of nucleic acids, including, e.g., siRNA molecules and plasmids. Therefore, the lipid particles and compositions of the present invention may be used to modulate the expression of target genes and proteins both in vitro and in vivo by contacting cells with a lipid particle of the present invention associated with a nucleic acid that reduces target gene expression (e.g., an siRNA) or a nucleic acid that may be used to increase expression of a desired protein (e.g., a plasmid encoding the desired protein).

Various exemplary embodiments of the cationic lipids of the present invention, as well as lipid particles and compositions comprising the same, and their use to deliver therapeutic agents and modulate gene and protein expression are described in further detail below.

A. Amino Lipids

The present invention provides novel amino lipids that are advantageously used in lipid particles of the present invention for the in vivo delivery of therapeutic agents to cells, including amino lipids having the following structures.

In one embodiment of the invention, the amino lipid has the following structure (I):

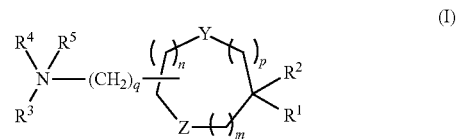

wherein $R^1$ and $R^2$ are either the same or different and independently optionally substituted $C_{12}$-$C_{24}$ alkyl, optionally substituted $C_{12}$-$C_{24}$ alkenyl, optionally substituted $C_{12}$-$C_{24}$ alkynyl, or optionally substituted $C_{12}$-$C_{24}$ acyl;

$R^3$ and $R^4$ are either the same or different and independently optionally substituted $C_1$-$C_6$ alkyl, optionally substituted $C_1$-$C_6$ alkenyl, or optionally substituted $C_1$-$C_6$ alkynyl or $R^3$ and $R^4$ may join to form an optionally substituted heterocyclic ring of 4 to 6 carbon atoms and 1 or 2 heteroatoms chosen from nitrogen and oxygen;

$R^5$ is either absent or is hydrogen or $C_1$-$C_6$ alkyl to provide a quaternary amine;

m, n, and p are either the same or different and independently either 0 or 1 with the proviso that m, n, and p are not simultaneously 0;

q is 2, 3, or 4; and

Y and Z are either the same or different and independently O, S, or NH.

In one particular embodiment, q is 2.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

"Halogen" means fluoro, chloro, bromo and iodo.

In certain embodiments, the amino lipid has the following structure (II):

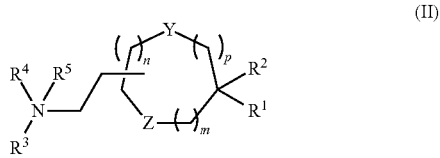

(II)

or salts thereof, wherein

R$^1$ and R$^2$ are either the same or different and independently optionally substituted C$_{12}$-C$_{24}$ alkyl, optionally substituted C$_{12}$-C$_{24}$ alkenyl, optionally substituted C$_{12}$-C$_{24}$ alkynyl, or optionally substituted C$_{12}$-C$_{24}$ acyl;

R$^3$ and R$^4$ are either the same or different and independently optionally substituted C$_1$-C$_6$ alkyl, optionally substituted C$_1$-C$_6$ alkenyl, or optionally substituted C$_1$-C$_6$ alkynyl or R$^3$ and R$^4$ may join to form an optionally substituted heterocyclic ring of 4 to 6 carbon atoms and 1 or 2 heteroatoms chosen from nitrogen and oxygen;

R$^5$ is either absent or is hydrogen or C$_1$-C$_6$ alkyl to provide a quaternary amine;

m, n, and p are either the same or different and independently either 0 or 1 with the proviso that m, n, and p are not simultaneously 0;

Y and Z are either the same or different and independently O, S, or NH.

In certain embodiments, the amino lipid has the following structure (III):

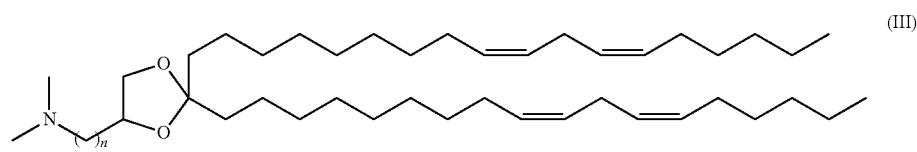

(III)

wherein
n is 2, 3, or 4.
In one particular embodiment, n is 2.

In certain embodiments, an amino lipid of the present invention has one of the following structures:

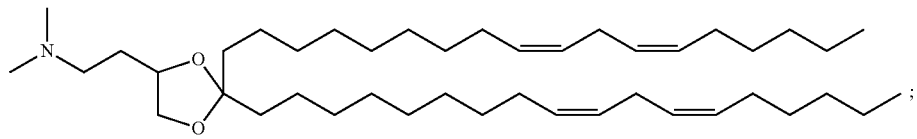

DLin-K-C2-DMA
C$_{43}$H$_{79}$NO$_2$
Exact Mass: 641.61
Mol. Wt.: 642.09
C, 80.43; H, 12.40; N, 2.18; O, 4.98

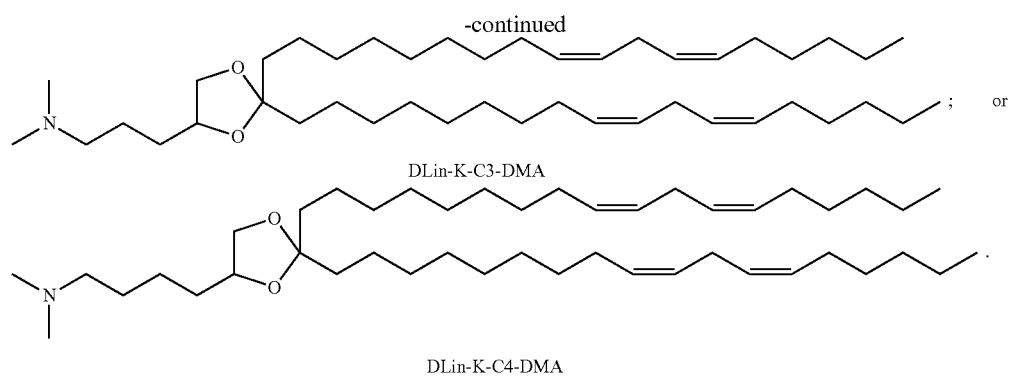
DLin-K-C3-DMA
DLin-K-C4-DMA
In certain embodiments, an amino lipid of the present invention has one of the following structures:
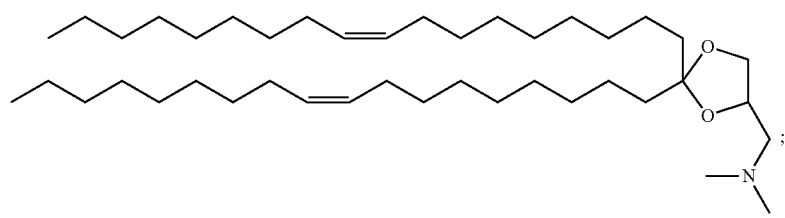
DO-K-DMA
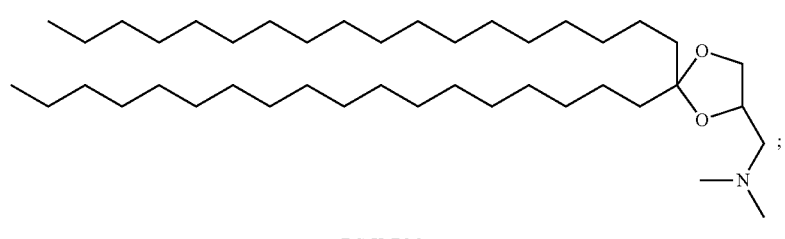
DS-K-DMA
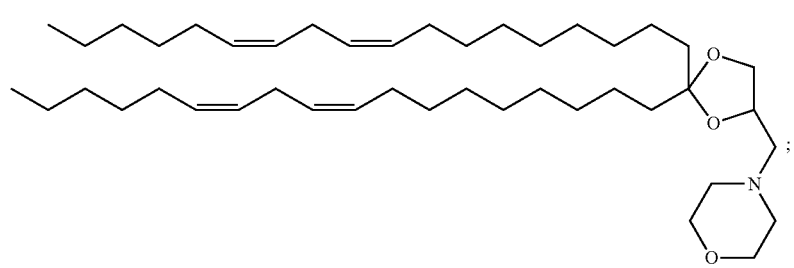
DLin-K-MA
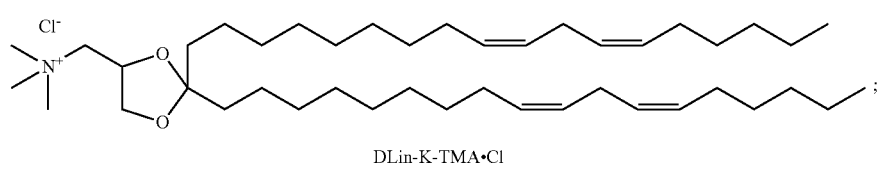
DLin-K-TMA·Cl

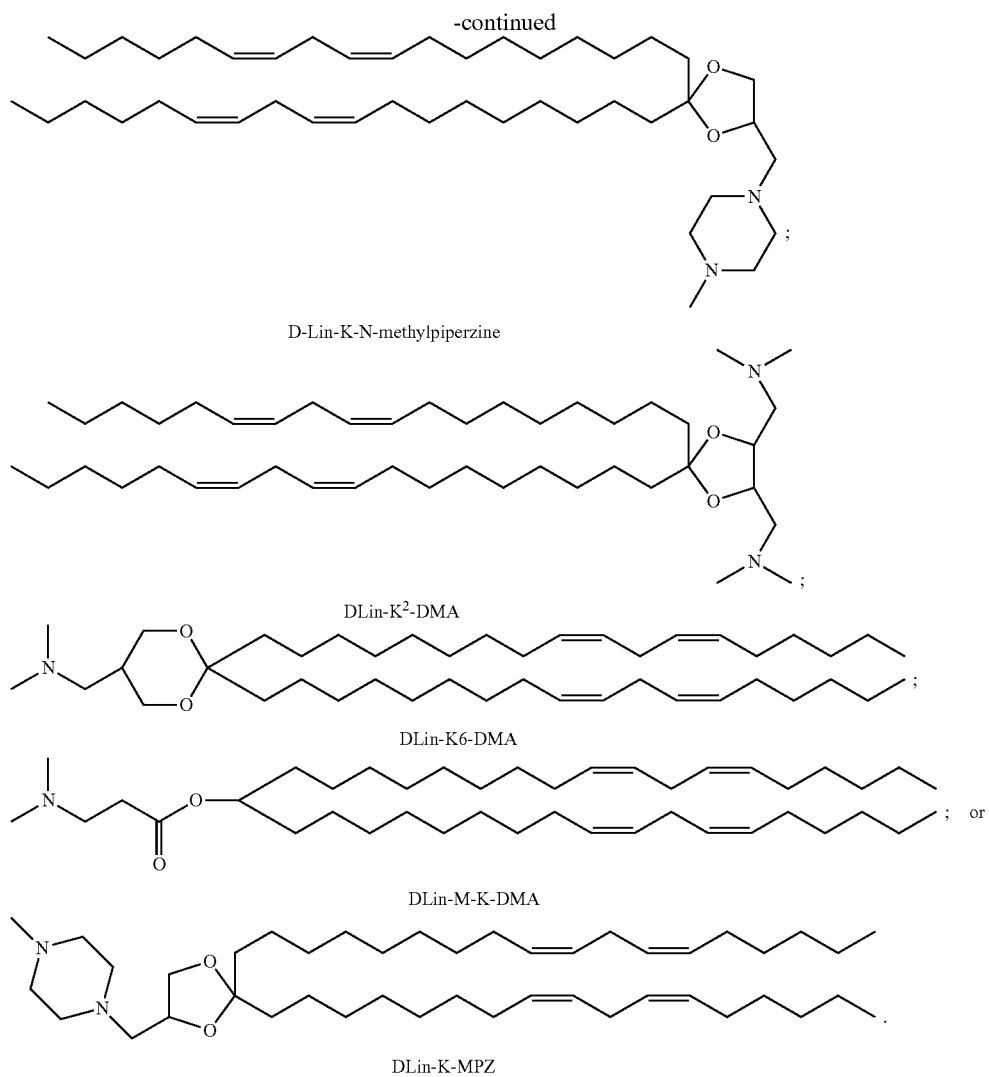

D-Lin-K-N-methylpiperzine

DLin-K²-DMA

DLin-K6-DMA

DLin-M-K-DMA ; or

DLin-K-MPZ

In some embodiments, the methods of the invention may require the use of protecting groups. Protecting group methodology is well known to those skilled in the art (see, for example, Protective Groups in Organic Synthesis, Green, T. W. et. al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

The compounds of the present invention may be prepared by known organic synthesis techniques, including the methods described in more detail in the Examples. In general, the compounds of structure (I) above may be made by the following Reaction Schemes 1 or 2, wherein all substituents are as defined above unless indicated otherwise.

Compounds of structure (I) wherein m is 1 and p is 0 can be prepared according to Reaction Scheme 1. Ketone 1 and Grignard reagent 2, wherein P is an alcohol protecting group such as trityl, can be purchased or prepared according to methods known to those of ordinary skill in the art. Reaction of 1 and 2 yields alcohol 3. Deprotection of 3, for example by treatment with mild acid, followed by bromination with an appropriate bromination reagent, for example phosphorous tribromide, yields 4 and 5 respectively. Treatment of bromide 5 with 6 yields the heterocyclic compound 7. Treatment of 7 with amine 8 then yields a compound of structure (I) wherein m is 1 and $R^5$ is absent (9). Further treatment of 9 with chloride 10 yields compounds of structure (I) wherein m is 1 and $R^5$ is present.

1. Reaction Scheme 1

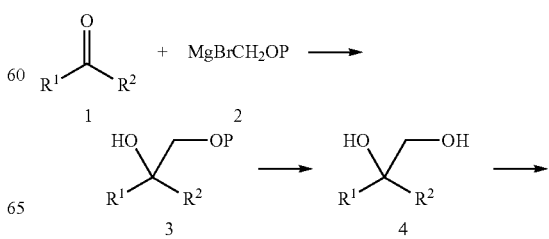

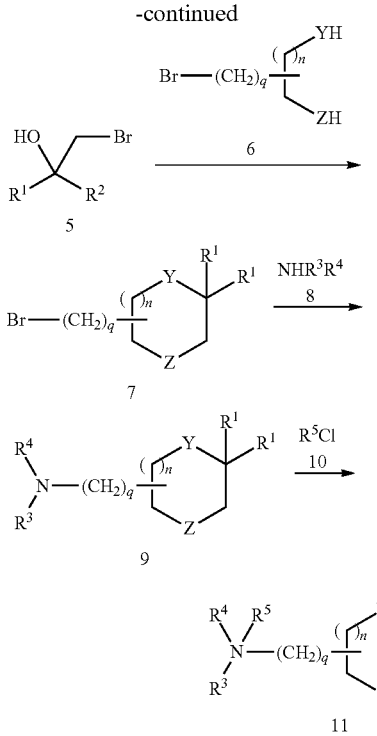

In certain embodiments where m and p are 1 and n is 0, compounds of this invention can be prepared according to Reaction Scheme 3. Compounds 12 and 13 can be purchased or prepared according to methods know to those of ordinary skill in the art. Reaction of 12 and 13 yields a compound of structure (I) where $R^5$ is absent (14). In other embodiments where $R^5$ is present, 13 can be treated with 10 to obtain compounds of structure 15.

3. Reaction Scheme 3

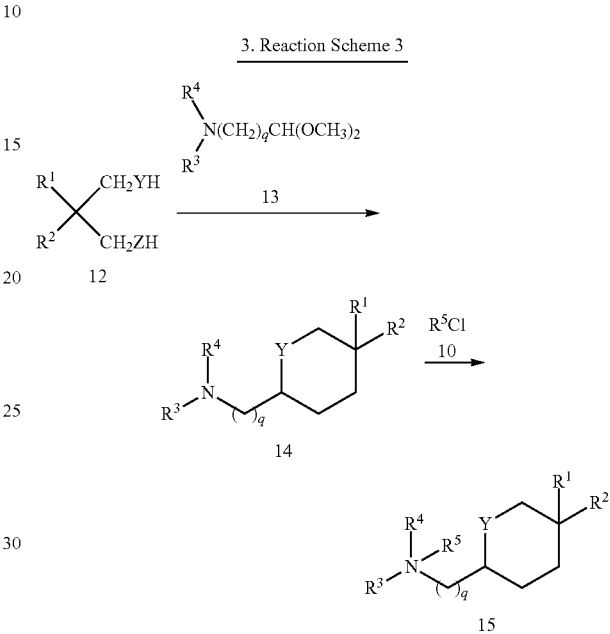

Compounds of structure (I) wherein m and p are 0 can be prepared according to Reaction Scheme 2. Ketone 1 and bromide 6 can be purchased or prepared according to methods known to those of ordinary skill in the art. Reaction of 1 and 6 yields heterocycle 12. Treatment of 12 with amine 8 yields compounds of structure (I) wherein m is 0 and $R^5$ is absent (13). Further treatment of 13 with 10 produces compounds of structure (I) wherein w is 0 and $R^5$ is present.

In certain other embodiments where either m or p is 1 and n is 0, compounds of this invention can be prepared according to Reaction Scheme 4. Compound 16 can be purchased or prepared according to methods know to those of ordinary skill in the art and reacted with 13 to yield a compound of structure (I) where $R^5$ is absent (17). Other embodiments of structure (I) where $R^5$ is present can be prepared by treatment of 17 with 10 to yield compounds of structure 18.

2. Reaction Scheme 2

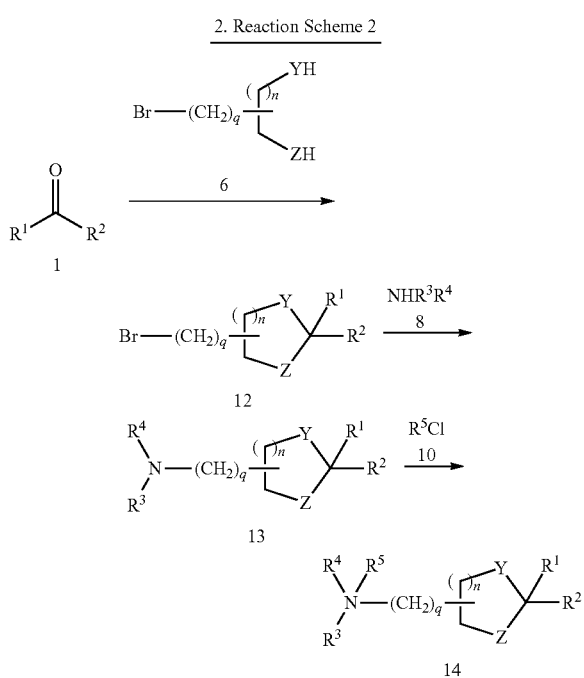

4. Reaction Scheme 4

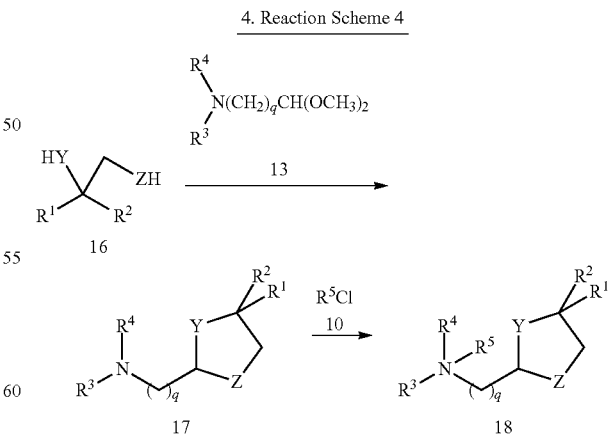

In certain specific embodiments of structure (I) where n is 1 and m and p are 0, compounds of this invention can be prepared according to Reaction Scheme 5. Compound 19 can be purchased or prepared according to methods known to those of ordinary skill in the art. Reaction of 19 with formaldehyde followed by removal of an optional alcohol protecting group (P), yields alcohol 20. Bromination of 20 followed by treatment with amine 8 yields 22. Compound 22 can then be treated with n-butyl lithium and $R^1I$ followed by further treatment with n-butyl lithium and $R^2I$ to yield a compound of structure (I) where $R^5$ is absent (23). Further treatment of 23 with 10 yields a compound of structure (I) where $R^5$ is present (24).

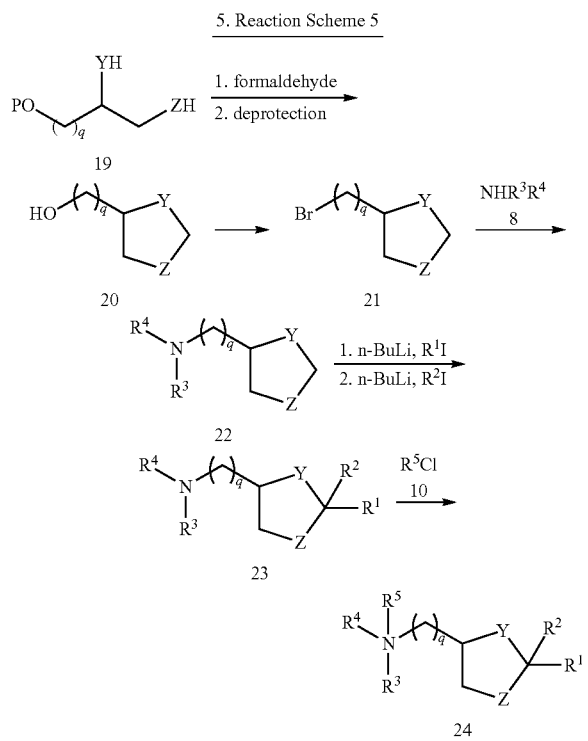

In particular embodiments, the amino lipids of the present invention are cationic lipids. As used herein, the term "amino lipid" is meant to include those lipids having one or two fatty acid or fatty alkyl chains and an amino head group (including an alkylamino or dialkylamino group) that may be protonated to form a cationic lipid at physiological pH.

Other amino lipids would include those having alternative fatty acid groups and other dialkylamino groups, including those in which the alkyl substituents are different (e.g., N-ethyl-N-methylamino-, N-propyl-N-ethylamino- and the like). For those embodiments in which $R^{11}$ and $R^{12}$ are both long chain alkyl or acyl groups, they can be the same or different. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ are preferred. Other scaffolds can also be used to separate the amino group and the fatty acid or fatty alkyl portion of the amino lipid. Suitable scaffolds are known to those of skill in the art.

In certain embodiments, amino or cationic lipids of the present invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention.

In certain embodiments, protonatable lipids according to the invention have a pKa of the protonatable group in the range of about 4 to about 11. Most preferred is pKa of about 4 to about 7, because these lipids will be cationic at a lower pH formulation stage, while particles will be largely (though not completely) surface neutralized at physiological pH around pH 7.4. One of the benefits of this pKa is that at least some nucleic acid associated with the outside surface of the particle will lose its electrostatic interaction at physiological pH and be removed by simple dialysis; thus greatly reducing the particle's susceptibility to clearance.

B. Lipid Particles

The present invention also provides lipid particles comprising one or more of the amino lipids described above. Lipid particles include, but are not limited to, liposomes. As used herein, a liposome is a structure having lipid-containing membranes enclosing an aqueous interior. Liposomes may have one or more lipid membranes. The invention contemplates both single-layered liposomes, which are referred to as unilamellar, and multi-layered liposomes, which are referred to as multilamellar. When complexed with nucleic acids, lipid particles may also be lipoplexes, which are composed of cationic lipid bilayers sandwiched between DNA layers, as described, e.g., in Felgner, *Scientific American*.

The lipid particles of the present invention may further comprise one or more additional lipids and/or other components, such as cholesterol. Other lipids may be included in the liposome compositions of the present invention for a variety of purposes, such as to prevent lipid oxidation or to attach ligands onto the liposome surface. Any of a number of lipids may be present in liposomes of the present invention, including amphipathic, neutral, cationic, and anionic lipids. Such lipids can be used alone or in combination. Specific examples of additional lipid components that may be present are described below.

In certain embodiments, lipid particles of the present invention comprise an amino lipid described above, a non-cationic or neutral lipid, and a conjugated lipid that inhibits particle aggregation. In certain embodiments, lipid particles of the present invention comprise an amino lipid described above, a non-cationic or neutral lipid, a sterol, and a conjugated lipid that inhibits particle aggregation. In particular embodiments, these lipid particles further comprise a cationic lipid in addition to the amino lipid of the present invention.

Additional components that may be present in a lipid particle of the present invention include bilayer stabilizing components such as polyamide oligomers (see, e.g., U.S. Pat. No. 6,320,017), peptides, proteins, detergents, lipid-derivatives, such as PEG coupled to phosphatidylethanolamine and PEG conjugated to ceramides (see, U.S. Pat. No. 5,885,613).

Examples of lipids that reduce aggregation of particles during formation include polyethylene glycol (PEG)-modified lipids, monosialoganglioside Gm1, and polyamide oligomers ("PAO") such as (described in U.S. Pat. No. 6,320,017). Other compounds with uncharged, hydrophilic, steric-barrier moieties, which prevent aggregation during formulation, like PEG, Gm1 or ATTA, can also be coupled to lipids for use as in the methods and compositions of the invention. ATTA-lipids are described, e.g., in U.S. Pat. No.

6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids).

Specific examples of PEG-modified lipids (or lipid-polyoxyethylene conjugates) that are useful in the present invention can have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in co-pending U.S. Ser. No. 08/486,214, incorporated herein by reference, PEG-modified dialkylamines and PEG-modified 1,2-diacyloxypropan-3-amines. Particularly preferred are PEG-modified diacylglycerols and dialkylglycerols.

In particular embodiments, a PEG-lipid is selected from:

preferable for the nucleic acid-lipid particle to exhibit a longer plasma circulation lifetime and hence the PEG-modified lipid will possess relatively longer lipid anchors.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

The term "non-cationic lipid" refers to any amphipathic lipid as well as any other neutral lipid or anionic lipid. Non-cationic lipids used in the lipid particles, e.g., SNALP, of the present invention can be any of a variety of neutral uncharged, zwitterionic, or anionic lipids capable of producing a stable complex.

The term "neutral lipid" refers to any of a number of lipid species that exist either in an uncharged or neutral zwitterionic form at a selected pH. At physiological pH, such lipids

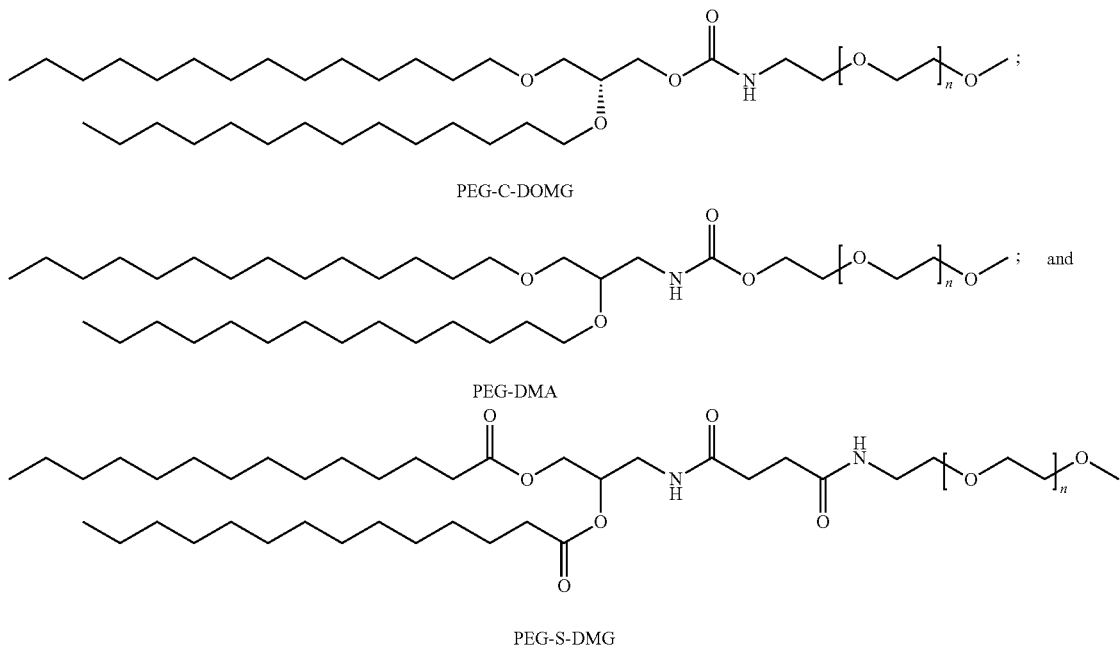

PEG-C-DOMG

PEG-DMA

PEG-S-DMG

In embodiments where a sterically-large moiety such as PEG or ATTA are conjugated to a lipid anchor, the selection of the lipid anchor depends on what type of association the conjugate is to have with the lipid particle. It is well known that mePEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a $T_{1/2}$ less than 60 mins. in some assays. As illustrated in U.S. patent application Ser. No. 08/486,214, at least three characteristics influence the rate of exchange: length of acyl chain, saturation of acyl chain, and size of the steric-barrier head group. Compounds having suitable variations of these features may be useful for the invention. For some therapeutic applications it may be preferable for the PEG-modified lipid to be rapidly lost from the nucleic acid-lipid particle in vivo and hence the PEG-modified lipid will possess relatively short lipid anchors. In other therapeutic applications it may be include, for example, diacylphosphatidylcholine, diacylphosphatidylethanolamine, ceramide, sphingomyelin, cephalin, cholesterol, cerebrosides, and diacylglycerols.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the present invention are DOPE, DSPC, POPC, or any related phosphatidylcholine. The neutral lipids useful in the present invention may also be composed of sphingomyelin, dihydrosphingomyeline, or phospholipids with other head groups, such as serine and inositol.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyolphosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lyso-phosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof such as cholestanol, cholestanone, cholestenone, and coprostanol.

In some embodiments, the non-cationic lipid present in the lipid particle, e.g., SNALP, comprises or consists of cholesterol, e.g., a phospholipid-free SNALP. In other embodiments, the non-cationic lipid present in the lipid particle, e.g., SNALP comprises or consists of one or more phospholipids, e.g., a cholesterol-free SNALP. In further embodiments, the non-cationic lipid present in the SNALP comprises or consists of a mixture of one or more phospholipids and cholesterol.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

The non-cationic lipid typically comprises from about 13 mol % to about 49.5 mol %, about 20 mol % to about 45 mol %, about 25 mol % to about 45 mol %, about 30 mol % to about 45 mol %, about 35 mol % to about 45 mol %, about 20 mol % to about 40 mol %, about 25 mol % to about 40 mol %, or about 30 mol % to about 40 mol % of the total lipid present in the particle.

The sterol component of the lipid mixture, when present, can be any of those sterols conventionally used in the field of liposome, lipid vesicle or lipid particle preparation. A preferred sterol is cholesterol.

Other cationic lipids, which carry a net positive charge at about physiological pH, in addition to those specifically described above, may also be included in lipid particles of the present invention. Such cationic lipids include, but are not limited to, N,N-dioleyl-N,N-dimethylammonium chloride ("DODAC"); N-(2,3-dioleyloxy)propyl-N,N-N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N-(N',N'-dimethylaminoethane)-carbamoyl)cholesterol ("DC-Chol"), N-(1-(2,3-dioleyloxy)propyl)-N'-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

In numerous embodiments, amphipathic lipids are included in lipid particles of the present invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Also suitable for inclusion in the lipid particles of the present invention are programmable fusion lipids. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the lipid particle membrane over time. By the time the lipid particle is suitably distributed in the body, it has lost sufficient cloaking agent so as to be fusogenic. With other signal events, it is desirable to choose a signal that is associated with the disease site or target cell, such as increased temperature at a site of inflammation.

In certain embodiments, it is desirable to target the lipid particles of this invention using targeting moieties that are specific to a cell type or tissue. Targeting of lipid particles using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can comprise the entire protein or fragments thereof. Targeting mechanisms generally require that the targeting agents be positioned on the surface of the lipid particle in such a manner that the target moiety is available for interaction with the target, for example, a cell surface receptor. A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002).

The use of lipid particles, i.e., liposomes, with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013, 556; Zalipsky, *Bioconjugate Chemistry* 4: 296-299 (1993); Zalipsky, FEBS Letters 353: 71-74 (1994); Zalipsky, in Stealth Liposomes Chapter 9 (Lasic and Martin, Eds) CRC Press, Boca Raton, Fla. (1995). In one approach, a ligand, such as an antibody, for targeting the lipid particle is linked to the polar head group of lipids forming the lipid particle. In another approach, the targeting ligand is attached to the distal ends of the PEG chains forming the hydrophilic polymer coating (Klibanov, et al., *Journal of Liposome Research* 2: 321-334 (1992); Kirpotin et al., FEBS Letters 388: 115-118 (1996)).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci.* (*USA*), 87:2448-2451 (1990). Other examples of antibody conjugation are disclosed in U.S. Pat. No. 6,027,726, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes*, 149 Methods in Enzymology 111-119 (Academic Press, Inc. 1987)). Other targeting methods include the biotin-avidin system.

In one exemplary embodiment, the lipid particle comprises a mixture of an amino lipid of the present invention, neutral lipids (other than an amino lipid), a sterol (e.g., cholesterol) and a PEG-modified lipid (e.g., a PEG-S-DMG, PEG-C-DOMG or PEG-DMA). In certain embodiments, the lipid mixture consists of or consists essentially of an amino lipid of the present invention, a neutral lipid, cholesterol, and a PEG-modified lipid. In further preferred embodiments, the lipid particle consists of or consists essentially of the above lipid mixture in molar ratios of about 20-70% amino lipid: 5-45% neutral lipid:20-55% cholesterol:0.5-15% PEG-modified lipid.

In particular embodiments, the lipid particle consists of or consists essentially of DLin-K-C2-DMA, DSPC, Chol, and either PEG-S-DMG, PEG-C-DOMG or PEG-DMA, e.g., in a molar ratio of about 20-60% DLin-K-C2-DMA: 5-25% DSPC:25-55% Chol:0.5-15% PEG-S-DMG, PEG-C-DOMG or PEG-DMA. In particular embodiments, the molar lipid ratio is approximately 40/10/40/10 (mol % DLin-K-C2-DMA/DSPC/Chol/PEG-S-DMG or DLin-K-C2-DMA/DSPC/Chol/PEG-C-DOMG or DLin-K-C2-DMA/DSPC/Chol/PEG-DMA) or 35/15/40/10 mol % DLin-K-C2-DMA/DSPC/Chol/PEG-S-DMG or DLin-K-C2-DMA/DSPC/Chol/PEG-C-DOMG or DLin-K-C2-DMA/DSPC/Chol/PEG-DMA. In another group of embodiments, the neutral lipid in these compositions is replaced with POPC, DOPE or SM.

In particular embodiments, the lipid particle consists of or consists essentially of DLin-$K^2$-DMA, DSPC, Chol, and either PEG-S-DMG, PEG-C-DOMG or PEG-DMA, e.g., in a molar ratio of about 20-60% DLin-$K^2$-DMA: 5-25% DSPC:25-55% Chol:0.5-15% PEG-S-DMG, PEG-C-DOMG or PEG-DMA. In particular embodiments, the molar lipid ratio is approximately 40/10/40/10 (mol % DLin-$K^2$-DMA/DSPC/Chol/PEG-S-DMG or DLin-$K^2$-DMA/DSPC/Chol/PEG-C-DOMG or DLin-$K^2$-DMA/DSPC/Chol/PEG-DMA) or 35/15/40/10 mol % DLin-$K^2$-DMA/DSPC/Chol/PEG-S-DMG or DLin-$K^2$-DMA/DSPC/Chol/PEG-C-DOMG or DLin-$K^2$-DMA/DSPC/Chol/PEG-DMA. In another group of embodiments, the neutral lipid in these compositions is replaced with POPC, DOPE or SM.

In particular embodiments, the lipid particle consists of or consists essentially of DLin-K6-DMA, DSPC, Chol, and either PEG-S-DMG, PEG-C-DOMG or PEG-DMA, e.g., in a molar ratio of about 20-60% DLin-K6-DMA: 5-25% DSPC:25-55% Chol:0.5-15% PEG-S-DMG, PEG-C-DOMG or PEG-DMA. In particular embodiments, the molar lipid ratio is approximately 40/10/40/10 (mol % DLin-K6-DMA/DSPC/Chol/PEG-S-DMG or DLin-K6-DMA/DSPC/Chol/PEG-C-DOMG or DLin-K6-DMA/DSPC/Chol/PEG-DMA) or 35/15/40/10 mol % DLin-K6-DMA/DSPC/Chol/PEG-S-DMG or DLin-K6-DMA/DSPC/Chol/PEG-C-DOMG or DLin-K6-DMA/DSPC/Chol/PEG-DMA. In another group of embodiments, the neutral lipid in these compositions is replaced with POPC, DOPE or SM.

C. Therapeutic Agent-Lipid Particle Compositions and Formulations

The present invention includes compositions comprising a lipid particle of the present invention and an active agent, wherein the active agent is associated with the lipid particle. In particular embodiments, the active agent is a therapeutic agent. In particular embodiments, the active agent is encapsulated within an aqueous interior of the lipid particle. In other embodiments, the active agent is present within one or more lipid layers of the lipid particle. In other embodiments, the active agent is bound to the exterior or interior lipid surface of a lipid particle.

"Fully encapsulated" as used herein indicates that the nucleic acid in the particles is not significantly degraded after exposure to serum or a nuclease assay that would significantly degrade the free nucleic acid. In a fully encapsulated system, preferably less than 25% of particle nucleic acid is degraded in a treatment that would normally degrade 100% of free nucleic acid, more preferably less than 10% and most preferably less than 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA or RNA in solution (available from Invitrogen Corporation, Carlsbad, Calif.). Fully encapsulated also suggests that the particles are serum stable, that is, that they do not rapidly decompose into their component parts upon in vivo administration.

Active agents, as used herein, include any molecule or compound capable of exerting a desired effect on a cell, tissue, organ, or subject. Such effects may be biological, physiological, or cosmetic, for example. Active agents may be any type of molecule or compound, including e.g., nucleic acids, peptides and polypeptides, including, e.g., antibodies, such as, e.g., polyclonal antibodies, monoclonal antibodies, antibody fragments; humanized antibodies, recombinant antibodies, recombinant human antibodies, and Primatized™ antibodies, cytokines, growth factors, apoptotic factors, differentiation-inducing factors, cell surface receptors and their ligands; hormones; and small molecules, including small organic molecules or compounds.

In one embodiment, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative lacks therapeutic activity.

In various embodiments, therapeutic agents include any therapeutically effective agent or drug, such as anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs, e.g., anti-arrhythmic agents, vasoconstrictors, hormones, and steroids.

In certain embodiments, the therapeutic agent is an oncology drug, which may also be referred to as an anti-tumor drug, an anti-cancer drug, a tumor drug, an antineoplastic agent, or the like. Examples of oncology drugs that may be used according to the invention include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litertinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs that may be used according to the invention are ellipticin and ellipticin analogs or derivatives, epothilones, intracellular kinase inhibitors and camptothecins.

1. Nucleic Acid-Lipid Particles

In certain embodiments, lipid particles of the present invention are associated with a nucleic acid, resulting in a nucleic acid-lipid particle. In particular embodiments, the nucleic acid is partially or fully encapsulated in the lipid particle. As used herein, the term "nucleic acid" is meant to include any oligonucleotide or polynucleotide. Fragments containing up to 50 nucleotides are generally termed oligonucleotides, and longer fragments are called polynucleotides.

In particular embodiments, oligonucleotides of the present invention are 20-50 nucleotides in length.

In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Oligonucleotides are classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a lipid-nucleic acid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNA, and triplex-forming oligonucleotides.

Nucleic acids of the present invention may be of various lengths, generally dependent upon the particular form of nucleic acid. For example, in particular embodiments, plasmids or genes may be from about 1,000 to 100,000 nucleotide residues in length. In particular embodiments, oligonucleotides may range from about 10 to 100 nucleotides in length. In various related embodiments, oligonucleotides, both single-stranded, double-stranded, and triple-stranded, may range in length from about 10 to about 50 nucleotides, from about 20 to about 50 nucleotides, from about 15 to about 30 nucleotides, from about 20 to about 30 nucleotides in length.

In particular embodiments, an oligonucleotide (or a strand thereof) of the present invention specifically hybridizes to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions as compared to the region of a gene or mRNA sequence that it is targeting or to which it specifically hybridizes.

RNA Interference Nucleic Acids

In particular embodiments, nucleic acid-lipid particles of the present invention are associated with RNA interference (RNAi) molecules. RNA interference methods using RNAi molecules may be used to disrupt the expression of a gene or polynucleotide of interest. In the last 5 years small interfering RNA (siRNA) has essentially replaced antisense ODN and ribozymes as the next generation of targeted oligonucleotide drugs under development. SiRNAs are RNA duplexes normally 21-30 nucleotides long that can associate with a cytoplasmic multi-protein complex known as RNAi-induced silencing complex (RISC). RISC loaded with siRNA mediates the degradation of homologous mRNA transcripts, therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense ODN or ribozymes. A variety of RNAi reagents, including siRNAs targeting clinically relevant targets, are currently under pharmaceutical development, as described, e.g., in de Fougerolles, A. et al., *Nature Reviews* 6:443-453 (2007).

While the first described RNAi molecules were RNA:RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton, J. S, and Christian, A. T., (2003) *Molecular Biotechnology* 24:111-119). Thus, the invention includes the use of RNAi molecules comprising any of these different types of double-stranded molecules. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded polynucleotides comprising two separate strands, i.e. a sense strand and an antisense strand, e.g., small interfering RNA (siRNA); polynucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

RNA interference (RNAi) may be used to specifically inhibit expression of target polynucleotides. Double-stranded RNA-mediated suppression of gene and nucleic acid expression may be accomplished according to the invention by introducing dsRNA, siRNA or shRNA into cells or organisms. SiRNA may be double-stranded RNA, or a hybrid molecule comprising both RNA and DNA, e.g., one RNA strand and one DNA strand. It has been demonstrated that the direct introduction of siRNAs to a cell can trigger RNAi in mammalian cells (Elshabir, S. M., et al. *Nature* 411:494-498 (2001)). Furthermore, suppression in mammalian cells occurred at the RNA level and was specific for the targeted genes, with a strong correlation between RNA and protein suppression (Caplen, N. et al., *Proc. Natl. Acad. Sci. USA* 98:9746-9747 (2001)). In addition, it was shown that a wide variety of cell lines, including HeLa S3, COS7, 293, NIH/3T3, A549, HT-29, CHO-KI and MCF-7 cells, are susceptible to some level of siRNA silencing (Brown, D. et al. TechNotes 9(1):1-7, available at http://www.dot.ambion.dot.com/techlib/tn/91/912.html (Sep. 1, 2002)).

RNAi molecules targeting specific polynucleotides can be readily prepared according to procedures known in the art. Structural characteristics of effective siRNA molecules have been identified. Elshabir, S. M. et al. (2001) *Nature* 411:494-498 and Elshabir, S. M. et al. (2001), *EMBO* 20:6877-6888. Accordingly, one of skill in the art would understand that a wide variety of different siRNA molecules may be used to target a specific gene or transcript. In certain embodiments, siRNA molecules according to the invention are double-stranded and 16-30 or 18-25 nucleotides in length, including each integer in between. In one embodiment, an siRNA is 21 nucleotides in length. In certain embodiments, siRNAs have 0-7 nucleotide 3' overhangs or 0-4 nucleotide 5' overhangs. In one embodiment, an siRNA molecule has a two nucleotide 3' overhang. In one embodiment, an siRNA is 21 nucleotides in length with two nucleotide 3' overhangs (i.e. they contain a 19 nucleotide complementary region between the sense and antisense strands). In certain embodiments, the overhangs are UU or dTdT 3' overhangs.

Generally, siRNA molecules are completely complementary to one strand of a target DNA molecule, since even single base pair mismatches have been shown to reduce silencing. In other embodiments, siRNAs may have a modified backbone composition, such as, for example, 2'-deoxy- or 2'-O-methyl modifications. However, in preferred embodiments, the entire strand of the siRNA is not made with either 2' deoxy or 2'-O-modified bases.

In one embodiment, siRNA target sites are selected by scanning the target mRNA transcript sequence for the occurrence of AA dinucleotide sequences. Each AA dinucleotide sequence in combination with the 3'adjacent approximately 19 nucleotides are potential siRNA target sites. In one embodiment, siRNA target sites are preferentially not located within the 5' and 3' untranslated regions (UTRs) or regions near the start codon (within approximately 75 bases), since proteins that bind regulatory regions may interfere with the binding of the siRNP endonuclease complex (Elshabir, S. et al. *Nature* 411:494-498 (2001); Elshabir, S. et al. *EMBO J.* 20:6877-6888 (2001)). In addition, potential target sites may be compared to an appropriate genome database, such as BLASTN 2.0.5, available on the NCBI server at www.ncbi.nlm, and potential target sequences with significant homology to other coding sequences eliminated.

In particular embodiments, short hairpin RNAs constitute the nucleic acid component of nucleic acid-lipid particles of the present invention. Short Hairpin RNA (shRNA) is a form of hairpin RNA capable of sequence-specifically reducing expression of a target gene. Short hairpin RNAs may offer an advantage over siRNAs in suppressing gene expression, as they are generally more stable and less susceptible to degradation in the cellular environment. It has been established that such short hairpin RNA-mediated gene silencing works in a variety of normal and cancer cell lines, and in mammalian cells, including mouse and human cells. Paddison, P. et al., *Genes Dev.* 16(8):948-58 (2002). Furthermore, transgenic cell lines bearing chromosomal genes that code for engineered shRNAs have been generated. These cells are able to constitutively synthesize shRNAs, thereby facilitating long-lasting or constitutive gene silencing that may be passed on to progeny cells. Paddison, P. et al., *Proc. Natl. Acad. Sci. USA* 99(3):1443-1448 (2002).

ShRNAs contain a stem loop structure. In certain embodiments, they may contain variable stem lengths, typically from 19 to 29 nucleotides in length, or any number in between. In certain embodiments, hairpins contain 19 to 21 nucleotide stems, while in other embodiments, hairpins contain 27 to 29 nucleotide stems. In certain embodiments, loop size is between 4 to 23 nucleotides in length, although the loop size may be larger than 23 nucleotides without significantly affecting silencing activity. ShRNA molecules may contain mismatches, for example G-U mismatches between the two strands of the shRNA stem without decreasing potency. In fact, in certain embodiments, shRNAs are designed to include one or several G-U pairings in the hairpin stem to stabilize hairpins during propagation in bacteria, for example. However, complementarity between the portion of the stem that binds to the target mRNA (antisense strand) and the mRNA is typically required, and even a single base pair mismatch is this region may abolish silencing. 5' and 3' overhangs are not required, since they do not appear to be critical for shRNA function, although they may be present (Paddison et al. (2002) Genes & Dev. 16(8):948-58).

MicroRNAs

Micro RNAs (miRNAs) are a highly conserved class of small RNA molecules that are transcribed from DNA in the genomes of plants and animals, but are not translated into protein. Processed miRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: Griffiths-Jones S, et al. *NAR*, 2006, 34, Database Issue, D140-D144; Griffiths-Jones S. *NAR*, 2004, 32, Database Issue, D109-D111; and also at http://microrna.sanger.ac.uk/sequences/.

Antisense Oligonucleotides

In one embodiment, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence. In the case of antisense RNA, they prevent translation of complementary RNA strands by binding to it. Antisense DNA can be used to target a specific, complementary (coding or non-coding) RNA. If binding takes places this DNA/RNA hybrid can be degraded by the enzyme RNase H. In particular embodiment, antisense oligonucleotides contain from about 10 to about 50 nucleotides, more preferably about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., *Science*. 1988 Jun. 10; 240(4858):1544-6; Vasanthakumar and Ahmed, *Cancer Commun*. 1989; 1(4):225-32; Penis et al., *Brain Res Mol Brain Res*. 1998 Jun. 15; 57(2):310-20; U.S. Pat. No. 5,801,154; U.S. Pat. No. 5,789,573; U.S. Pat. No. 5,718,709 and U.S. Pat. No. 5,610,288). Furthermore, antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res*. 1997, 25(17):3389-402).

Ribozymes

According to another embodiment of the invention, nucleic acid-lipid particles are associated with ribozymes. Ribozymes are RNA-protein complexes having specific catalytic domains that possess endonuclease activity (Kim and Cech, *Proc Natl Acad Sci USA*. 1987 December; 84(24):8788-92; Forster and Symons, *Cell*. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., *Cell*. 1981 December; 27(3 Pt 2):487-96; Michel and Westhof, *J Mol. Biol*. 1990 Dec. 5; 216(3):585-610; Reinhold-Hurek and Shub, *Nature*. 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or Neurospora VS RNA motif, for example. Specific examples of hammerhead motifs are described by Rossi et al, Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to any polynucleotide sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Immunostimulatory Oligonucleotides

Nucleic acids associated with lipid particles of the present invention may be immunostimulatory, including immunostimulatory oligonucleotides (ISS; single- or double-stranded) capable of inducing an immune response when administered to a subject, which may be a mammal or other patient. ISS include, e.g., certain palindromes leading to hairpin secondary structures (see Yamamoto S., et al. (1992) J. Immunol. 148: 4072-4076), or CpG motifs, as well as other known ISS features (such as multi-G domains, see WO 96/11266).

The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

In particular embodiments, an immunostimulatory nucleic acid is only immunostimulatory when administered in combination with a lipid particle, and is not immunostimulatory when administered in its "free form." According to the present invention, such an oligonucleotide is considered to be immunostimulatory.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. In a specific embodiment, the nucleic acid comprises the sequence 5' TAACGTTGAGGGGCAT 3' (SEQ ID NO:2). In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of said CpG dinucleotides comprises a methylated cytosine. Exemplary immunostimulatory oligonucleotides are shown in Table 1.

In one specific embodiment, the nucleic acid comprises the sequence 5' TTCCATGACGTTCCTGACGT 3' (SEQ ID NO:1). In another specific embodiment, the nucleic acid sequence comprises the sequence 5' TCCATGACGTTCCTGACGT 3' (SEQ ID NO:31), wherein the two cytosines indicated in bold are methylated. In particular embodiments, the ODN is selected from a group of ODNs consisting of ODN #1, ODN #2, ODN #3, ODN #4, ODN #5, ODN #6, ODN #7, ODN #8, and ODN #9, as shown below.

TABLE 1

Exemplary Immunostimulatory Oligonucleotides (ODNs)

| ODN NAME | ODN SEQ ID NO | ODN SEQUENCE (5'-3'). |
|---|---|---|
| ODN 1 (INX-6295) human c-myc | SEQ ID NO: 2 | 5'-TAACGTTGAGGGGCAT-3 |
| * ODN 1m (INX-6303) | SEQ ID NO: 4 | 5'-TAAZGTTGAGGGGCAT-3 |
| ODN 2 (INX-1826) | SEQ ID NO: 1 | 5'-TCCATGACGTTCCTGACGTT-3 |
| * ODN 2m (INX-1826m) | SEQ ID NO: 31 | 5'-TCCATGAZGTTCCTGAZGTT-3 |
| ODN 3 (INX-6300) | SEQ ID NO: 3 | 5'-TAAGCATACGGGGTGT-3 |
| ODN 5 (INX-5001) | SEQ ID NO: 5 | 5'-AACGTT-3 |

TABLE 1 -continued

Exemplary Immunostimulatory Oligonucleotides (ODNs)

| ODN NAME | ODN SEQ ID NO | ODN SEQUENCE (5'-3') |
|---|---|---|
| ODN 6 (INX-3002) | SEQ ID NO: 6 | 5'-GATGCTGTGTCGGGGTCTCCGGGC-3' |
| ODN 7 (INX-2006) | SEQ ID NO: 7 | 5'-TCGTCGTTTTGTCGTTTTGTCGTT-3' |
| ODN 7m (INX-2006m) | SEQ ID NO: 32 | 5'-TZGTZGTTTTGTZGTTTTGTZGTT-3' |
| ODN 8 (INX-1982) | SEQ ID NO: 8 | 5'-TCCAGGACTTCTCTCAGGTT-3' |
| ODN 9 (INX-G3139) | SEQ ID NO: 9 | 5'-TCTCCCAGCGTGCGCCAT-3' |
| ODN 10 (PS-3082) murine Intracellular Adhesion Molecule-1 | SEQ ID NO: 10 | 5'-TGCATCCCCCAGGCCACCAT-3' |
| ODN 11 (PS-2302) human Intracellular Adhesion Molecule-1 | SEQ ID NO: 11 | 5'-GCCCAAGCTGGCATCCGTCA-3' |
| ODN 12 (PS-8997) human Intracellular Adhesion Molecule-1 | SEQ ID NO: 12 | 5'-GCCCAAGCTGGCATCCGTCA-3' |
| ODN 13 (US3) human erb-B-2 | SEQ ID NO: 13 | 5'-GGT GCTCACTGC GGC-3' |
| ODN 14 (LR-3280) human c-myc | SEQ ID NO: 14 | 5'-AACC GTT GAG GGG CAT-3' |
| ODN 15 (LR-3001) human c-myc | SEQ ID NO: 15 | 5'-TAT GCT GTG CCG GGG TCT TCG GGC-3' |
| ODN 16 (Inx-6298) | SEQ ID NO: 16 | 5'-GTGCCG GGGTCTTCGGGC-3' |
| ODN 17 (hIGF-1R) human Insulin Growth Factor 1-Receptor | SEQ ID NO: 17 | 5'-GGACCCTCCTCCGGAGCC-3' |
| ODN 18 (LR-52) human Insulin Growth Factor 1-Receptor | SEQ ID NO: 18 | 5'-TCC TCC GGA GCC AGA CTT-3' |
| ODN 19 (hEGFR) human Epidermal Growth Factor-Receptor | SEQ ID NO: 19 | 5'-AAC GTT GAG GGG CAT-3' |
| ODN 20 (EGFR) Epidermal Growth Factor-Receptor | SEQ ID NO: 20 | 5'-CCGTGGTCA TGCTCC-3' |
| ODN 21 (hVEGF) human Vascular Endothelial Growth Factor | SEQ ID NO: 21 | 5'-CAG CCTGGCTCACCG CCTTGG-3' |
| ODN 22 (PS-4189) murine Phosphokinase C-alpha | SEQ ID NO: 22 | 5'-CAG CCA TGG TTC CCC CCA AC-3' |
| ODN 23 (PS-3521) | SEQ ID NO: 23 | 5'-GTT CTC GCT GGT GAG TTT CA-3' |
| ODN 24 (hBcl-2) human Bcl-2 | SEQ ID NO: 24 | 5'-TCT CCCAGCGTGCGCCAT-3' |
| ODN 25 (hC-Raf-1) human C-Raf-s | SEQ ID NO: 25 | 5'-GTG CTC CAT TGA TGC-3' |
| ODN #26 (hVEGF-R1) human Vascular Endothelial Growth Factor Receptor-1 | SEQ ID NO: 26 | 5'-GAGUUCUGAUGAGGCCGAAAGGCCGAAAGUCUG-3' |

TABLE 1 -continued

Exemplary Immunostimulatory Oligonucleotides (ODNs)

| ODN NAME | ODN SEQ ID NO | ODN SEQUENCE (5'-3'). |
|---|---|---|
| ODN #27 | SEQ ID NO: 27 | 5'-RRCGYY-3' |
| ODN #28 (INX-3280). | SEQ ID NO: 28 | 5'-AACGTTGAGGGGCAT-3' |
| ODN #29 (INX-6302) | SEQ ID NO: 29 | 5'-CAACGTTATGGGGAGA-3' |
| ODN #30 (INX-6298) human c-myc | SEQ ID NO: 30 | 5'-TAACGTTGAGGGGCAT-3' |

"Z" represents a methylated cytosine residue.

Note:
ODN 14 is a 15-mer oligonucleotide and ODN 1 is the same oligonucleotide having a thymidine added onto the 5' end making ODN 1 into a 16-mer. No difference in biological activity between ODN 14 and ODN 1 has been detected and both exhibit similar immunostimulatory activity (Mui et al., J Pharmacol. Exp. Ther. 298: 1185-1192 (2001)).

Additional specific nucleic acid sequences of oligonucleotides (ODNs) suitable for use in the compositions and methods of the invention are described in U.S. Patent Appln. 60/379,343, U.S. patent application Ser. No. 09/649,527, Int. Publ. WO 02/069369, Int. Publ. No. WO 01/15726, U.S. Pat. No. 6,406,705, and Raney et al., Journal of Pharmacology and Experimental Therapeutics, 298:1185-1192 (2001). In certain embodiments, ODNs used in the compositions and methods of the present invention have a phosphodiester ("PO") backbone or a phosphorothioate ("PS") backbone, and/or at least one methylated cytosine residue in a CpG motif.

Nucleic Acid Modifications

In the 1990's, DNA-based antisense oligodeoxynucleotides (ODN) and ribozymes (RNA) represented an exciting new paradigm for drug design and development, but their application in vivo was prevented by endo- and exo-nuclease activity as well as a lack of successful intracellular delivery. The degradation issue was effectively overcome following extensive research into chemical modifications that prevented the oligonucleotide (oligo) drugs from being recognized by nuclease enzymes but did not inhibit their mechanism of action. This research was so successful that antisense ODN drugs in development today remain intact in vivo for days compared to minutes for unmodified molecules (Kurreck, J. 2003, *Eur J Biochem* 270:1628-44). However, intracellular delivery and mechanism of action issues have so far limited antisense ODN and ribozymes from becoming clinical products.

RNA duplexes are inherently more stable to nucleases than single stranded DNA or RNA, and unlike antisense ODN, unmodified siRNA show good activity once they access the cytoplasm. Even so, the chemical modifications developed to stabilize antisense ODN and ribozymes have also been systematically applied to siRNA to determine how much chemical modification can be tolerated and if pharmacokinetic and pharmacodynamic activity can be enhanced. RNA interference by siRNA duplexes requires an antisense and sense strand, which have different functions. Both are necessary to enable the siRNA to enter RISC, but once loaded the two strands separate and the sense strand is degraded whereas the antisense strand remains to guide RISC to the target mRNA. Entry into RISC is a process that is structurally less stringent than the recognition and cleavage of the target mRNA. Consequently, many different chemical modifications of the sense strand are possible, but only limited changes are tolerated by the antisense strand.

As is known in the art, a nucleoside is a base-sugar combination. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure. Within the oligonucleotide structure, the phosphate groups are commonly referred to as forming the internucleoside backbone of the oligonucleotide. The normal linkage or backbone of RNA and DNA is a 3' to 5' phosphodiester linkage.

The nucleic acid that is used in a lipid-nucleic acid particle according to this invention includes any form of nucleic acid that is known. Thus, the nucleic acid may be a modified nucleic acid of the type used previously to enhance nuclease resistance and serum stability. Surprisingly, however, acceptable therapeutic products can also be prepared using the method of the invention to formulate lipid-nucleic acid particles from nucleic acids that have no modification to the phosphodiester linkages of natural nucleic acid polymers, and the use of unmodified phosphodiester nucleic acids (i.e., nucleic acids in which all of the linkages are phosphodiester linkages) is a preferred embodiment of the invention.

a. Backbone Modifications

Antisense, siRNA, and other oligonucleotides useful in this invention include, but are not limited to, oligonucleotides containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone can also be considered to be oligonucleosides. Modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphoroselenate, methylphosphonate, or O-alkyl phosphotriester linkages, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Particular non-limiting examples of particular modifications that may be present in a nucleic acid according to the present invention are shown in Table 2.

Various salts, mixed salts and free acid forms are also included. Representative United States patents that teach the preparation of the above linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In certain embodiments, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include, e.g., those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that describe the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

The phosphorothioate backbone modification (Table 2, #1), where a non-bridging oxygen in the phosphodiester bond is replaced by sulfur, is one of the earliest and most common means deployed to stabilize nucleic acid drugs against nuclease degradation. In general, it appears that PS modifications can be made extensively to both siRNA strands without much impact on activity (Kurreck, J., *Eur. J. Biochem.* 270:1628-44, 2003). However, PS oligos are known to avidly associate non-specifically with proteins resulting in toxicity, especially upon i.v. administration. Therefore, the PS modification is usually restricted to one or two bases at the 3' and 5' ends. The boranophosphate linker (Table 2, #2) is a recent modification that is apparently more stable than PS, enhances siRNA activity and has low toxicity (Hall et al., *Nucleic Acids Res.* 32:5991-6000, 2004).

TABLE 2

| | | Chemical Modifications Applied to siRNA and Other Nucleic Acids | | |
|---|---|---|---|---|
| # | Abbreviation | Name | Modification Site | Structure |
| 1 | PS | Phosphorothioate | Backbone | 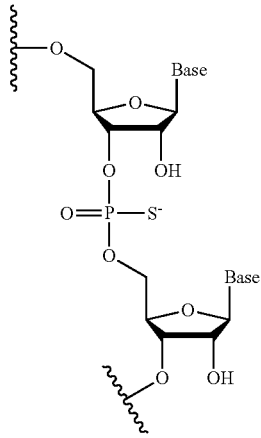 |
| 2 | PB | Boranophosphate | Backbone | 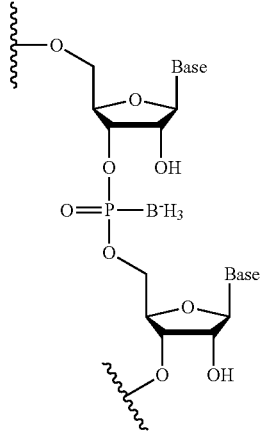 |

TABLE 2-continued

Chemical Modifications Applied to siRNA and Other Nucleic Acids

| # | Abbreviation | Name | Modification Site | Structure |
|---|---|---|---|---|
| 3 | N3-MU | N3-methyl-uridine | Base | 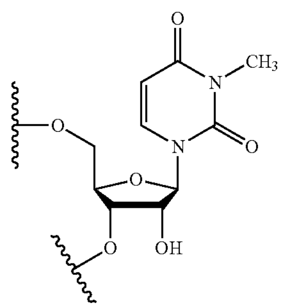 |
| 4 | 5'-BU | 5'-bromo-uracil | Base | 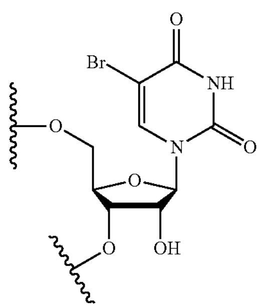 |
| 5 | 5'-IU | 5'-iodo-uracil | Base | 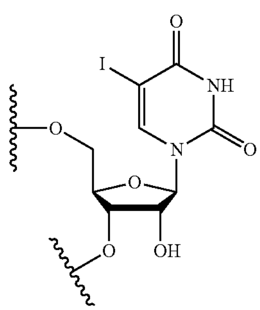 |
| 6 | 2,6-DP | 2,6-diaminopurine | Base | 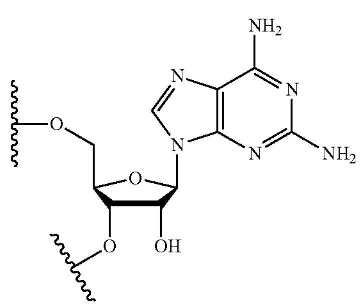 |
| 7 | 2'-F | 2'-Fluoro | Sugar | 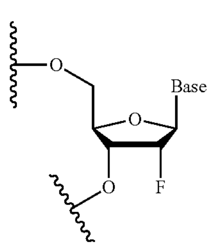 |

TABLE 2-continued

Chemical Modifications Applied to siRNA and Other Nucleic Acids

| # | Abbreviation | Name | Modification Site | Structure |
|---|---|---|---|---|
| 8 | 2'-OME | 2''-O-methyl | Sugar | 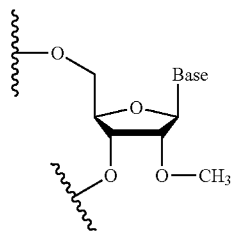 |
| 9 | 2'-O-MOE | 2'-O-(2-methoxylethyl) | Sugar | 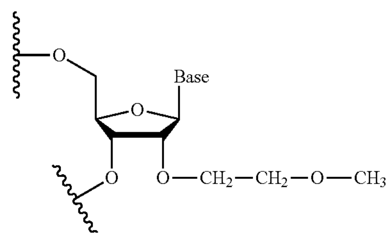 |
| 10 | 2'-DNP | 2'-O-(2,4-dinitrophenyl) | Sugar | 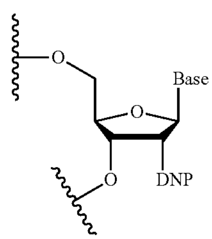 |
| 11 | LNA | Locked Nucleic Acid (methylene bridge connecting the 2'-oxygen with the 4'-carbon of the ribose ring) | Sugar | 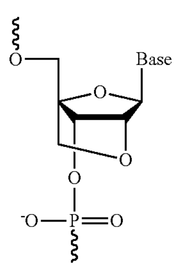 |
| 12 | 2'-Amino | 2'-Amino | Sugar | 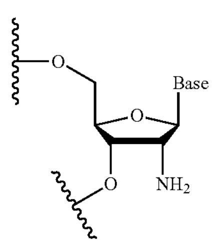 |
| 13 | 2'-Deoxy | 2'-Deoxy | Sugar | 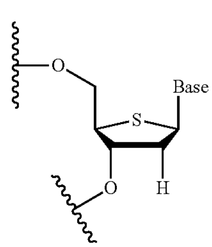 |

TABLE 2-continued

Chemical Modifications Applied to siRNA and Other Nucleic Acids

| # | Abbreviation | Name | Modification Site | Structure |
|---|---|---|---|---|
| 14 | 4'-thio | 4'-thio-ribonucleotide | Sugar | (structure showing 4'-thio ribonucleotide with Base, S, O, OH) |

Other useful nucleic acids derivatives include those nucleic acids molecules in which the bridging oxygen atoms (those forming the phosphoester linkages) have been replaced with —S—, —NH—, —CH2- and the like. In certain embodiments, the alterations to the antisense, siRNA, or other nucleic acids used will not completely affect the negative charges associated with the nucleic acids. Thus, the present invention contemplates the use of antisense, siRNA, and other nucleic acids in which a portion of the linkages are replaced with, for example, the neutral methyl phosphonate or phosphoramidate linkages. When neutral linkages are used, in certain embodiments, less than 80% of the nucleic acid linkages are so substituted, or less than 50% of the linkages are so substituted.

b. Base Modifications

Base modifications are less common than those to the backbone and sugar. The modifications shown in 0.3-6 all appear to stabilize siRNA against nucleases and have little effect on activity (Zhang, H. Y., et al., *Curr Top Med Chem* 6:893-900 (2006)).

Accordingly, oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Certain nucleobases are particularly useful for increasing the binding affinity of the oligomeric compounds of the invention, including 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications* 1993, CRC Press, Boca Raton, pages 276-278). These may be combined, in particular embodiments, with 2'-O-methoxyethyl sugar modifications. United States patents that teach the preparation of certain of these modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

c. Sugar Modifications

Most modifications on the sugar group occur at the 2'-OH of the RNA sugar ring, which provides a convenient chemically reactive site (Manoharan, M., *Curr Opin Chem Biol* 8:570-9 (2004); Zhang, H. Y., et al., *Curr Top Med Chem* 6:893-900 (2006)). The 2'-F and 2'-OME are common and both increase stability, the 2'-OME modification does not reduce activity as long as it is restricted to less than 4 nucleotides per strand (Holen, T., et al., *Nucleic Acids Res* 31:2401-7 (2003)). The 2'-O-MOE is most effective in siRNA when modified bases are restricted to the middle region of the molecule (Prakash, T. P., et al., *J Med Chem* 48:4247-53 (2005)). Other modifications found to stabilize siRNA without loss of activity are shown in Table 2, 10-14.

Modified oligonucleotides may also contain one or more substituted sugar moieties. For example, the invention includes oligonucleotides that comprise one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted $C_1$ to $C_{10}$ alkyl or C2 to C10 alkenyl and alkynyl. Particularly preferred are $O[(CH_2)_nO]_mCH_3$, $O(CH_2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy(2'-O—$CH_2CH_2OCH_3$, also known as 2'-O-(2-methoxyethyl) or 2'-MOE) (Martin et al., *Helv. Chim. Acta* 1995, 78, 486-504), i.e., an alkoxyalkoxy group. Other modifications include 2'-dimethylaminooxyethoxy, i.e., a $O(CH_2)_2ON(CH_3)_2$ group, also known as 2'-DMAOE, and 2'-dimethylaminoethoxyethoxy(2'-DMAEOE).

Additional modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

In other oligonucleotide mimetics, both the sugar and the internucleoside linkage, i.e., the backbone, of the nucleotide units are replaced with novel groups, although the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al., *Science* 254, 1497-1500 (1991).

Particular embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— (referred to as a methylene (methylimino) or MMI backbone) —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester backbone is represented as —O—P—O—CH$_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

d. Chimeric Oligonucleotides

It is not necessary for all positions in a given compound to be uniformly modified, and in fact more than one of the aforementioned modifications may be incorporated in a single compound or even at a single nucleoside within an oligonucleotide. Certain preferred oligonucleotides of this invention are chimeric oligonucleotides. "Chimeric oligonucleotides" or "chimeras," in the context of this invention, are oligonucleotides that contain two or more chemically distinct regions, each made up of at least one nucleotide. These oligonucleotides typically contain at least one region of modified nucleotides that confers one or more beneficial properties (such as, e.g., increased nuclease resistance, increased uptake into cells, increased binding affinity for the RNA target) and a region that is a substrate for RNase H cleavage.

In one embodiment, a chimeric oligonucleotide comprises at least one region modified to increase target binding affinity. Affinity of an oligonucleotide for its target is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In one embodiment, the region of the oligonucleotide which is modified to increase target mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance oligonucleotide inhibition of target gene expression.

In another embodiment, a chimeric oligonucleotide comprises a region that acts as a substrate for RNAse H. Of course, it is understood that oligonucleotides may include any combination of the various modifications described herein Another modification of the oligonucleotides of the invention involves chemically linking to the oligonucleotide one or more moieties or conjugates which enhance the activity, cellular distribution or cellular uptake of the oligonucleotide. Such conjugates and methods of preparing the same are known in the art.

Those skilled in the art will realize that for in vivo utility, such as therapeutic efficacy, a reasonable rule of thumb is that if a thiolated version of the sequence works in the free form, that encapsulated particles of the same sequence, of any chemistry, will also be efficacious. Encapsulated particles may also have a broader range of in vivo utilities, showing efficacy in conditions and models not known to be otherwise responsive to antisense therapy. Those skilled in the art know that applying this invention they may find old models which now respond to antisense therapy. Further, they may revisit discarded antisense sequences or chemistries and find efficacy by employing the invention.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives.

Characteristic of Nucleic Acid-Lipid Particles

In certain embodiments, the present invention relates to methods and compositions for producing lipid-encapsulated nucleic acid particles in which nucleic acids are encapsulated within a lipid layer. Such nucleic acid-lipid particles, incorporating siRNA oligonucleotides, are characterized using a variety of biophysical parameters including: (1) drug to lipid ratio; (2) encapsulation efficiency; and (3) particle size. High drug to lipid rations, high encapsulation efficiency, good nuclease resistance and serum stability and controllable particle size, generally less than 200 nm in diameter are desirable. In addition, the nature of the nucleic acid polymer is of significance, since the modification of nucleic acids in an effort to impart nuclease resistance adds to the cost of therapeutics while in many cases providing only limited resistance. Unless stated otherwise, these criteria are calculated in this specification as follows:

Nucleic acid to lipid ratio is the amount of nucleic acid in a defined volume of preparation divided by the amount of lipid in the same volume. This may be on a mole per mole basis or on a weight per weight basis, or on a weight per mole basis. For final, administration-ready formulations, the nucleic acid:lipid ratio is calculated after dialysis, chromatography and/or enzyme (e.g., nuclease) digestion has been employed to remove as much of the external nucleic acid as possible;

Encapsulation efficiency refers to the drug to lipid ratio of the starting mixture divided by the drug to lipid ratio of the final, administration competent formulation. This is a measure of relative efficiency. For a measure of absolute efficiency, the total amount of nucleic acid added to the starting mixture that ends up in the administration competent formulation, can also be calculated. The amount of lipid lost during the formulation process may also be calculated. Efficiency is a measure of the wastage and expense of the formulation; and Size indicates the size (diameter) of the particles formed. Size distribution may be determined using quasi-elastic light scattering (QELS) on a Nicomp Model 370 sub-micron particle sizer. Particles under 200 nm are preferred for distribution to neo-vascularized (leaky) tissues, such as neoplasms and sites of inflammation.

Pharmaceutical Compositions

The lipid particles of present invention, particularly when associated with a therapeutic agent, may be formulated as a pharmaceutical composition, e.g., which further comprises a pharmaceutically acceptable diluent, excipient, or carrier, such as physiological saline or phosphate buffer, selected in accordance with the route of administration and standard pharmaceutical practice.

In particular embodiments, pharmaceutical compositions comprising the lipid-nucleic acid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.9% saline, 0.3% glycine, and the like, including glycoproteins for enhanced stability, such as albumin, lipoprotein, globulin, etc. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid particle or lipid-nucleic acid particle in the pharmaceutical formulations can vary widely, i.e., from less than about 0.01%, usually at or at least about 0.05-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, the nucleic acid-lipid particles of the invention may include polyethylene glycol (PEG)-modified phospholipids, PEG-ceramide, or ganglioside $G_{M1}$-modified lipids or other lipids effective to prevent or limit aggregation. Addition of such components does not merely prevent complex aggregation. Rather, it may also provide a means for increasing circulation lifetime and increasing the delivery of the lipid-nucleic acid composition to the target tissues.

The present invention also provides lipid-therapeutic agent compositions in kit form. The kit will typically be comprised of a container that is compartmentalized for holding the various elements of the kit. The kit will contain the particles or pharmaceutical compositions of the present invention, preferably in dehydrated or concentrated form, with instructions for their rehydration or dilution and administration. In certain embodiments, the particles comprise the active agent, while in other embodiments, they do not.

D. Methods of Manufacture

The methods and compositions of the invention make use of certain cationic lipids, the synthesis, preparation and characterization of which is described below and in the accompanying Examples. In addition, the present invention provides methods of preparing lipid particles, including those associated with a therapeutic agent, e.g., a nucleic acid. Generally, any method of preparing nucleic acid-lipid particles may be used according to the present invention by using one or more of the lipids of the present invention in the resulting nucleic acid-lipid particles. Examples of suitable methods are known in the art and described, e.g., in U.S. Patent Application Publication No. 2006/0134189.

In one embodiment, a mixture of lipids is combined with a buffered aqueous solution of nucleic acid to produce an intermediate mixture containing nucleic acid encapsulated in lipid particles wherein the encapsulated nucleic acids are present in a nucleic acid/lipid ratio of about 3 wt % to about 25 wt %, preferably 5 to 15 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

As described above, several of these cationic lipids are amino lipids that are charged at a pH below the $pK_a$ of the amino group and substantially neutral at a pH above the $pK_a$. These cationic lipids are termed titratable cationic lipids and can be used in the formulations of the invention using a two-step process. First, lipid vesicles can be formed at the lower pH with titratable cationic lipids and other vesicle components in the presence of nucleic acids. In this manner, the vesicles will encapsulate and entrap the nucleic acids. Second, the surface charge of the newly formed vesicles can be neutralized by increasing the pH of the medium to a level above the $pK_a$ of the titratable cationic lipids present, i.e., to physiological pH or higher. Without intending to be bound by any particular theory, it is believed that the very high efficiency of nucleic acid encapsulation is a result of electrostatic interaction at low pH. At acidic pH (e.g. pH 4.0) the vesicle surface is charged and binds a portion of the nucleic acids through electrostatic interactions. When the external acidic buffer is exchanged for a more neutral buffer (e.g. pH 7.5) the surface of the lipid particle or liposome is neutralized, allowing any external nucleic acid to be removed. More detailed information on the formulation process is provided in various publications (e.g., U.S. Pat. No. 6,287,591 and U.S. Pat. No. 6,858,225). Particularly advantageous aspects of this process include both the facile removal of any surface adsorbed nucleic acid and a resultant nucleic acid delivery vehicle which has a neutral surface. Liposomes or lipid particles having a neutral surface are expected to avoid rapid clearance from circulation and to avoid certain toxicities which are associated with cationic liposome preparations. It is further noted that the vesicles formed in this manner provide formulations of uniform vesicle size with high content of nucleic acids. Additionally, the vesicles have a size range of from about 30 to about 150 nm, more preferably about 30 to about 90 nm. Additional details concerning these uses of such titratable cationic lipids in the formulation of nucleic acid-lipid particles are provided in U.S. Pat. No. 6,287,591 and U.S. Pat. No. 6,858,225, incorporated herein by reference.

In certain embodiments, the mixture of lipids includes at least two lipid components: a first amino lipid component of the present invention that is selected from among lipids which have a pKa such that the lipid is cationic at pH below the pKa and neutral at pH above the pKa, and a second lipid component that is selected from among lipids that prevent particle aggregation during lipid-nucleic acid particle formation. In particular embodiments, the amino lipid is a novel cationic lipid of the present invention.

In certain embodiments of preparing the nucleic acid-lipid particles of the invention, the mixture of lipids is typically a solution of lipids in an organic solvent. This mixture of lipids can then be dried to form a thin film or lyophilized to form a powder before being hydrated with an aqueous buffer to form liposomes. Alternatively, in a preferred method, the lipid mixture can be solubilized in a water miscible alcohol, such as ethanol, and this ethanolic solution added to an aqueous buffer resulting in spontaneous liposome formation. In most embodiments, the alcohol is used in the form in which it is commercially available. For example, ethanol can be used as absolute ethanol (100%), or as 95% ethanol, the remainder being water. This method is described in more detail in U.S. Pat. No. 5,976,567.

In one exemplary embodiment, the mixture of lipids is a mixture of cationic amino lipids, neutral lipids (other than an amino lipid), a sterol (e.g., cholesterol) and a PEG-modified lipid (e.g., a PEG-S-DMG, PEG-C-DOMG or PEG-DMA) in an alcohol solvent. In certain embodiments, the lipid mixture consists essentially of a cationic amino lipid, a neutral lipid, cholesterol and a PEG-modified lipid in alcohol, more preferably ethanol. In certain embodiments, the first solution consists of the above lipid mixture in molar ratios of about 20-70% amino lipid: 5-45% neutral lipid:20-55% cholesterol:0.5-15% PEG-modified lipid. In other embodiments, the first solution consists essentially of DLin-K-C2-DMA, DSPC, Chol and PEG-S-DMG, PEG-C-DOMG or PEG-DMA, more preferably in a molar ratio of about 20-60% DLin-K-C2-DMA: 5-25% DSPC:25-55% Chol:0.5-15% PEG-S-DMG, PEG-C-DOMG or PEG-DMA. In another group of embodiments, the neutral lipid in these compositions is replaced with POPC, DOPE or SM.

In certain embodiments in accordance with the invention, the lipid mixture is combined with a buffered aqueous solution that may contain the nucleic acids. The buffered aqueous solution of is typically a solution in which the buffer has a pH of less than the $pK_a$ of the protonatable lipid in the lipid mixture. Examples of suitable buffers include citrate, phosphate, acetate, and MES. A particularly preferred buffer is citrate buffer. Preferred buffers will be in the range of 1-1000 mM of the anion, depending on the chemistry of the nucleic acid being encapsulated, and optimization of buffer concentration may be significant to achieving high loading levels (see, e.g., U.S. Pat. No. 6,287,591 and U.S. Pat. No. 6,858, 225). Alternatively, pure water acidified to pH 5-6 with chloride, sulfate or the like may be useful. In this case, it may be suitable to add 5% glucose, or another non-ionic solute which will balance the osmotic potential across the particle membrane when the particles are dialyzed to remove ethanol, increase the pH, or mixed with a pharmaceutically acceptable carrier such as normal saline. The amount of nucleic acid in buffer can vary, but will typically be from about 0.01 mg/mL to about 200 mg/mL, more preferably from about 0.5 mg/mL to about 50 mg/mL.

The mixture of lipids and the buffered aqueous solution of therapeutic nucleic acids is combined to provide an intermediate mixture. The intermediate mixture is typically a mixture of lipid particles having encapsulated nucleic acids. Additionally, the intermediate mixture may also contain some portion of nucleic acids which are attached to the surface of the lipid particles (liposomes or lipid vesicles) due to the ionic attraction of the negatively-charged nucleic acids and positively-charged lipids on the lipid particle surface (the amino lipids or other lipid making up the protonatable first lipid component are positively charged in a buffer having a pH of less than the $pK_a$ of the protonatable group on the lipid). In one group of preferred embodiments, the mixture of lipids is an alcohol solution of lipids and the volumes of each of the solutions is adjusted so that upon combination, the resulting alcohol content is from about 20% by volume to about 45% by volume. The method of combining the mixtures can include any of a variety of processes, often depending upon the scale of formulation produced. For example, when the total volume is about 10-20 mL or less, the solutions can be combined in a test tube and stirred together using a vortex mixer. Large-scale processes can be carried out in suitable production scale glassware.

Optionally, the lipid-encapsulated therapeutic agent (e.g., nucleic acid) complexes which are produced by combining the lipid mixture and the buffered aqueous solution of therapeutic agents (nucleic acids) can be sized to achieve a desired size range and relatively narrow distribution of lipid particle sizes. Preferably, the compositions provided herein will be sized to a mean diameter of from about 70 to about 200 nm, more preferably about 90 to about 130 nm. Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size determination. For certain methods herein, extrusion is used to obtain a uniform vesicle size.

Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing.

In particular embodiments, methods of the present invention further comprise a step of neutralizing at least some of the surface charges on the lipid portions of the lipid-nucleic acid compositions. By at least partially neutralizing the surface charges, unencapsulated nucleic acid is freed from the lipid particle surface and can be removed from the composition using conventional techniques. Preferably, unencapsulated and surface adsorbed nucleic acids are removed from the resulting compositions through exchange of buffer solutions. For example, replacement of a citrate buffer (pH about 4.0, used for forming the compositions) with a HEPES-buffered saline (HBS pH about 7.5) solution, results in the neutralization of liposome surface and nucleic acid release from the surface. The released nucleic acid can then be removed via chromatography using standard methods, and then switched into a buffer with a pH above the pKa of the lipid used.

Optionally the lipid vesicles (i.e., lipid particles) can be formed by hydration in an aqueous buffer and sized using any of the methods described above prior to addition of the nucleic acid, according to the preformed vesicle (PFV) method. As described above, the aqueous buffer should be of a pH below the pKa of the amino lipid. A solution of the nucleic acids can then be added to these sized, preformed vesicles. To allow encapsulation of nucleic acids into such "pre-formed" vesicles the mixture should contain an alcohol, such as ethanol. In the case of ethanol, it should be present at a concentration of about 20% (w/w) to about 45% (w/w). In addition, it may be necessary to warm the mixture of pre-formed vesicles and nucleic acid in the aqueous buffer-ethanol mixture to a temperature of about 25° C. to about 50° C. depending on the composition of the lipid vesicles and the nature of the nucleic acid. It will be apparent to one of ordinary skill in the art that optimization of the encapsulation process to achieve a desired level of nucleic acid in the lipid vesicles will require manipulation of variable such as ethanol concentration and temperature. Examples of suitable conditions for nucleic acid encapsulation are provided in the Examples. Once the nucleic acids are encapsulated within the preformed vesicles, the external pH can be increased to at least partially neutralize the surface charge. Unencapsulated and surface adsorbed nucleic acids can then be removed as described above.

In other embodiments, nucleic acid lipid particles are prepared via a continuous mixing method, e.g., a process that includes providing an aqueous solution comprising a nucleic acid such as an siRNA, in a first reservoir, and providing an organic lipid solution in a second reservoir, and mixing the aqueous solution with the organic lipid solution such that the organic solution mixes with the aqueous solution so as to substantially instantaneously produce a liposome encapsulating the nucleic acid. This process and the apparatus for carrying out this process are described in detail in U.S. Patent Application Publication No. 2004/0142025.

In another embodiment, nucleic acid lipid particles are produced via a direct dilution process that includes forming a liposome solution and immediately and directly introducing the liposome solution to a collection vessel containing a controlled amount of dilution buffer. In certain embodiments, the collection vessel includes one or more elements configured to stir the contents of the collection vessel to facilitate dilution. In other embodiment, a third reservoir containing dilution buffer is fluidly coupled to a second mixing region. In this embodiment, t liposome solution formed in the first mixing region is immediately and directly mixed with the dilution buffer in the second mixing region. Processes and apparati for carrying out these direct dilution methods are described in further detail in U.S. Patent Application Publication No. 2007/0042031.

E. Method of Use

The lipid particles of the present invention may be used to deliver a therapeutic agent to a cell, in vitro or in vivo. In particular embodiments, the therapeutic agent is a nucleic acid, which is delivered to a cell using a nucleic acid-lipid particles of the present invention. While the following description of various methods of using the lipid particles and related pharmaceutical compositions of the present invention are exemplified by description related to nucleic acid-lipid particles, it is understood that these methods and compositions may be readily adapted for the delivery of any therapeutic agent for the treatment of any disease or disorder that would benefit from such treatment.

In certain embodiments, the present invention provides methods for introducing a nucleic acid into a cell. Preferred nucleic acids for introduction into cells are siRNA, immune-stimulating oligonucleotides, plasmids, antisense oligonucleotides, and ribozymes. These methods may be carried out by contacting the particles or compositions of the present invention with the cells for a period of time sufficient for intracellular delivery to occur.

The compositions of the present invention can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited with respect to the scope of the invention, it is believed that in the case of particles taken up into the cell by endocytosis the particles then interact with the endosomal membrane, resulting in destabilization of the endosomal membrane, possibly by the formation of non-bilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between about 1 μmol and about 10 mmol. In certain embodiments, treatment of the cells with the lipid-nucleic acid compositions will generally be carried out at physiological temperatures (about 37° C.) for periods of time from about 1 to 24 hours, preferably from about 2 to 8 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of embodiments, a lipid-nucleic acid particle suspension is added to 60-80% confluent plated cells having a cell density of from about $10^3$ to about $10^5$ cells/mL, more preferably about $2\times10^4$ cells/mL. The concentration of the suspension added to the cells is preferably of from about 0.01 to 20 µg/mL, more preferably about 1 µg/mL.

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630-643 (1989), and for cystic fibrosis, see Goodfellow, *Nature* 341:102-103 (1989)). Other uses for the compositions of the present invention include introduction of antisense oligonucleotides in cells (see, Bennett, et al., *Mol. Pharm.* 41:1023-1033 (1992)).

Alternatively, the compositions of the present invention can also be used for deliver of nucleic acids to cells in vivo, using methods which are known to those of skill in the art. With respect to application of the invention for delivery of DNA or mRNA sequences, Zhu, et al., *Science* 261:209-211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250-256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278-281 (1989), incorporated herein by reference, describes the in vivo transfection of lungs of mice with a functioning prokaryotic gene encoding the intracellular enzyme, chloramphenicol acetyltransferase (CAT). Thus, the compositions of the invention can be used in the treatment of infectious diseases.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection. For one example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512-527 (1983); Mannino, et al., *Biotechniques* 6:682-690 (1988); Nicolau, et al., *Crit. Rev. Ther. Drug Carrier Syst.* 6:239-271 (1989), and Behr, *Acc. Chem. Res.* 26:274-278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs (see, Brigham, at al., *Am. J. Sci.* 298(4):278-281 (1989)) or by direct injection at the site of disease (Culver, Human Gene Therapy, MaryAnn Liebert, Inc., Publishers, New York. pp. 70-71 (1994)).

The methods of the present invention may be practiced in a variety of hosts. Preferred hosts include mammalian species, such as humans, non-human primates, dogs, cats, cattle, horses, sheep, and the like.

Dosages for the lipid-therapeutic agent particles of the present invention will depend on the ratio of therapeutic agent to lipid and the administrating physician's opinion based on age, weight, and condition of the patient.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least 10%, 20%, 30%, 40%, 50%, or greater than 50% as compared to an appropriate control value.

For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polynucleotide that encodes the target polypeptide, thereby disrupting expression of the target polynucleotide or polypeptide. Alternatively, the nucleic acid may be a plasmid that expresses such an antisense oligonucleotide, siRNA, or microRNA.

In one particular embodiment, the present invention provides a method of modulating the expression of a polypeptide by a cell, comprising providing to a cell a lipid particle that consists of or consists essentially of DLin-K-C2-DMA, DSPC, Chol and PEG-S-DMG, PEG-C-DOMG or PEG-DMA, e.g., in a molar ratio of about 20-60% DLin-K-C2-DMA: 5-25% DSPC:25-55% Chol:0.5-15% PEG-S-DMG, PEG-C-DOMG or PEG-DMA, wherein the lipid particle is associated with a nucleic acid capable of modulating the expression of the polypeptide. In particular embodiments, the molar lipid ratio is approximately 40/10/40/10 (mol % DLin-K-C2-DMA/DSPC/Chol/PEG-S-DMG). In another group of embodiments, the neutral lipid in these compositions is replaced with POPC, DOPE or SM. In other embodiments, the cationic lipid is replaced with DLin-K²-DMA or DLin-K6-DMA.

In particular embodiments, the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In one embodiment, the pharmaceutical composition comprises a lipid particle that consists of or consists essentially of DLin-K-C2-DMA, DSPC, Chol and PEG-S-DMG, PEG-C-DOMG or PEG-DMA, e.g., in a molar ratio of about 20-60% DLin-K-C2-DMA: 5-25% DSPC:25-55% Chol:0.5-15% PEG-S-DMG, PEG-C-DOMG or PEG-DMA, wherein the lipid particle is associated with the therapeutic nucleic acid. In particular embodiments, the molar lipid ratio is approximately 40/10/40/10 (mol % DLin-K-C2-DMA/DSPC/Chol/PEG-S-DMG). In another group of embodiments, the neutral lipid in these compositions is replaced with POPC, DOPE or SM. In other embodiments, the cationic lipid is replaced with DLin-K²-DMA or DLin-K6-DMA.

In another related embodiment, the present invention includes a method of treating a disease or disorder characterized by underexpression of a polypeptide in a subject, comprising providing to the subject a pharmaceutical composition of the present invention, wherein the therapeutic agent is a plasmid that encodes the polypeptide or a functional variant or fragment thereof.

In one embodiment, the pharmaceutical composition comprises a lipid particle that consists of or consists essentially of DLin-K-C2-DMA, DSPC, Chol and PEG-S-DMG, PEG-C-DOMG or PEG-DMA, e.g., in a molar ratio of about 20-60% DLin-K-C2-DMA: 5-25% DSPC:25-55% Chol:0.5-15% PEG-S-DMG or PEG-DMA, wherein the lipid particle is associated with the therapeutic nucleic acid. In particular embodiments, the molar lipid ratio is approximately 40/10/40/10 (mol % DLin-K-C2-DMA/DSPC/Chol/PEG-S-DMG). In another group of embodiments, the neutral lipid in these compositions is replaced with POPC, DOPE or SM. In other embodiments, the cationic lipid is replaced with DLin-K²-DMA or DLin-K6-DMA.

The present invention further provides a method of inducing an immune response in a subject, comprising providing to the subject the pharmaceutical composition of the present invention, wherein the therapeutic agent is an immunostimulatory oligonucleotide. In certain embodiments, the immune response is a humoral or mucosal immune response. In one embodiment, the pharmaceutical composition comprises a lipid particle that consists of or consists essentially of DLin-K-C2-DMA, DSPC, Chol and PEG-S-DMG, PEG-C-DOMG or PEG-DMA, e.g., in a molar ratio of about 20-60% DLin-K-C2-DMA: 5-25% DSPC:25-55% Chol:0.5-15% PEG-S-DMG, PEG-C-DOMG or PEG-DMA, wherein the lipid particle is associated with the therapeutic nucleic acid. In particular embodiments, the molar lipid ratio is approximately 40/10/40/10 (mol % DLin-K-C2-DMA/DSPC/Chol/PEG-S-DMG, PEG-C-DOMG or PEG-DMA). In another group of embodiments, the neutral lipid in these compositions is replaced with POPC, DOPE or SM. In other embodiments, the cationic lipid is replaced with DLin-K²-DMA or DLin-K6-DMA.

In further embodiments, the pharmaceutical composition is provided to the subject in combination with a vaccine or antigen. Thus, the present invention itself provides vaccines comprising a lipid particle of the present invention, which comprises an immunostimulatory oligonucleotide, and is also associated with an antigen to which an immune response is desired. In particular embodiments, the antigen is a tumor antigen or is associated with an infective agent, such as, e.g., a virus, bacteria, or parasite.

A variety of tumor antigens, infections agent antigens, and antigens associated with other disease are well known in the art and examples of these are described in references cited herein. Examples of antigens suitable for use in the present invention include, but are not limited to, polypeptide antigens and DNA antigens. Specific examples of antigens are Hepatitis A, Hepatitis B, small pox, polio, anthrax, influenza, typhus, tetanus, measles, rotavirus, diphtheria, pertussis, tuberculosis, and rubella antigens. In a preferred embodiment, the antigen is a Hepatitis B recombinant antigen. In other aspects, the antigen is a Hepatitis A recombinant antigen. In another aspect, the antigen is a tumor antigen. Examples of such tumor-associated antigens are MUC-1, EBV antigen and antigens associated with Burkitt's lymphoma. In a further aspect, the antigen is a tyrosinase-related protein tumor antigen recombinant antigen. Those of skill in the art will know of other antigens suitable for use in the present invention.

Tumor-associated antigens suitable for use in the subject invention include both mutated and non-mutated molecules that may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Pathogens include, but are not limited to, infectious agents, e.g., viruses, that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Also, gram negative and gram positive bacteria serve as antigens in vertebrate animals. Such gram positive bacteria include, but are not limited to Pasteurella species, Staphylococci species, and Streptococcus species. Gram negative bacteria include, but are not limited to, Escherichia coli, Pseudomonas species, and Salmonella species. Specific examples of infectious bacteria include but are not limited to: Helicobacterpyloris, Borelia burgdorferi, Legionella pneumophilia, Mycobacteria sps (e.g., M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes (Group A Streptococcus), Streptococcus agalactiae (Group B Streptococcus), Streptococcus (viridans group), Streptococcus faecalis, Streptococcus bovis, Streptococcus (anaerobic sps.), Streptococcus pneumoniae, pathogenic Campylobacter sp., Enterococcus sp., Haemophilus influenzae, Bacillus antracis, corynebacterium diphtheriae, corynebacterium sp., Erysipelothrix rhusiopathiae, Clostridium perfringers, Clostridium tetani, Enterobacter aerogenes, Klebsiella pneumoniae, Pasturella multocida, Bacteroides sp., Fusobacterium nucleatum, Streptobacillus moniliformis, Treponema pallidium, Treponema pertenue, Leptospira, Rickettsia, and Actinomyces israelii.

Additional examples of pathogens include, but are not limited to, infectious fungi that infect mammals, and more particularly humans. Examples of infectious fungi include, but are not limited to: Cryptococcus neoformans, Histoplasma capsulatum, Coccidioides immitis, Blastomyces dermatitidis, Chlamydia trachomatis, Candida albicans. Examples of infectious parasites include Plasmodium such as Plasmodium falciparum, Plasmodium malariae, Plasmodium ovale, and Plasmodium vivax. Other infectious organisms (i.e., protists) include Toxoplasma gondii.

EXAMPLES

Example 1

Synthesis of 2,2-Dilinoleyl-4-Dimethylaminomethyl-[1,3]-Dioxolane (DLin-K-DMA)

DLin-K-DMA was synthesized as shown in the following schematic and described below.

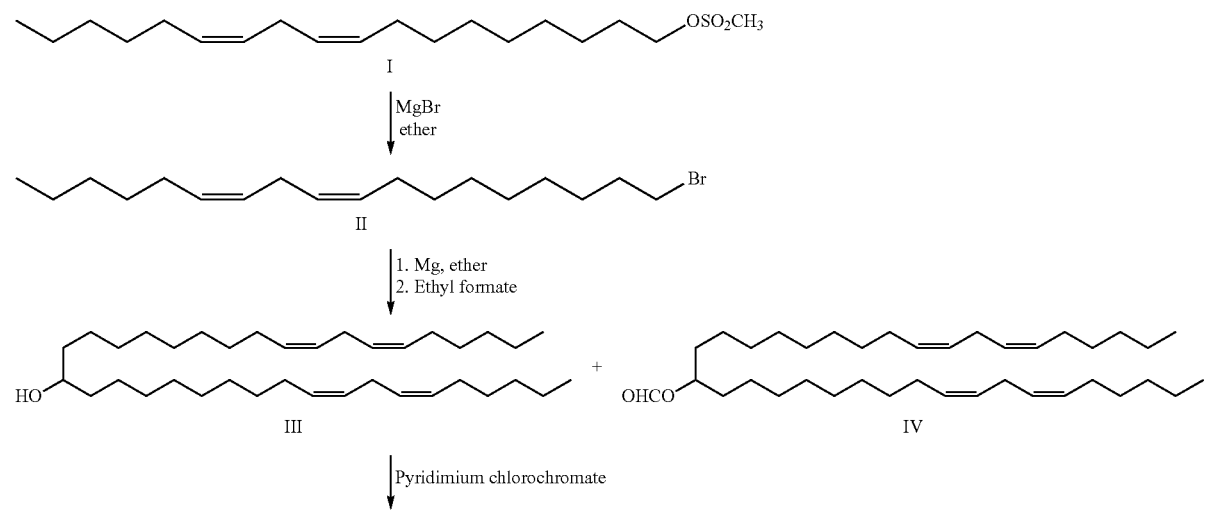

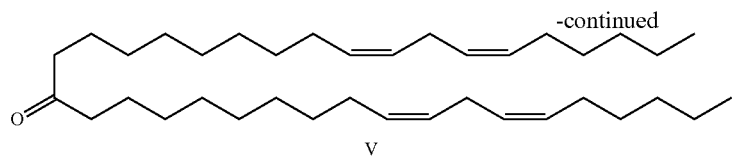

V

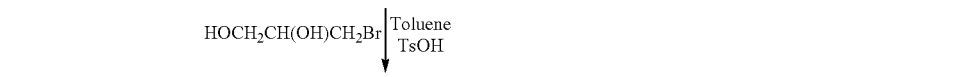

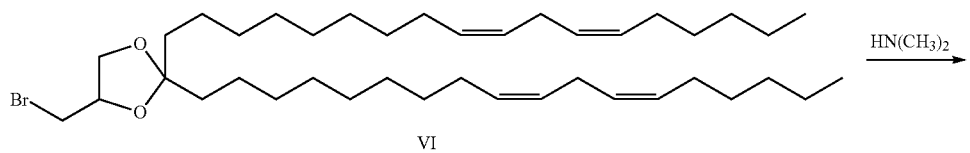

VI

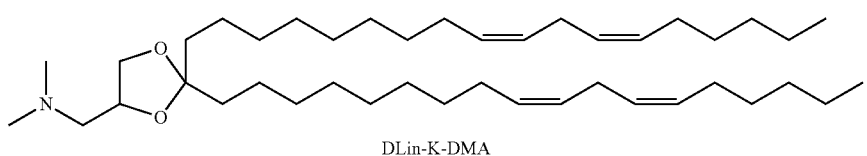

DLin-K-DMA

Synthesis of Linoleyl Bromide (II)

A mixture of linoleyl methane sulfonate (6.2 g, 18 mmol) and magnesium bromide etherate (17 g, 55 mmol) in anhydrous ether (300 mL) was stirred under argon overnight (21 hours). The resulting suspension was poured into 300 mL of chilled water. Upon shaking, the organic phase was separated. The aqueous phase was extracted with ether (2×150 mL). The combined ether phase was washed with water (2×150 mL), brine (150 mL), and dried over anhydrous $Na_2SO_4$. The solvent was evaporated to afford 6.5 g of colourless oil. The crude product was purified by column chromatography on silica gel (230-400 mesh, 300 mL) and eluted with hexanes. This gave 6.2 g (approximately 100%) of linoleyl bromide (II). $^1H$ NMR (400 MHz, CDCl3) δ: 5.27-5.45 (4H, m, 2×CH=CH), 3.42 (2H, t, CH2Br), 2.79 (2H, t, C=C—CH2-C=C), 2.06 (4H, q, 2×allylic CH2), 1.87 (2H, quintet, CH2), 1.2-1.5 (16H, m), 0.90 (3H, t, CH3) ppm.

Synthesis of Dilinoleyl Methanol (III)

To a suspension of Mg turnings (0.45 g, 18.7 mmol) with one crystal of iodine in 200 mL of anhydrous ether under nitrogen was added a solution of linoleyl bromide (II) in 50 mL of anhydrous ether at room temperature. The resulting mixture was refluxed under nitrogen overnight. The mixture was cooled to room temperature. To the cloudy mixture under nitrogen was added dropwise at room temperature a solution of ethyl formate (0.65 g, 18.7 mmol) in 30 mL of anhydrous ether. Upon addition, the mixture was stirred at room temperature overnight (20 hours). The ether layer was washed with 10% $H_2SO_4$ aqueous solution (100 mL), water (2×100 mL), brine (150 mL), and then dried over anhydrous $Na_2SO_4$. Evaporation of the solvent gave 5.0 g of pale oil. Column chromatography on silica gel (230-400 mesh, 300 mL) with 0-7% ether gradient in hexanes as eluent afforded two products, dilinoleyl methanol (2.0 g, III) and dilinoleylmethyl formate (1.4 g, IV). $^1H$ NMR (400 MHz, CDCl3) for dilinoleylmethyl formate (IV) δ: 8.10 (1H, s, CHO), 5.27-5.45 (8H, m, 4×CH=CH), 4.99 (1H, quintet, OCH), 2.78 (4H, t, 2×C=C—CH2-C=C), 2.06 (8H, q, 4×allylic CH2), 1.5-1.6 (4H, m, 2×CH2), 1.2-1.5 (32H, m), 0.90 (6H, t, 2×CH3) ppm.

Dilinoleylmethyl formate (IV, 1.4 g) and KOH (0.2 g) were stirred in 85% EtOH at room temperature under nitrogen overnight. Upon completion of the reaction, half of the solvent was evaporated. The resulting mixture was poured into 150 mL of 5% HCL solution. The aqueous phase was extracted with ether (3×100 ml). The combined ether extract was washed with water (2×100 mL), brine (100 mL), and dried over anhydrous Na2SO4. Evaporation of the solvent gave 1.0 g of dilinoleyl methanol (III) as colourless oil. Overall, 3.0 g (60%) of dilinoleyl methanol (III) were afforded. 1H NMR (400 MHz, CDCl3) for dilinoleyl methanol (III) δ: ppm.

Synthesis of Dilinoleyl Ketone (V)

To a mixture of dilinoleyl methanol (2.0 g, 3.8 mmol) and anhydrous sodium carbonate (0.2 g) in 100 mL of $CH_2Cl_2$ was added pydimium chlorochromate (PCC, 2.0 g, 9.5 mmol). The resulting suspension was stirred at room temperature for 60 min. Ether (300 mL) was then added into the mixture, and the resulting brown suspension was filtered through a pad of silica gel (300 mL). The silica gel pad was further washed with ether (3×200 mL). The ether filtrate and washes were combined. Evaporation of the solvent gave 3.0 g of an oily residual as a crude product. The crude product was purified by column chromatography on silica gel (230-400 mesh, 250 mL) eluted with 0-3% ether in hexanes. This gave 1.8 g (90%) of dilinoleyl ketone (V). $^1$H NMR (400 MHz, CDCl3) δ: 5.25-5.45 (8H, m, 4×CH=CH), 2.78 (4H, t, 2×C=C—CH2-C=C), 2.39 (4H, t, 2×COCH2), 2.05 (8H, q, 4×allylic CH2), 1.45-1.7 (4H, m), 1.2-1.45 (32H, m), 0.90 (6H, t, 2×CH3) ppm.

Synthesis of 2,2-Dilinoleyl-4-bromomethyl-[1,3]-dioxolane (VI)

A mixture of dilinoleyl methanol (V, 1.3 g, 2.5 mmol), 3-bromo-1,2-propanediol (1.5 g, 9.7 mmol) and p-toluene sulfonic acid hydrate (0.16 g, 0.84 mmol) in 200 mL of toluene was refluxed under nitrogen for 3 days with a Dean-Stark tube to remove water. The resulting mixture was cooled to room temperature. The organic phase was washed with water (2×50 mL), brine (50 mL), and dried over anhydrous $Na_2SO_4$. Evaporation of the solvent resulted in a yellowish oily residue. Column chromatography on silica gel (230-400 mesh, 100 mL) with 0-6% ether gradient in hexanes as eluent afforded 0.1 g of pure VI and 1.3 g of a mixture of VI and the starting material. 1H NMR (400 MHz, CDCl3) δ: 5.27-5.45 (8H, m, 4×CH=CH), 4.28-4.38 (1H, m, OCH), 4.15 (1H, dd, OCH), 3.80 (1H, dd, OCH), 3.47 (1H, dd, CHBr), 3.30 (1H, dd, CHBr), 2.78 (4H, t, 2×C=C—CH2-C=C), 2.06 (8H, q, 4×allylic CH2), 1.52-1.68 (4H, m, 2×CH2), 1.22-1.45 (32H, m), 0.86-0.94 (6H, m, 2×CH3) ppm.

Synthesis of 2,2-Dilinoleyl-4-dimethylaminomethyl-[1,3]-dioxolane (DLin-K-DMA)

Anhydrous dimethyl amine was bubbled into an anhydrous THF solution (100 mL) containing 1.3 g of a mixture of 2,2-dilinoleyl-4-bromomethyl-[1,3]-dioxolane (VI) and dilinoleyl ketone (V) at 0° C. for 10 min. The reaction flask was then sealed and the mixture stirred at room temperature for 6 days. Evaporation of the solvent left 1.5 g of a residual. The crude product was purified by column chromatography on silica gel (230-400 mesh, 100 mL) and eluted with 0-5% methanol gradient in dichloromethane. This gave 0.8 g of the desired product DLin-K-DMA. $^1$H NMR (400 MHz, CDCl3) δ: 5.25-5.45 (8, m, 4×CH=CH), 4.28-4.4 (1H, m, OCH), 4.1 (1H, dd, OCH), 3.53 (1H, t OCH), 2.78 (4H, t, 2×C=C—CH2-C=C), 2.5-2.65 (2H, m, NCH2), 2.41 (6H, s, 2×NCH3), 2.06 (8H, q, 4×allylic CH2), 1.56-1.68 (4H, m, 2×CH2), 1.22-1.45 (32H, m), 0.90 (6H, t, 2×CH3) ppm.

Example 2

Synthesis of 1,2-Dilinoleyloxy-N,N-Dimethyl-3-Aminopropane (DLinDMA) DLinDMA was Synthesized as Described Below To a suspension of NaH (95%, 5.2 g, 0.206 mol) in 120 mL of anhydrous benzene was added dropwise N,N-dimethyl-3-aminopropane-1,2-diol (2.8 g, 0.0235 mol) in 40 mL of anhydrous benzene under argon. Upon addition, the resulting mixture was stirred at room temperature for 15 min. Linoleyl methane sulfonate (99%, 20 g, 0.058 mol) in 75 mL of anhydrous benzene was added dropwise at room temperature under argon to the above mixture. After stirred at room temperature for 30 min., the mixture was refluxed overnight under argon. Upon cooling, the resulting suspension was treated dropwise with 250 mL of 1:1 (V:V) ethanol-benzene solution. The organic phase was washed with water (150 mL), brine (2×200 mL), and dried over anhydrous sodium sulfate. Solvent was evaporated in vacuo to afford 17.9 g of light oil as a crude product. 10.4 g of pure DLinDMA were obtained upon purification of the crude product by column chromatography twice on silica gel using 0-5% methanol gradient in methylene chloride. $^1$H NMR (400 MHz, CDCl3) δ: 5.35 (8H, m, CH=CH), 3.5 (7H, m, OCH), 2.75 (4H, t, 2×CH2), 2.42 (2H, m, NCH2), 2.28 (6H, s, 2×NCH3), 2.05 (8H, q, vinyl CH2), 1.56 (4H, m, 2×CH2), 1.28 (32H, m, 16×CH2), 0.88 (6H, t, 2×CH3) ppm.

Example 3

Synthesis of 2,2-Dilinoleyl-4-(2-Dimethylaminoethyl)[1,3]-Dioxolane (DLin-K-C2-DMA)

DLin-K-C2-DMA was synthesized as shown in the schematic diagram and description below.

Synthesis of 2,2-Dilinoleyl-4-(2-hydroxyethyl)-[1,3]-dioxolane (II)

A mixture of dilinoleyl ketone (I, previously prepared as described in Example 1, 527 mg, 1.0 mmol), 1,3,4-butanetriol (technical grade, ca. 90%, 236 mg, 2 mmol) and pyridinium p-toluenesulfonate (50 mg, 0.2 mmol) in 50 mL of toluene was refluxed under nitrogen overnight with a Dean-Stark tube to remove water. The resulting mixture was cooled to room temperature. The organic phase was washed with water (2×30 mL), brine (50 mL), and dried over anhydrous $Na_2SO_4$. Evaporation of the solvent resulted in a yellowish oily residual (0.6 g). The crude product was purified by column chromatography on silica gel (230-400 mesh, 100 mL) with dichloromethane as eluent. This afforded 0.5 g of pure II as colourless oil. $^1$H NMR (400 MHz, CDCl$_3$) δ: 5.25-5.48 (8H, m, 4×CH=CH), 4.18-4.22 (1H, m, OCH), 4.08 (1H, dd, OCH), 3.82 (2H, t, OCH$_2$), 3.53 (1H, t, OCH), 2.78 (4H, t, 2×C=C—CH$_2$—C=C), 2.06 (8H, q, 4×allylic CH$_2$), 1.77-1.93 (2H, m, CH$_2$), 1.52-1.68 (4H, m, 2×CH$_2$), 1.22-1.45 (32H, m), 0.86-0.94 (6H, t, 2×CH$_3$) ppm.

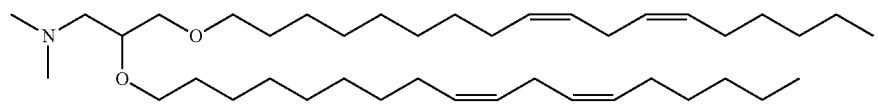

1,2-Dilinoleyloxy-3-dimethylaminopropane (DLinDMA)

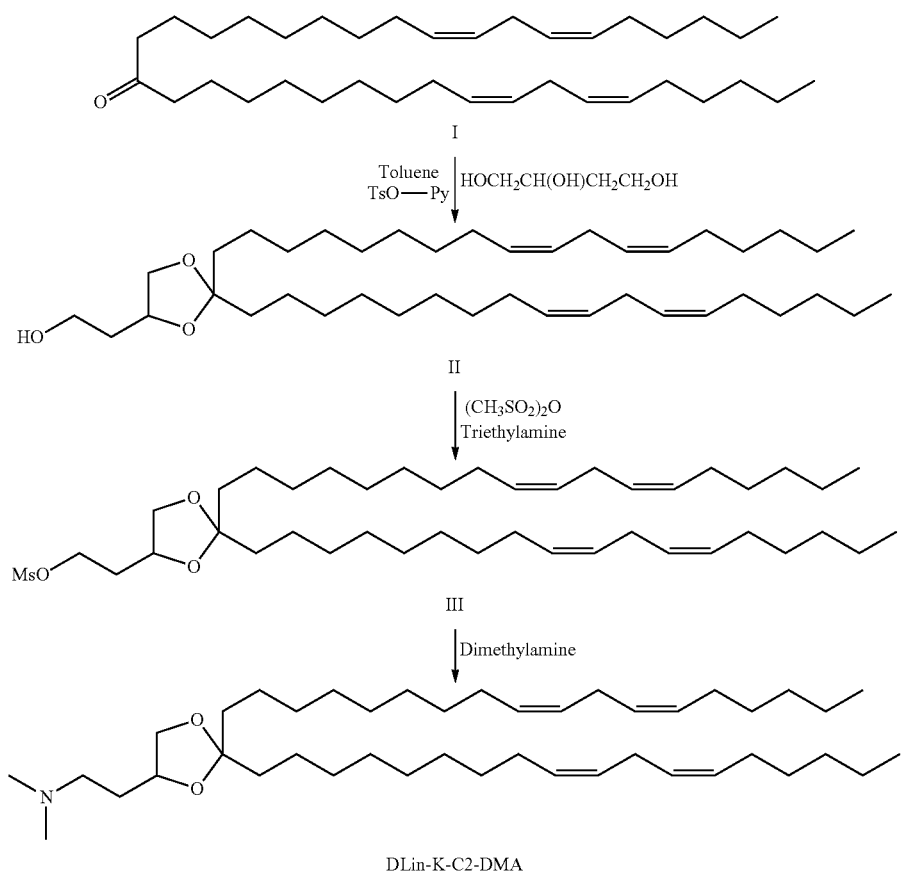

Synthesis of 2,2-Dilinoleyl-4-(2-methanesulfonyl-ethyl)[1,3]-dioxolane (III)

To a solution of 2,2-dilinoleyl-4-(2-hydroxyethyl)-[1,3]-dioxolane (II, 500 mg, 0.81 mmol) and dry triethylamine (218 mg, 2.8 mmol) in 50 mL of anhydrous $CH_2Cl_2$ was added methanesulfonyl anhydride (290 mg, 1.6 mmol) under nitrogen. The resulting mixture was stirred at room temperature overnight. The mixture was diluted with 25 mL of $CH_2Cl_2$. The organic phase was washed with water (2×30 mL), brine (50 mL), and dried over anhydrous $Na_2SO_4$. The solvent was evaporated to afford 510 mg of yellowish oil. The crude product was used in the following step without further purification.

Synthesis of 2,2-Dilinoleyl-4-(2-dimethylaminoethyl)-[1,3]-dioxolane (DLin-K-C2-DMA)

To the above crude material (III) under nitrogen was added 20 mL of dimethylamine in THF (2.0 M). The resulting mixture was stirred at room temperature for 6 days. An oily residual was obtained upon evaporation of the solvent. Column chromatography on silica gel (230-400 mesh, 100 mL) with 0-5% methanol gradient in dichloromethane as eluent resulted in 380 mg of the product DLin-K-C2-DMA as pale oil. $^1H$ NMR (400 MHz, $CDCl_3$) δ: 5.27-5.49 (8, m, 4×CH═CH), 4.01-4.15 (2H, m, 2×OCH), 3.49 (1H, t OCH), 2.78 (4H, t, 2×C═C—$CH_2$—C═C), 2.34-2.54 (2H, m, $NCH_2$), 2.30 (6H, s, 2×$NCH_3$), 2.06 (8H, q, 4×allylic $CH_2$), 1.67-1.95 (2H, m, $CH_2$), 1.54-1.65 (4H, m, 2×$CH_2$), 1.22-1.45 (32H, m), 0.90 (6H, t, 2×$CH_3$) ppm.

Example 4

Synthesis of 2,2-Dilinoleyl-4-(3-Dimethylaminopropyl)[1,3]-Dioxolane (DLin-K-C3-DMA)

DLin-K-C3-DMA was synthesized as described and shown in the schematic diagram below.

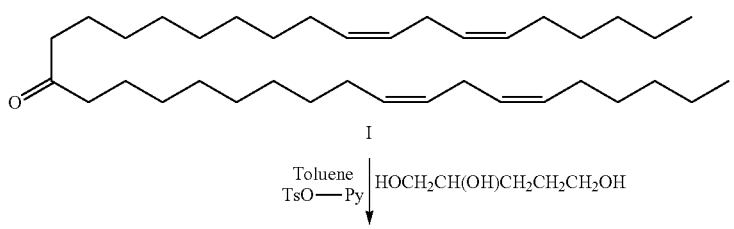

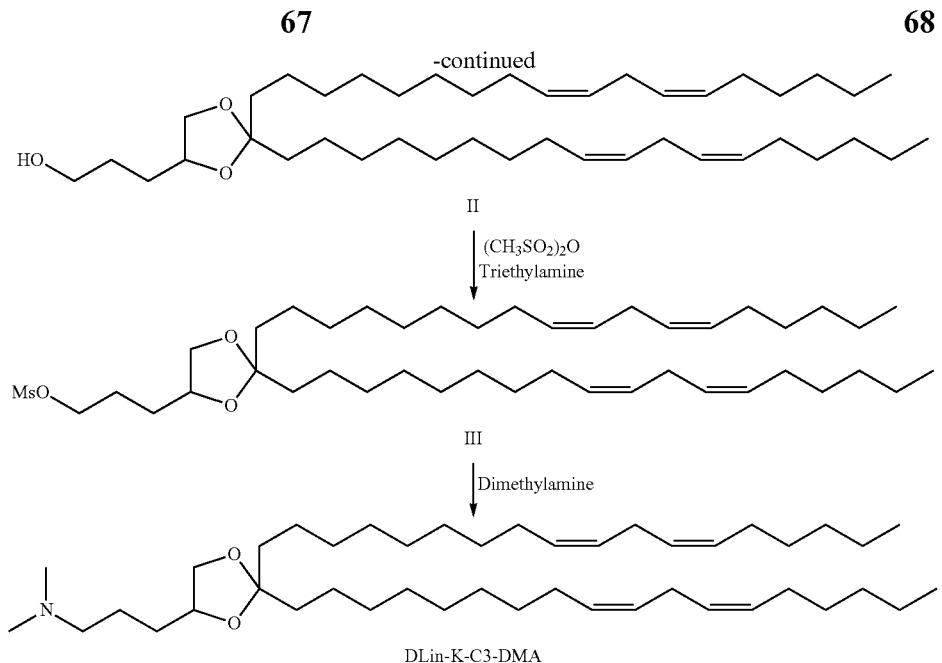

DLin-K-C3-DMA

Synthesis of 1,2,5-Pentanetriol

To a suspension of LiAlH$_4$ (1.75 g) in 80 mL of anhydrous THF was added dropwise under nitrogen a solution of (R)-γ-hydroxymethyl-γ-butarolactone (0.50 g, 4 mmol) in 20 mL of anhydrous THF. The resulting suspension was stirred at room temperature under nitrogen overnight. To this mixture was added 5.5 mL of NaCl-saturated aqueous solution very slowly with use of an ice-water bath. The mixture was further stirred under nitrogen overnight. The white solid was filtered and washed with THF (2×20 mL). The filtrate and washes were combined. Evaporation of the solvent gave 0.25 g of colourless oil as a crude product. The crude product was used in the next step without further purification.

Synthesis of 2,2-Dilinoleyl-4-(3-hydroxypropyl)-[1,3]-dioxolane (II)

A mixture of dilinoleyl ketone (I, previously prepared as described in Example 1, 1.0 g, 2 mmol), 1,2,5-pentanetriol (crude, 0.25 g, 2 mmol) and pyridinium p-toluenesulfonate (100 mg, 0.4 mmol) in 150 mL of toluene was refluxed under nitrogen overnight with a Dean-Stark tube to remove water. The resulting mixture was cooled to room temperature. The organic phase was washed with water (3×40 mL), brine (50 mL), and dried over anhydrous Na$_2$SO$_4$. Evaporation of the solvent gave a yellowish oily residual (1.1 g). The crude product was purified by column chromatography on silica gel (230-400 mesh, 100 mL) with 0-1% methanol in dichloromethane as eluent. This afforded 0.90 g of pure II as colourless oil.

Synthesis of 2,2-Dilinoleyl-4-(3-methanesulfonylpropyl)-[1,3]-dioxolane (III)

To a solution of 2,2-dilinoleyl-4-(3-hydroxypropyl)[1,3]-dioxolane (II, 0.90 g, 1.4 mmol) and dry triethylamine (0.51 g, 5 mmol) in 100 mL of anhydrous CH$_2$Cl$_2$ was added methanesulfonyl anhydride (0.70 g, 4 mmol) under nitrogen. The resulting mixture was stirred at room temperature overnight. The organic phase was washed with water (2×40 mL), brine (50 mL), and dried over anhydrous Na$_2$SO$_4$. The solvent was evaporated to afford 1.0 g of brownish oil as a crude product. The crude product was used in the following step without further purification.

Synthesis of 2,2-Dilinoleyl-4-(3-dimethylaminopropyl)[1,3]-dioxolane (DLin-K-C3-DMA To the above crude material (III, 1.0 g) under nitrogen was added 40 mL of dimethylamine in THF (2.0 M). The resulting mixture was stirred at room temperature for 8 days. The solid was filtered. Upon evaporation of the solvent, an orange residual was resulted. Column chromatography on silica gel (230-400 mesh, 100 mL) with 0-40% ethyl acetate gradient in hexanes as eluent resulted in 510 g of the product DLin-K-C3-DMA as pale oil. $^1$H NMR (400 MHz, CDCl$_3$) δ: 5.22-5.50 (8, m, 4×CH=CH), 3.95-4.15 (2H, m, 2×OCH), 3.35-3.55 (1H, m OCH), 2.78 (4H, t, 2×C=C—CH$_2$—C=C), 2.45-2.55 (2H, m, NCH$_2$), 2.35 (6H, s, 2×NCH$_3$), 2.05 (8H, q, 4×allylic CH$_2$), 1.45-1.75 (6H, m, CH$_2$), 1.2-1.45 (32H, m), 0.90 (6H, t, 2×CH$_3$) ppm.

Example 5

Synthesis of 2,2-Dilinoleyl-4-(4-Dimethylaminobutyl)-[1,3]-Dioxolane (DLin-K-C4-DMA)

DLin-K-C4-DMA was synthesized as described and shown in the schematic diagram below.

Synthesis of 2,2-Dilinoleyl-4-(4-hydroxybutyl)-[1,3]-dioxolane (II)

A mixture of dilinoleyl ketone (I, previously prepared as described in Example 1, 1.05 g, 2.0 mmol), 1,2,6-hexanetriol (0.54 g, 4 mmol) and pyridinium p-toluenesulfonate (100 mg, 0.4 mmol) in 150 mL of toluene was refluxed under nitrogen overnight with a Dean-Stark tube to remove water. The resulting mixture was cooled to room temperature. The organic phase was washed with water (2×60 mL), brine (60 mL), and dried over anhydrous Na$_2$SO$_4$. Evaporation of the solvent resulted in a yellowish oily residual (1.5 g). The crude product was purified by column chromatography on silica gel (230-400 mesh, 100 mL) with 0-0.5% methanol in dichloromethane as eluent. This afforded 1.4 g of pure II as colourless oil.

dichloromethane as eluent resulted in 0.95 g of the product DLin-K-C4-DMA as pale oil. $^1$H NMR (400 MHz, CDCl$_3$) δ: 5.26-5.49 (8, m, 4×CH═CH), 3.97-4.15 (2H, m, 2×OCH), 3.45 (1H, t OCH), 2.78 (4H, t, 2×C═C—CH$_2$—C═C), 2.45-2.55 (2H, m, NCH$_2$), 2.40 (6H, s, 2×NCH$_3$), 2.05 (8H, q, 4×allylic CH$_2$), 1.45-1.75 (8H, m, CH$_2$), 1.2-1.45 (32H, m), 0.90 (6H, t, 2×CH$_3$) ppm.

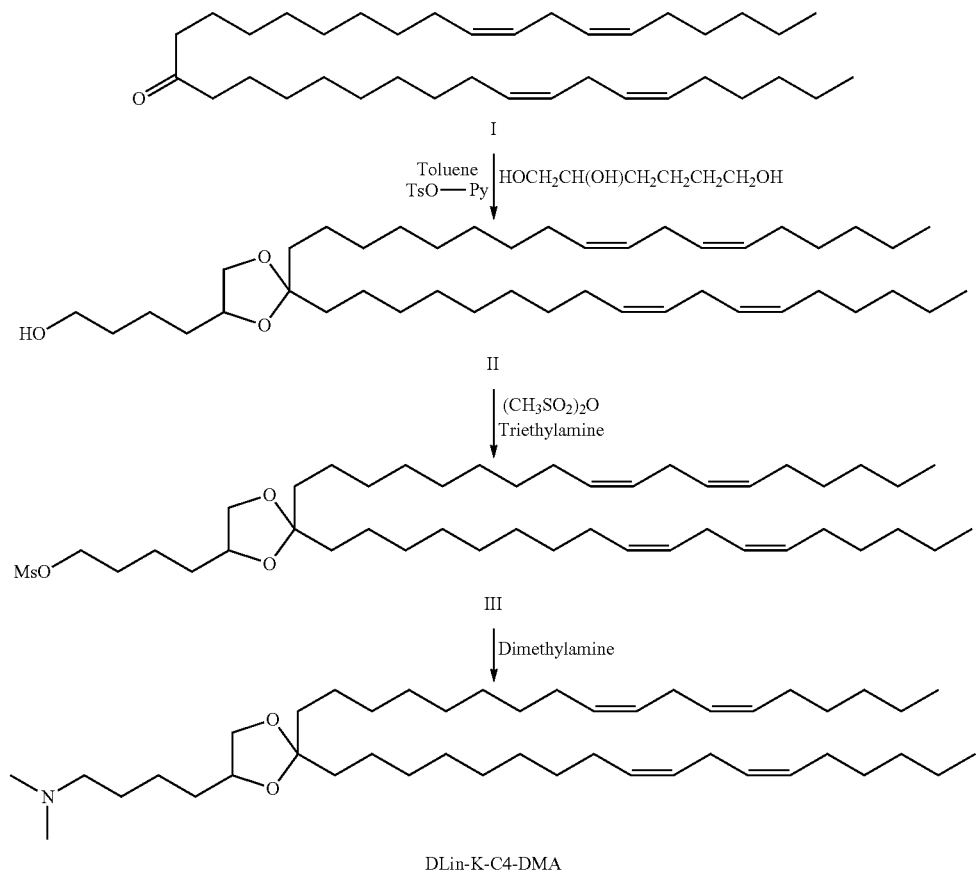

Synthesis of 2,2-Dilinoleyl-4-(4-methanesulfonylbutyl)-[1,3]-dioxolane

To a solution of 2,2-dilinoleyl-4-(4-hydroxybutyl)[1,3]-dioxolane (H, 1.4 g, 2 mmol) and dry triethylamine (0.73 g, 7.2 mmol) in 150 mL of anhydrous CH$_2$Cl$_2$ was added methanesulfonyl anhydride (1.0 g, 5.7 mmol) under nitrogen. The resulting mixture was stirred at room temperature overnight. The organic phase was washed with water (2×75 mL), brine (75 mL), and dried over anhydrous Na$_2$SO$_4$. The solvent was evaporated to afford 1.45 g of pale oil as a crude product. The crude product was used in the following step without further purification.

Synthesis of 2,2-Dilinoleyl-4-(4-dimethylaminobutyl)[1,3]-dioxolane (DLin-K-C4-DMA To the above crude material (III, 1.45 g) under nitrogen was added 60 mL of dimethylamine in THF (2.0 M). The resulting mixture was stirred at room temperature for 6 days. The solid was filtered. An oily residual (1.2 g) was obtained upon evaporation of the solvent. Column chromatography on silica gel (230-400 mesh, 100 mL) with 0-5% methanol gradient in

Example 6

Synthesis of 2,2-Dilinoleyl-5-Dimethylaminomethyl-[1,3]-Dioxane (DLin-K6-DMA)

DLin-K6-DMA was synthesized as described and shown in the schematic diagram below.

Synthesis of 2,2-Dilinoleyl-5-hydroxymethyl)[1,3]-dioxane (II)

A mixture of dilinoleyl ketone (I, previously prepared as described in Example 1, 1.05 g, 2.0 mmol), 2-hydroxymethyl-1,3-propanediol (475 mg, 4 mmol) and pyridinium p-toluenesulfonate (100 mg, 0.4 mmol) in 150 mL of toluene was refluxed under nitrogen overnight with a Dean-Stark tube to remove water. The resulting mixture was cooled to room temperature. The organic phase was washed with water (2×60 mL), brine (60 mL), and dried over anhydrous Na$_2$SO$_4$. Evaporation of the solvent resulted in pale oil (1.2 g). The crude product was purified by column chromatography on silica gel (230-400 mesh, 100 mL) with 0-1% methanol gradient in dichloromethane as eluent. This afforded 1.0 g of pure II as colourless oil.

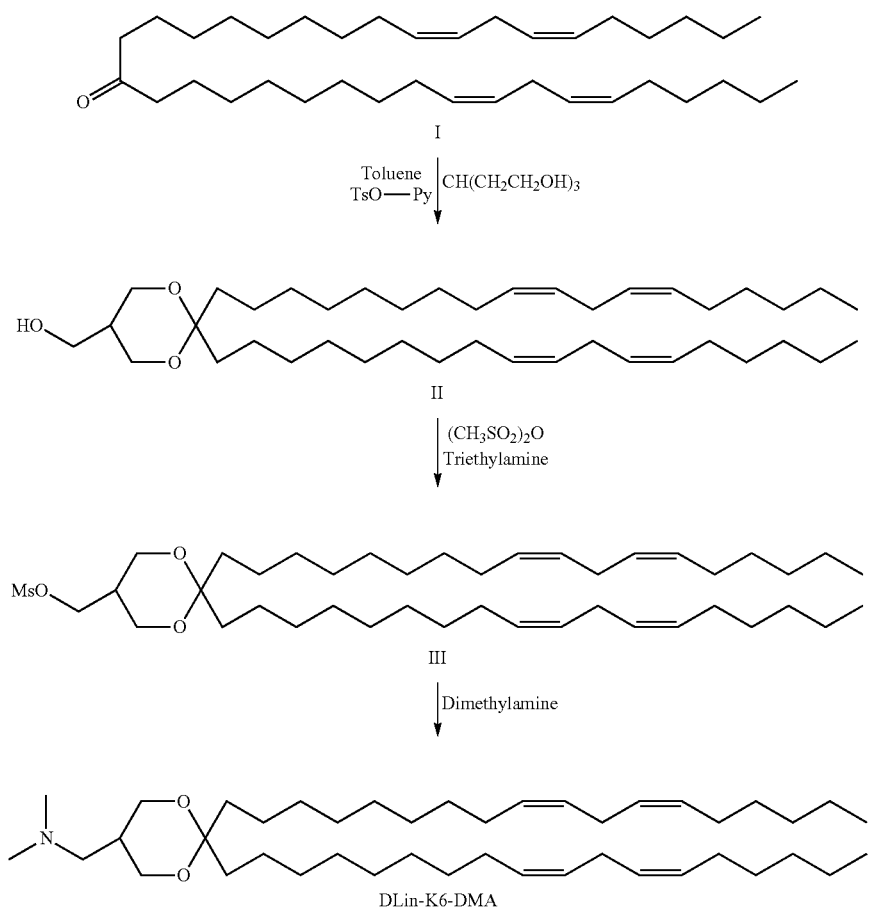

Synthesis of 2,2-Dilinoleyl-5-methanesulfonylmethyl-[1,3]-dioxane (III)

To a solution of 2,2-dilinoleyl-5-hydroxymethyl-[1,3]-dioxane (II, 1.0 g, 1.6 mmol) and dry triethylamine (430 mg, 4.2 mmol) in 120 mL of anhydrous $CH_2Cl_2$ was added methanesulfonyl anhydride (600 mg, 3.3 mmol) under nitrogen. The resulting mixture was stirred at room temperature overnight. The organic phase was washed with water (2×60 mL), brine (60 mL), and dried over anhydrous $Na_2SO_4$. The solvent was evaporated to afford 1.1 g of pale oil. The crude product was used in the following step without further purification.

Synthesis of 2,2-Dilinoleyl-5-dimethylaminomethyl)-[1,3]-dioxane (DLin-K6-DMA)

To the above crude material (III, 1.1 g) under nitrogen was added 20 mL of dimethylamine in THF (2.0 M). The resulting mixture was stirred at room temperature for 7 days. An oily residual was obtained upon evaporation of the solvent. Column chromatography on silica gel (230-400 mesh, 100 mL) with 0-30% ethyl acetate gradient in hexanes as eluent resulted in 260 mg of the product DLin-$K^6$-DMA as pale oil. $^1H$ NMR (400 MHz, $CDCl_3$) δ: 5.24-5.51 (8, m, 4×CH=CH), 4.04 (2H, dd, 2×OCH)), 3.75 (2H, dd OCH), 2.7-2.9 (2H, br, $NCH_2$), 2.78 (4H, t, 2×C=C—$CH_2$—C=C), 2.57 (6H, s, 2×$NCH_3$), 1.95-2.17 (9H, q, 4×allylic $CH_2$ and CH), 1.67-1.95 (2H, m, $CH_2$), 1.54-1.65 (4H, m, 2×$CH_2$), 1.22-1.45 (32H, m), 0.90 (6H, t, 2×$CH_3$) ppm.

Example 7

Synthesis of Dilinoleylmethyl 3-Dimethylaminopropionate (DLin-M-K-DMA)

DLin-M-K-DMA was synthesized as described and shown in the schematic diagram below.

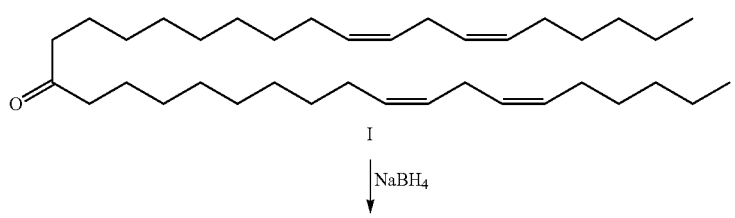

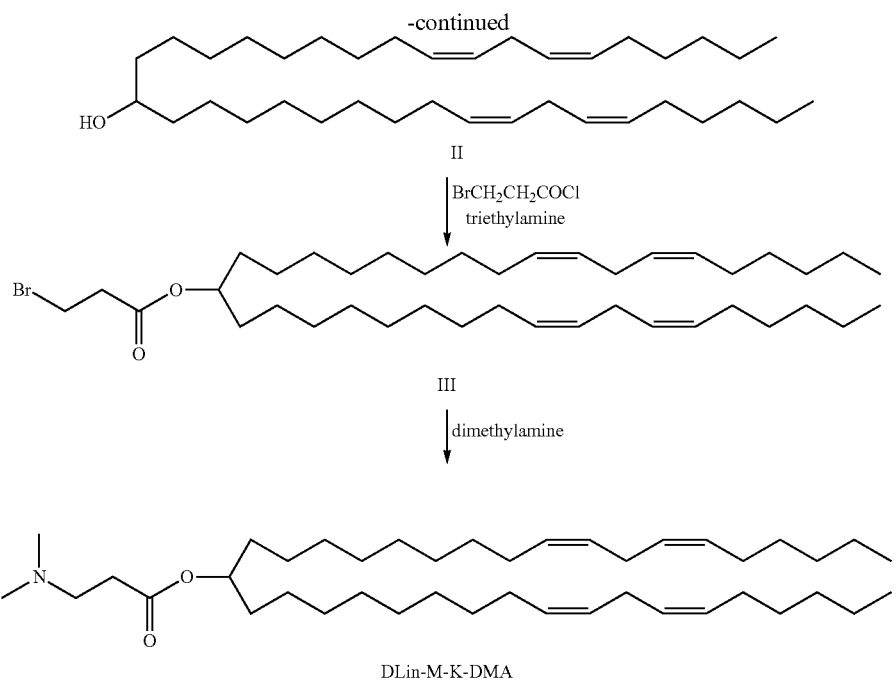

DLin-M-K-DMA

Synthesis of Dilinoleylmethanol (II)

To a solution of dilinoley ketone (I, 1.3 g) in methanol (130 mL) was added NaBH$_4$ (0.7 g). The resulting solution was stirred at room temperature for 60 min. The mixture was poured into 300 mL of ice water. The aqueous phase was extracted with ether (3×100 mL). The combined ether phase was washed with water (100 mL), brine (100 mL) and dried over anhydrous Na$_2$SO$_4$. Evaporation of the solvent gave a yellowish oily residual (1.4 g). The crude product was purified by column chromatography on silica gel (230-400 mesh, 100 mL) with 0-5% ethyl acetate gradient in hexanes as eluent. This resulted in 1.1 g of pure II as pale oil.

Synthesis of Dilinoleylmethyl 3-Bromopropionate (III)

To a solution of dilinoleylmethanol (II, 560 mg, 1 mmol) and dry triethylamine (0.44 g, 4.2 mmol) in 50 mL of anhydrous CH$_2$Cl$_2$ was added dropwise 3-bromopropionyl chloride (technical grade, 0.34 mL) under nitrogen. The resulting mixture was stirred at room temperature for 3 days. The organic phase was diluted with 50 mL of dichloromethane and washed with water (3×50 mL), brine (50 mL), and dried over anhydrous Na$_2$SO$_4$. The solvent was evaporated to afford 610 mg of brownish oil as a crude product. The crude product was purified by column chromatography on silica gel (230-400 mesh, 100 mL) with 0-3% ethyl acetate gradient in hexanes as eluent. This resulted in 540 g of a mixture of III as a major product and a by-product. The mixture was used in the following step without further purification.

Synthesis of Dilinoleylmethyl 3-Dimethylaminopropionate (DLin-M-K-DMA)

To the above mixture (III, 540 mg) under nitrogen was added 15 mL of dimethylamine in THF (2.0 M). The resulting mixture was stirred at room temperature for 8 days. The solid was filtered. Upon evaporation of the solvent, a brownish residual was resulted. Column chromatography on silica gel (230-400 mesh, 100 mL) with 0-3% methanol in dichloromethane as eluent resulted in 430 mg of the product DLin-M-K-DMA as pale oil. $^1$H NMR (400 MHz, CDCl$_3$) δ: 5.25-5.50 (8, m, 4×CH=CH), 4.70-5.00 (1H, q, OCH), 2.8-3.0 (2H, m, NCH$_2$), 2.78 (4H, t, 2×C=C—CH$_2$—C=C), 2.6-2.7 (2H, m, COCH$_2$), 2.45 (6H, s, 2×NCH$_3$), 2.05 (8H, q, 4×allylic CH$_2$), 1.45-1.75 (4H, m, CH$_2$), 1.2-1.45 (32H, m), 0.90 (6H, t, 2×CH$_3$) ppm.

Example 8

Synthesis of 2,2-Dilinoleyl-4-N-Methylpepiazino-[1,3]-Dioxolane (DLin-K-MPZ)

DLin-K-MPZ was synthesized as described below and shown in the following diagram.

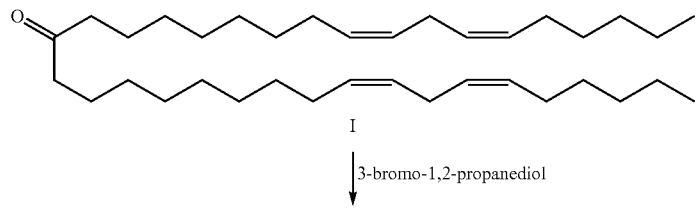

I 3-bromo-1,2-propanediol

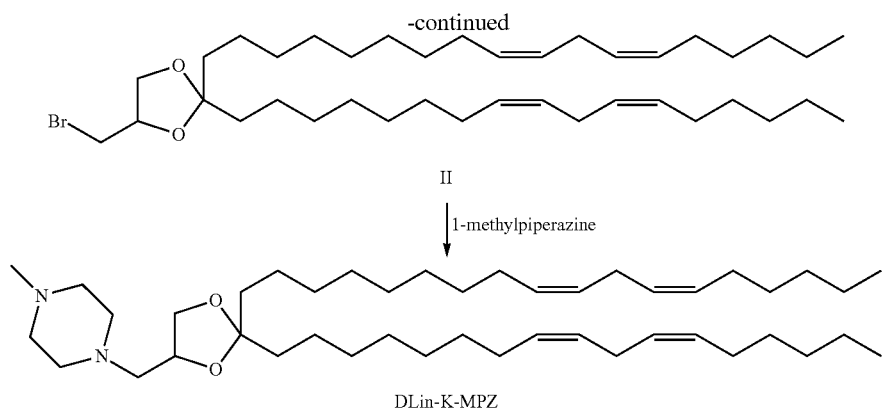

II

↓ 1-methylpiperazine

DLin-K-MPZ

Step 1

To a mixture of dilinoleyl ketone (I, 1.3 gm, 2.5 mmol), 3-Bromo1,2-propane diol (1.5 gm, 9.7 mmol) and PPTS (Pyridinium-p-toluene sulfonate) (100 mg) in 25 mL of Toluene was refluxed under nitrogen for over night with a Dean-stark tube to remove water. The resulting mixture was cooled to room temperature. The organic phase was washed with water (2×50 mL) and saturated NaHCO$_3$ solution, dried over anhydrous Na$_2$SO$_4$, evaporation of solvent resulted in a yellowish oily residue. Column Chromatography on silica (230-400 mesh), with 0-5% ether as eluent in hexanes afforded 750 mg of the ketal, which was further reacted with Methyl piperzine as follows.

Step 2

To a mixture of D-Lin-Ketal (II, 250 mg, 0.37 mmol) and K$_2$CO$_3$ (138 mg, 1 mmol) in 5 mL of acetonitrile was added Morpholine (50 mg, 0.50 mmol). Then the resulting solution was refluxed under argon overnight. The resulting mixture was cooled to room temperature, solvent was evaporated the organic phase was washed with water (2×50 mL), and dried over anhydrous Na$_2$SO$_4$. Evaporation of the solvent resulted in yellowish oily residue. Column chromatography on silica gel (230-400 mesh, 500 mL) eluted with 25-50% hexanes and ethyl acetate, and then eluted with 0-5% methanol gradient in dichloromethane. This gave 225 mg of the desired product D-Lin-K-N-methylpiperzine(D-Lin-K-MPZ).

$^1$H NMR (300 MHz, CDCl$_3$) δ: 5.27-5.46 (8H, m), 4.21-4.31 (1H, m), 4.06-4.09 (1H, t), 3.49-3.57 (1H, t) 3.49-3.55 (1H, t), 2.75-2.81 (4H, t) 2.42-2.62 (8H, m), 2.30 (3H, s), 2.02-2.09 (8H, m) 1.55-1.65 (4H, m), 1.2-1.47 (32H, m), 0.87-0.90 (6H, t) ppm.

Example 9

Synthesis of 2,2-Dioleoyl-4-Dimethylaminomethyl-[1,3]-Dioxolane (DO-K-DMA)

DO-K-DMA having the structure shown below was prepared using a method similar to the method described in Example 1 for producing D-Lin-K-DMA, except the initial starting material was oleoyl methane sulfonate, instead of linoleyl methane sulfonate.

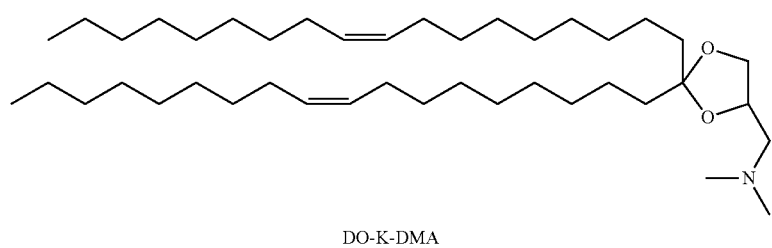 [SMILES: CCCCCCCC/C=C\CCCCCCCCC1(CCCCCCCC/C=C\CCCCCCCC)OCC(CN(C)C)O1]

DO-K-DMA $^1$H NMR (300 MHz, CDCl$_3$) δ: 5.32-5.40 (4H, m), 4.21-4.31 (1H, m), 4.06-4.10 (1H, t), 3.49-3.55 (1H, t), 2.5-2.6 (2H, m), 2.35 (6H, s), 1.90-2.00 (8H, m), 1.70-1.80 (2H, m), 1.55-1.65 (8H, m), 1.2-1.47 (40H, m), 0.87-0.90 (6H, t) ppm.

Example 10

Synthesis of 2,2-Distearoyl-4-Dimethylaminomethyl-[1,3]-Dioxolane (DS-K-DMA)

DS-K-DMA having the structure shown below was synthesized as described below.

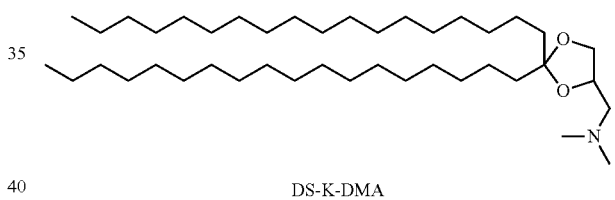

DS-K-DMA

To a solution of DO-K-DMA prepared as described in Example 8 (250 mg, 0.4 mmol) was added in ethanol Palladium charcoal, and the resulting mixture was stirred under hydrogen atmosphere over night. The reaction mixture was filtered through celite, the solvent was evaporated, and then the crude product was purified by column chromatography on silica gel (230-400 mesh, 500 mL) and eluted with 25-50% ethyl acetate as gradient in hexanes. This gave white solid 225 mg of the desired product DS-K-DMA.

$^1$H NMR (300 MHz, CDCl$_3$) δ: 4.21-4.31 (1H, m), 4.06-4.09 (1H, t), 3.49-3.55 (1H, t), 2.5-2.6 (2H, m), 2.35 (6H, s), 1.55-1.65 (4H, m), 1.2-1.47 (40H, m), 0.87-0.90 (6H, t) ppm.

Example 11

Synthesis of 2,2-Dilinoleyl-4-N-Morpholino[1,3]-Dioxolane (DLin-K-MA)

Dlin-K-MA having the structure shown below was synthesized as described below.

To a mixture of D-Lin-Ketal (I, 250 mg, 0.37 mmol) and K$_2$CO$_3$ (138 mg, 1 mmol) in 5 mL of acetonitrile was added Morpholine (50 mg, 0.57 mmol). Then the resulting solution was refluxed under argon overnight. The resulting mixture was cooled to room temperature, solvent was evaporated, the organic phase was washed with water (2×50 mL), and dried over anhydrous Na$_2$SO$_4$. Evaporation of the solvent resulted in yellowish oily residue.

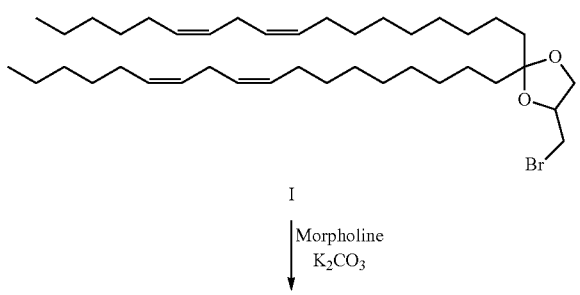

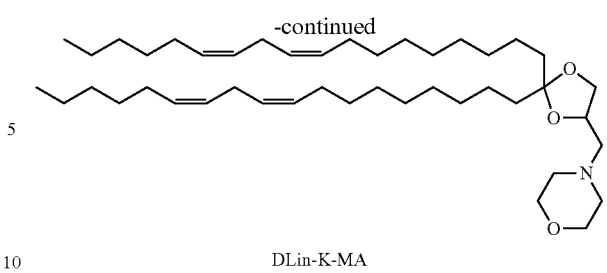

Column chromatography on silicagel (230-400 mesh, 500 mL) eluted with 25-50% hexanes and ethyl acetate, and then eluted with 0-5% methanol as gradient in dichloromethane. This gave 225 mg of the desired product DLin-K-MA.

$^1$H NMR (300 MHz, CDCl$_3$) δ: 5.27-5.46 (8H, m), 4.21-4.31 (1H, m), 4.06-4.09 (1H, t), 3.71-3.73 (4H, t) 3.49-3.55 (1H, t), 2.78 (4H, t) 2.42-2.62 (6H, m), 2.02-2.09 (8H, m) 1.55-1.65 (4H, m), 1.2-1.47 (32H, m), 0.87-0.90 (6H, t) ppm.

Example 12

Synthesis of 2,2-Dilinoleyl-4-Trimethylamino-[1,3]-Dioxolane Chloride (DLin-K-TMA.CL)

DLin-K-TMA.Cl was Synthesized as Described and Shown in the schematic diagram below.

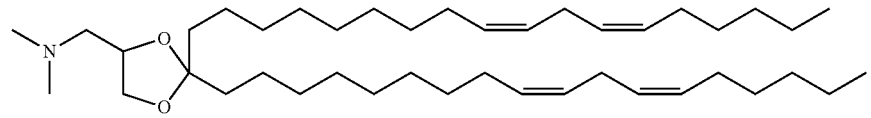

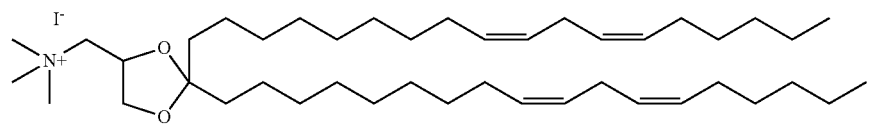

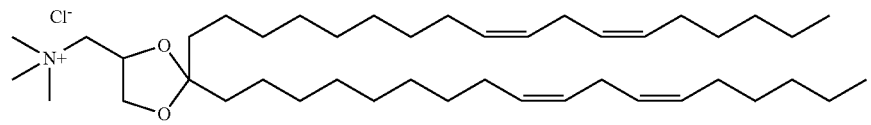

Synthesis of 2,2-Dilinoleyl-4-dimethylamino-[1,3]-dioxolane (DLin-K-DMA)

DLin-K-DMA was prepared as described in Example 1.

Synthesis of 2,2-Dilinoleyl-4-trimethylamino-[1,3]-dioxolane Chloride (DLin-K-TMA.I)

A mixture of 2,2-dilinoleyl-4-dimethylamino-[1,3]-dioxolane (DLin-K-DMA, 1.5 g, 2.4 mmol) and CH$_3$I (4.0 mL, 64 mmol) in 10 mL of anhydrous CH$_2$Cl$_2$ was stirred under nitrogen at room temperature for 9 days. Evaporation of the solvent and excess of iodomethane afforded 20 g of yellow syrup as crude DLin-K-TMA.I, which was used in the following step without further purification.

Preparation of 2,2-Dilinoleyl-4-trimethylamino-[1,3]-dioxolane Chloride (DLin-K-TMA.Cl)

The above crude DLin-K-TMA.I (2.0 g) was dissolved in 100 mL of CH$_2$Cl$_2$ in a separatory funnel. 30 mL of 1N HCl methanol solution was added, and the resulting solution was shaken well. To the solution was added 50 mL of brine and the mixture was shaken well. The organic phase was separated. The aqueous phase was extracted with 10 mL of CH$_2$Cl$_2$. The organic phase and extract were then combined. This completed the first step of ion exchange. The ion exchange step was repeated four more times. The final organic phase was washed with brine (2×75 mL) and dried over anhydrous Na$_2$SO$_4$. Evaporation of the solvent gave 2.0 g of yellowish viscous oil. The product was purified by column chromatography on silica gel (230-400 mesh, 100 mL) eluted with 0-15% methanol gradient in chloroform. This afforded 1.2 g of 2,2-dilinoleyl-4-trimethylamino-[1,3]-dioxolane chloride (DLin-K-TMA.Cl) as a pale waxy material. $^1$H NMR (300 MHz, CDCl$_3$) δ: 5.25-5.45 (8H, m, 4×CH═CH), 4.55-4.75 (2H, m, 2×OCH), 4.26-4.38 (1H, dd, OCH), 3.48-3.57 (1H, dd, NCH), 3.51 (9H, s, 3×NCH$_3$), 3.11-3.22 (1H, dd, NCH), 2.77 (4H, t, 2×C═C—CH$_2$—C═C), 2.05 (8H, q, 4×allylic CH$_2$), 1.49-1.7 (4H, m, 2×CH$_2$), 1.2-1.45 (30H, m), 0.89 (6H, t, 2×CH$_3$) ppm.

Example 13

Synthesis of 2,2-Dilinoleyl-4,5-Bis(Dimethylamino Methyl)-[1,3]-Dioxolane (DLin-K$^2$-DMA)

DLin-K$^2$-DMA was synthesized as described and shown in the schematic diagrams below.

Synthesis of D-Lin-K-diethyltartarate (II)

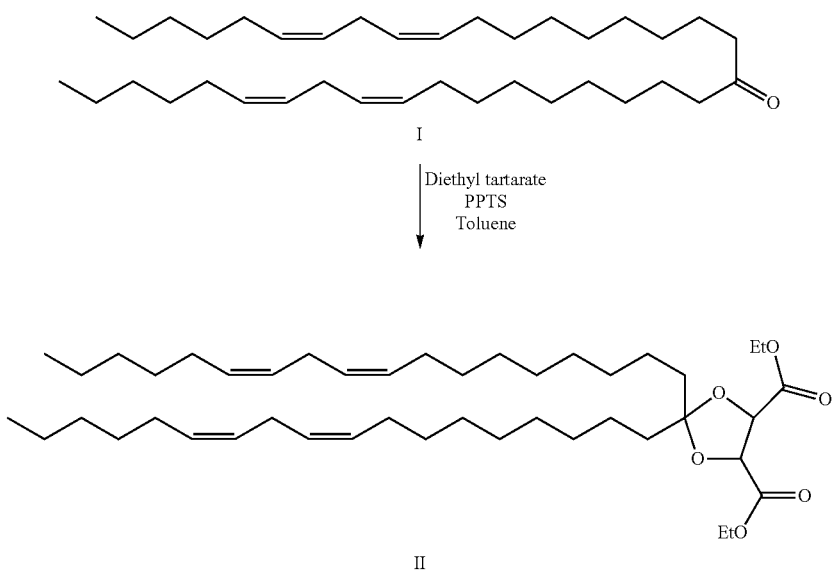

A mixture of D-Lin-Ketone (I, 1 gram, 1.9 mmol), Diethyl-D-tartarate (412 mg, 2 mmol) and Pyridinium p-tolene sulfonate (250 mg, 1 mmol) in 25 mL of toluene was refluxed under nitrogen for two days with a Dean-stark tube to remove water. The resulting mixture was cooled to room temperature. The organic phase was washed with water NaHCO$_3$ and brine (2×50 mL) and dried over anhydrous Na$_2$SO$_4$. Evaporation of the solvent resulted in yellowish oily residue. Column chromatography on silica gel (230-400 mesh, 500 mL) eluted with 0-10% ether gradients in hexanes as eluent afforded 400 mg of pure D-Lin-diethyltartarate (II).

$^1$H NMR (300 MHz, CDCl$_3$) δ: 5.27-5.46 (8H, m), 4.67 (2H, s), 4.20-4.30 (1H, t), 2.75 (4H, t), 2.02-2.09 (8H, m) 1.62-1.72 (4H, m), 1.2-1.47 (32H, m), 0.87-0.90 (6H, t) ppm.

Synthesis of D-Lin-K-diethyldiol (III)

To a solution of Lithiumaluminumhydride (32 mg, 1 mmol) in dry THF a solution of D-Lin-K-diethyltartarate (II, 600 mg, 0.85 m mol) was added in dry THF at 0° C. under argon atmosphere and then the reaction was stirred for four hours at room temperature. The reaction mixture was quenched with ice cold water and then filtered through celite and the evaporation of solvent gave crude reduced alcohol. Column chromatography on silica gel (230-400 mesh, 500 mL) eluted with 10-40% ethyl acetate gradients in hexanes as eluent afforded 350 mg of pure D-Lin-diethyltartarate (III).

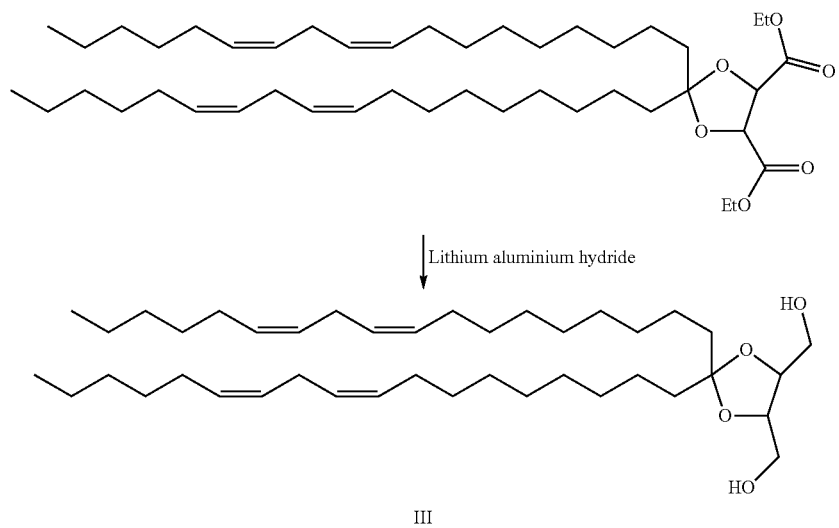

III $^1$H NMR (300 MHz, CDCl$_3$) δ: 5.27-5.46 (8H, m), 3.95 (2H, t), 3.65-3.85 (4H, dd), 2.75 (4H, t), 2.02-2.09 (8H, m) 1.62-1.72 (4H, m), 1.2-1.47 (32H, m), 0.87-0.90 (6H, t) ppm.

Synthesis of D-Lin-K-diethyldimesylate (IV)

To a mixture of D-Lin-K-diethyltartarate (III) alcohol (570 mg, 0.95 mmol) in dry dichloromethane pyridine (275 mg, 3.85 mmol) and 4-(Dimethylamino)pyridine (122 mg, 1 mmol) was added under argon atmosphere to this solution a solution of methane sulfonyl chloride (500 mg, 2.5 mmol) was slowly added and stirred over night.

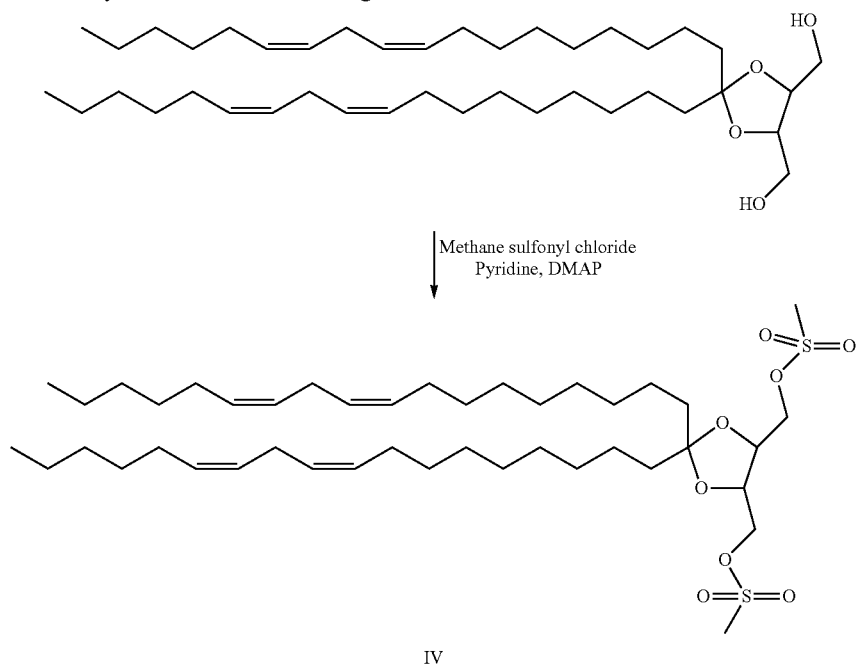

IV

The organic phase was washed with water and brine (2×50 mL) then solvent was evaporated to give yellowish oil residue. Purified over Column chromatography on silica gel (230-400 mesh, 500 mL), eluted with 10-40% ethyl acetate gradients in hexanes as eluent, afforded 300 mg of pure D-Lin-diethyltartarate (IV).

$^1$H NMR (300 MHz, CDCl$_3$) δ: 5.27-5.46 (8H, m), 4.35 (4H, d), 4.12-4.17 (2H, t), 3.08 (6H, s), 2.75 (4H, t), 2.02-2.09 (8H, m) 1.62-1.72 (4H, m), 1.2-1.47 (32H, m), 0.87-0.90 (6H, t) ppm.

Synthesis of D-Lin-K$^2$-DMA

Anhydrous dimethyl amine solution in THF was added to the reaction vessel containing (300 mg) of D-Lin-diethyltartarate (IV) at room temperature for 5 min. the reaction flask was then sealed and the mixture stirred at room temperature for 6 days. Evaporation of the solvent left 300 mg of residual. the crude product was purified by column chromatography on silica gel (230-400 mesh, 500 mL) eluted with 0-10% Methanol gradients in chloroform as eluent afforded 50 mg of pure D-Lin-K$^2$-DMA.

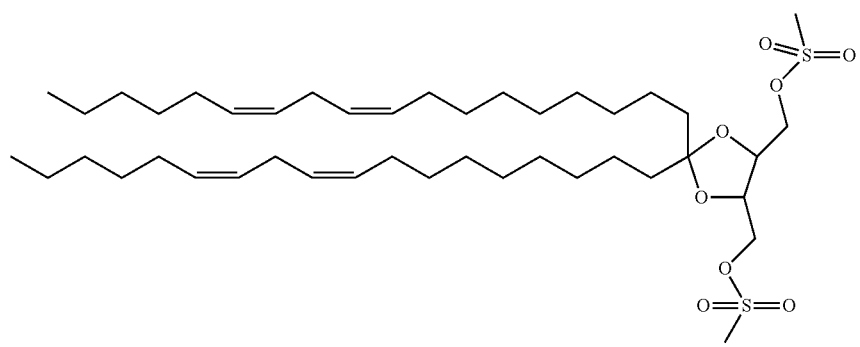

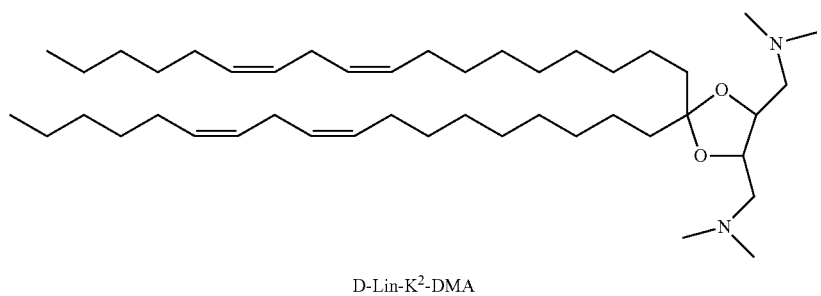

D-Lin-K²-DMA $^1$H NMR (300 MHz, CDCl$_3$) δ: 5.27-5.46 (8H, m), 3.72-3.80 (2H, t), 2.75 (4H, t), 2.49 (4H, d), 2.30 (12H, s), 2.02-2.09 (8H, m) 1.62-1.72 (4H, m), 1.2-1.47 (32H, m), 0.87-0.90 (6H, t) ppm.

Example 14

Synthesis of D-Lin-K-N-Methylpiperzine

D-Lin-K-N-methylpiperzine having the structure shown below was prepared as described below.

To a mixture of D-Lin-Ketal (I, 250 mg, 0.37 mmol) and K$_2$CO$_3$ (138 mg, 1 mmol) in 5 mL of acetonitrile was added Morpholine (50 mg, 0.50 mmol). Then the resulting solution was refluxed under argon overnight. The resulting mixture was cooled to room temperature, solvent was evaporated the organic phase was washed with water (2×50 mL), and dried over anhydrous Na$_2$SO$_4$. Evaporation of the solvent resulted in yellowish oily residue. Column chromatography on silica gel (230-400 mesh, 500 mL), eluted with 25-50% hexanes and ethyl acetate, and then eluted with 0-5% methanol gradient in dichloromethane. This gave 225 mg of the desired product D-Lin-K-N-methylpiperzine.

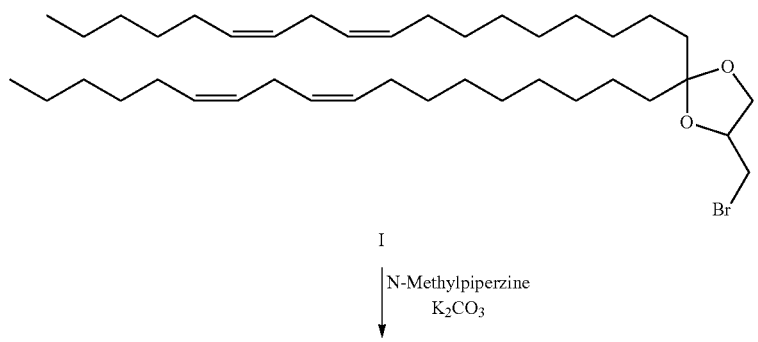

I

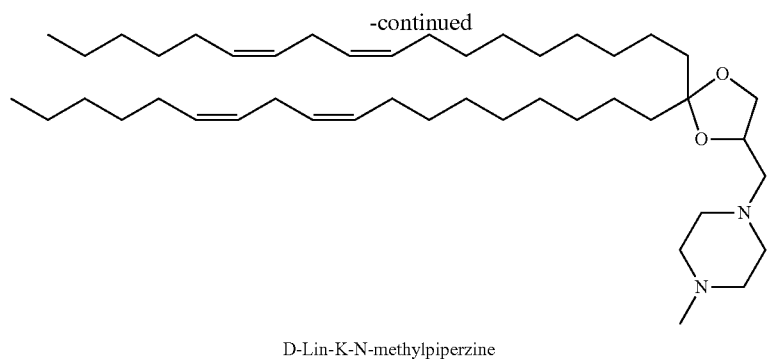

D-Lin-K-N-methylpiperzine

¹H NMR (300 MHz, CDCl₃) δ: 5.27-5.46 (8H, m), 4.21-4.31 (1H, m), 4.06-4.09 (1H, t), 3.49-3.57 (1H, t) 3.49-3.55 (1H, t), 2.75-2.81 (4H, t) 2.42-2.62 (8H, m), 2.30 (3H, s), 2.02-2.09 (8H, m) 1.55-1.65 (4H, m), 1.2-1.47 (32H, m), 0.87-0.90 (6H, t) ppm.

Example 15

Synthesis of mPEG2000-1,2-Di-O-Alkyl-SN3-Carbomoylglyceride (PEG-C-DOMG)

The PEG-lipids, such as mPEG2000-1,2-Di-O-Alkyl-sn3-Carbomoylglyceride (PEG-C-DOMG) were synthesized as shown in the schematic and described below.

Synthesis of IVa 1,2-Di-O-tetradecyl-sn-glyceride Ia (30 g, 61.80 mmol) and N,N'-succinimidylcarboante (DSC, 23.76 g, 1.5 eq) were taken in dichloromethane (DCM, 500 mL) and stirred over an ice water mixture. Triethylamine (TEA, 25.30 mL, 3 eq) was added to the stirring solution and subsequently the reaction mixture was allowed to stir overnight at ambient temperature. Progress of the reaction was monitored by TLC. The reaction mixture was diluted with DCM (400 mL) and the organic layer was washed with water (2×500 mL), aqueous NaHCO₃ solution (500 mL) followed by standard work-up. The residue obtained was dried at ambient temperature under high vacuum overnight. After drying, the crude carbonate IIa thus obtained was dissolved in dichloromethane (500 mL) and

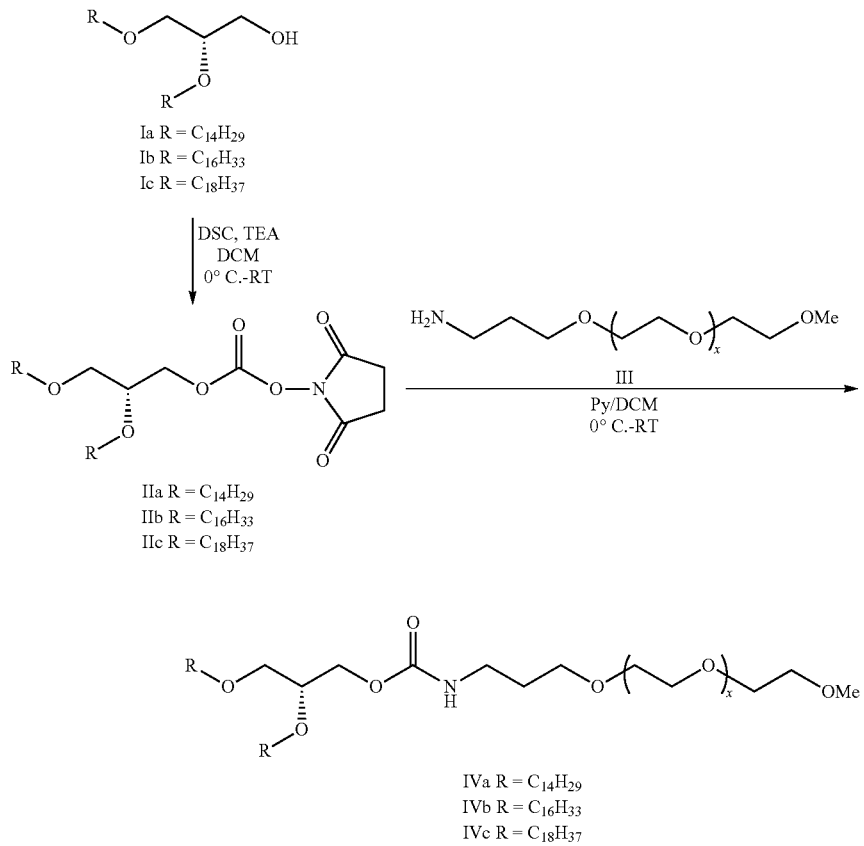

stirred over an ice bath. To the stirring solution, mPEG$_{2000}$-NH$_2$ (III, 103.00 g, 47.20 mmol, purchased from NOF Corporation, Japan) and anhydrous pyridine (Py, 80 mL, excess) were added under argon. In some embodiments, the x in compound III has a value of 45-49, preferably 47-49, and more preferably 49. The reaction mixture was then allowed to stir at ambient temperature overnight. Solvents and volatiles were removed under vacuum and the residue was dissolved in DCM (200 mL) and charged on a column of silica gel packed in ethyl acetate. The column was initially eluted with ethyl acetate and subsequently with gradient of 5-10% methanol in dichloromethane to afford the desired PEG-Lipid IVa as a white solid (105.30 g, 83%). $^1$H NMR (CDCl$_3$, 400 MHz) δ=5.20-5.12 (m, 1H), 4.18-4.01 (m, 2H), 3.80-3.70 (m, 2H), 3.70-3.20 (m, —O—CH$_2$—CH$_2$—O—, PEG-CH$_2$), 2.10-2.01 (m, 2H), 1.70-1.60 (m, 2H), 1.56-1.45 (m, 4H), 1.31-1.15 (m, 48H), 0.84 (t, J=6.5 Hz, 6H). MS range found: 2660-2836.

Synthesis of IVb 1,2-Di-O-hexadecyl-sn-glyceride Ib (1.00 g, 1.848 mmol) and DSC (0.710 g, 1.5 eq) were taken together in dichloromethane (20 mL) and cooled down to 0° C. in an ice water mixture. Triethylamine (1.00 mL, 3 eq) was added and the reaction was stirred overnight. The reaction was followed by TLC, diluted with DCM, washed with water (2 times), NaHCO$_3$ solution and dried over sodium sulfate. Solvents were removed under reduced pressure and the resulting residue of IIb was maintained under high vacuum overnight. This compound was directly used for the next reaction without further purification. MPEG$_{2000}$-NH$_2$ III (1.50 g, 0.687 mmol, purchased from NOF Corporation, Japan) and IIb (0.702 g, 1.5 eq) were dissolved in dichloromethane (20 mL) under argon. In some embodiments, the x in compound III has a value of 45-49, preferably 47-49, and more preferably 49. The reaction was cooled to 0° C. Pyridine (1 mL, excess) was added and the reaction stirred overnight. The reaction was monitored by TLC. Solvents and volatiles were removed under vacuum and the residue was purified by chromatography (first ethyl acetate followed by 5-10% MeOH/DCM as a gradient elution) to obtain the required compound IVb as a white solid (1.46 g, 76%). $^1$H NMR (CDCl$_3$, 400 MHz) δ=5.17 (t, J=5.5 Hz, 1H), 4.13 (dd, J=4.00 Hz, 11.00 Hz, 1H), 4.05 (dd, J=5.00 Hz, 11.00 Hz, 1H), 3.82-3.75 (m, 2H), 3.70-3.20 (m, —O—CH$_2$—CH$_2$—O—, PEG-CH$_2$), 2.05-1.90 (m, 2H), 1.80-1.70 (m, 2H), 1.61-1.45 (m, 6H), 1.35-1.17 (m, 56H), 0.85 (t, J=6.5 Hz, 6H). MS range found: 2716-2892.

Synthesis of IVc 1,2-Di-O-octadecyl-sn-glyceride Ic (4.00 g, 6.70 mmol) and DSC (2.58 g, 1.5 eq) were taken together in dichloromethane (60 mL) and cooled down to 0° C. in an ice water mixture. Triethylamine (2.75 mL, 3 eq) was added and the reaction was stirred overnight. The reaction was followed by TLC, diluted with DCM, washed with water (2 times), NaHCO$_3$ solution, and dried over sodium sulfate. Solvents were removed under reduced pressure and the residue was maintained under high vacuum overnight. This compound was directly used for the next reaction without further purification. MPEG$_{2000}$-NH$_2$ III (1.50 g, 0.687 mmol, purchased from NOF Corporation, Japan) and IIc (0.760 g, 1.5 eq) were dissolved in dichloromethane (20 mL) under argon. In some embodiments, the x in compound III has a value of 45-49, preferably 47-49, and more preferably 49. The reaction was cooled to 0° C. Pyridine (1 mL, excess) was added and the reaction was stirred overnight. The reaction was monitored by TLC. Solvents and volatiles were removed under vacuum and the residue was purified by chromatography (ethyl acetate followed by 5-10% MeOH/DCM as a gradient elution) to obtain the desired compound IVc as a white solid (0.92 g, 48%). $^1$H NMR (CDCl$_3$, 400 MHz) δ=5.22-5.15 (m, 1H), 4.16 (dd, J=4.00 Hz, 11.00 Hz, 1H), 4.06 (dd, J=5.00 Hz, 11.00 Hz, 1H), 3.81-3.75 (m, 2H), 3.70-3.20 (m, —O—CH$_2$—CH$_2$—O—, PEG-CH$_2$), 1.80-1.70 (m, 2H), 1.60-1.48 (m, 4H), 1.31-1.15 (m, 64H), 0.85 (t, J=6.5 Hz, 6H). MS range found: 2774-2948.

Example 16

Influence of Cationic Lipid on In Vivo Gene Silencing

It is well established that in vivo RNAi silencing of specific hepatocyte proteins can be achieved following intravenous (i.v.) administration of siRNA's encapsulated in, or associated with, select nanoparticles designed for intracellular delivery. One of the most active, and well characterized of these is a stable nucleic acid lipid particle (SNALP) containing the cationic lipid 1,2-dilinoleyloxy-3-dimethylaminopropane (DLinDMA). In this Example, rational design in combination with in vivo screening were applied to systematically modify the structure of DLinDMA and identify molecular features that enhance or reduce cationic lipid potency. More than 30 lipids were synthesized and incorporated into nucleic acid-lipid particles, i.e., lipid nanoparticles (LN) encapsulating an siRNA (LN-siRNA) targeting Factor VII (FVII), a blood clotting component synthesized and secreted by hepatocytes that is readily measured in serum. LN-siRNA systems were prepared using the same process, lipid molar ratios and particle size to minimize effects on activity resulting from formulation characteristics other than the cationic lipid. Each formulation was administered as a single bolus injection over a range of doses enabling an estimate of the siRNA dose required to reduce FVII serum protein concentrations by 50% after 24 h (ED$_{50}$).

The studies described herein were performed using the following materials and methods.

Materials and Methods

Lipids

Cationic lipids were synthesized as described in the previous Examples. Distearoylphosphatidylcholine (DSPC) was purchased from Northern Lipids (Vancouver, Canada). Cholesterol was purchased from Sigma Chemical Company (St. Louis, Mo., USA) or Solvay Pharmaceuticals (Weesp, The Netherlands).

The synthesis of N-[(methoxy poly(ethylene glycol)$_{2000}$)carbamyl]-1,2-dimyristyloxlpropyl-3-amine (PEG-C-DMA) and N-[(methoxy poly(ethylene glycol)$_{2000}$)succinimidyl]-1,2-dimyristyloxlpropyl-3-amine (PEG-S-DMA) were as described by Hayes et. al., J. Control Release 112:280-290 (2006). R-3-[(w-methoxy-poly(ethylene glycol)2000)carbamoyl)]-1,2-dimyristyloxlpropyl-3-amine (PEG-C-DOMG) was synthesized as described herein and by Akinc et. al., Nat. Biotechnol. 26:561-56 (2008). These three PEG-lipids were interchangeable in the formulation without impacting activity (data not shown), Therefore, throughout the text, they are referred to generally as PEG-lipid for purposes of clarity.

Synthesis of siRNA

All siRNAs and 2'-OMe oligoribonucleotides were synthesized by Alnylam as described in John et al. (Nature advance online publication, 26 Sep. 2007 (D01:10.1038/nature06179)). Oligonucleotides were characterized by electrospray mass spectrometry and anion exchange HPLC.

Sequences of siRNAs used in these studies were as follows:

si-FVII sense, 5' GGAUCAUCUCAAGUCUUACTT 3'; (SEQ ID NO: 33)

si-FVII antisense, 5'-GUAAGACUUGAGAUGAUCCTT-3'; (SEQ ID NO: 34)

si-Luc sense, 5'-cuuAcGcuGAGuAcuucGATT-3'; (SEQ ID NO: 35)

si-Luc antisense, 5'-UCGAAGuACUcAGCGuAAGTT-3', (SEQ ID NO: 36)

with lower-case letters denoting 2'-O-Me-modified nucleotides; and underlined letters denoting 2'-F-modified nucleotides. All siRNAs contained phosphorothioate linkages between the two thymidines (T) at the 3' end of each strand.

Preformed Vesicle Method to Formulate Nucleic Acid-Lipid Particles

Nucleic acid-lipid particles were made using the preformed vesicle (PFV) method, essentially as described in Maurer et al. (Biophys J., 2001). Cationic lipid, DSPC, cholesterol and PEG-lipid were solubilised in ethanol at a molar ratio of 40/10/40/10, respectively. The lipid mixture was added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids were extruded through two stacked 80 nm pore-sized filters (Nuclepore) at 22° C. using a Lipex Extruder (Hope, M. J. et al. Biochim. Biophys. Acta 812:55-65 (1985)) until a vesicle diameter of 70-90 nm, as determined by Nicomp analysis, was obtained. This generally required 1-3 passes. The FVII siRNA (solubilised in a 50 mM citrate, pH 4 aqueous solution containing 30% ethanol) was added to the pre-equilibrated (35° C.) vesicles, at a rate of ~5 mL/min with mixing. After a final target siRNA/lipid ratio of 0.06 (wt/wt) was achieved, the mixture was incubated for a further 30 min at 35° C. to allow vesicle re-organization and encapsulation of the FVII siRNA. The ethanol was then removed and the external buffer replaced with PBS (155 mM NaCl, 3 mM Na2HPO4, 1 mM KH2PO4, pH 7.5) by either dialysis or tangential flow diafiltration.

Particle Size Analysis

The size distribution of liposomal siRNA formulations was determined using a NICOMP Model 380 Sub-micron particle sizer (PSS NICOMP, Particle Sizing Systems, Santa Barbara, Calif.). Mean particle diameters were generally in the range 50-120 nm, depending on the lipid composition used. Liposomal siRNA formulations were generally homogeneous and had standard deviations (from the mean particle size) of 20-50 nm, depending on the lipid composition and formulation conditions used.

Measurement of Free siRNA by Ion Exchange Chromatography

Anion exchange chromatography using either DEAE Sepharose columns or commercial centrifugal devices (Vivapure D Mini columns) was used to measure the amount of free siRNA in the sample. For the DEAE Sepharose columns, siRNA-containing formulations were eluted through the columns (~2.5 cm bed height, 1.5 cm diameter) equilibrated with HBS (145 mM NaCl, 20 mM HEPES, pH 7.5). An aliquot of the initial and eluted sample were assayed for lipid and siRNA content by HPLC and A260, respectively. The percent encapsulation was calculated based on the change in siRNA to lipid ratios between the pre and post column samples. For the Vivapure centrifugal devices, an aliquot (0.4 mL, <1.5 mg/mL siRNA) of the siRNA-containing formulation was eluted through the positively charged membrane by centrifugation (2000×g for 5 min). Aliquots of the pre and post column samples were analyzed as described above to determine the amount of free siRNA in the sample.

Determination of siRNA Concentration siRNA concentration was determined by measuring the absorbance at 260 nm after solubilization of the lipid. The lipid was solubilized according to the procedure outlined by Bligh and Dyer (Bligh, et al., Can. J. Biochem. Physiol. 37:911-917 (1959). Briefly, samples of liposomal siRNA formulations were mixed with chloroform/methanol at a volume ratio of 1:2.1:1 (aqueous sample:methanol:chloroform). If the solution was not completely clear (i.e., a single, clear phase) after mixing, an additional 50-100 mL (volume recorded) of methanol was added and the sample was remixed. Once a clear monophase was obtained, the sample was assayed at 260 nm using a spectrophotometer. siRNA concentration was determined from the A260 readings using a conversion factor of approximately 45 µg/mL=1.0 OD, using a 1.0 cm path length. The conversion factor in the chloroform/methanol/water monophase varies (35-50 µg/mL=1.0 OD) for each lipid composition and is determined empirically for each novel lipid formulation using a known amount of siRNA.

Determination of Lipid Concentrations and Ratios

Cholesterol, DSPC, PEG-lipid, and the various cationic lipids were measured against reference standards using a Waters Alliance HPLC system consisting of an Alliance 2695 Separations Module (autosampler, HPLC pump, and column heater), a Waters 2424 Evaporative Light Scattering Detector (ELSD), and Waters Empower HPLC software (version 5.00.00.00, build number 1154; Waters Corporation, Milford, Mass., USA). Samples (15 µL) containing 0.8 mg/mL total lipid in 90% ethanol were injected onto a reversed-phase XBridge C18 column with 2.5 µm packing, 2.1 mm×50 mm (Waters Corporation, Milford, Mass., USA) heated at 55° C. and chromatographed with gradient elution at a constant flow rate of 0.5 mL/min. The mobile phase composition changed from 10 mM $NH_4HCO_3$:methanol (20:80) to THF:10 mM $NH_4HCO_3$:methanol (16:4:80) over 16 minutes. The gas pressure on the ELSD was set at 25 psi, while the nebulizer heater-cooler set point and drift tube temperature set point were set at 100% and 85° C. respectively. Measured lipid concentrations (mg/mL) were converted to molar concentrations, and relative lipid ratios were expressed as mol % of the total lipid in the formulation.

Determination of Encapsulation Efficiency

Trapping efficiencies were determined after removal of external siRNA by tangential flow diafiltration or anion exchange chromatography. siRNA and lipid concentrations were determined (as described above) in the initial formulation incubation mixtures and after tangential flow diafiltration. The siRNA-to-lipid ratio (wt/wt) was determined at both points in the process, and the encapsulation efficiency was determined by taking the ratio of the final and initial siRNA-to-lipid ratio and multiplying the result by 100 to obtain a percentage.

In Vivo Screening of Cationic Lipids for FVII Activity

FVII activity was evaluated in FVII siRNA-treated animals at 24 hours after intravenous (bolus) injection in C57BL/6 mice or 48 hours after intravenous (bolus) injection in SD rats. Six to 8 week old, female C57Bl/6 mice were obtained from Charles River Laboratories and acclimated for one week prior to use in studies. Animals were held in a pathogen-free environment and all procedures involving animals were performed in accordance with the guidelines established by the Canadian Council on Animal Care.

LN-siRNA systems containing Factor VII siRNA were diluted to the appropriate concentrations in sterile phosphate buffered saline immediately prior to use, and the formulations were administered intravenously via the lateral tail vein in a total volume of 10 ml/kg. After 24 h, animals were anaesthetised with Ketamine/Xylazine and blood was collected by cardiac puncture and processed to serum (Microtainer Serum Separator Tubes; Becton Dickinson, Franklin Lakes, N.J., USA). Serum was tested immediately or stored at −70° C. for later analysis for serum Factor VII levels.

FVII was measured using a commercially available kit (Biophen FVII Kit™; Aniara Corp., Mason, Ohio), following the manufacturer's instructions at a microplate scale. FVII reduction was determined against untreated control animals, and the results were expressed as % Residual FVII. Five dose levels (0.1, 0.3, 0.5, 1.0, and 3.0 mg/kg) were typically used.

Pharmacokinetic and Liver Analysis

A fluorescently labeled siRNA (Cy-3 labeled luciferase siRNA, Alnylam Pharmaceuticals) was used to measure the siRNA content in plasma and liver after iv administration of LN-siRNA systems. The measurements were done by first extracting the Cy3-siRNA from the protein-containing biological matrix and then analyzing the amount of Cy-3 label in the extract by fluorescence. Two extraction methods were used, a chloroform/methanol mixture for the plasma samples and a commercial phenol/chloroform mixture (Trizol® reagent) with the tissue samples.

For plasma, blood was collected in EDTA-containing Vacutainer tubes and centrifuged at 1000×g for 10 min at 4-8° C. to isolate the plasma. The plasma was transferred to an eppendorf tube and either assayed immediately or stored in a −30° C. freezer. An aliquot of the plasma (100 μL maximum) was diluted to 500 μL with PBS (145 mM NaCl, 10 mM phosphate, pH 7.5), methanol (1.05 mL and chloroform (0.5 mL) was added, and the sample vortexed to obtain a clear, single phase solution. Water (0.5 mL) and chloroform (0.5 mL) was then added and the resulting emulsion sustained by mixing periodically for a minimum of 3 minutes. The mixture was centrifuged at 3000 rpm for 20 minutes and the top aqueous phase containing the Cy-3-label transferred to a new test tube. The fluorescence of the solution was measured using an SLM Fluorimeter at an excitation wavelength of 550 nm (2 nm bandwidth) and emission wavelength of 600 nm (16 nm bandwidth). A standard curve was generated by spiking aliquots of plasma from untreated animals with the Cy-3-siRNA containing formulation (0 to 15 μg/mL), and the sample processed as indicated above.

For liver, sections (400-500 mg) of tissue from saline-perfused animals was accurately weighed and homogenized in 1 mL of Trizol using Fastprep tubes. An aliquot of the homogenate (typically equivalent to 50 mg of tissue) was transferred to an eppendorf tube and additional Trizol added to 1 mL final. Chloroform (0.2 mL) was added, and the solution was mixed and incubated for 2-3 min before being centrifuged for 15 min at 12,000×g. An aliquot (0.5 mL) of the top Cy-3-containing aqueous phase was diluted with 0.5 mL of PBS and the fluorescence of the sample measured as described above.

Measurement of FVII Protein in Serum

Serum Factor VII levels were determined using the colorimetric Biophen VII assay kit (Anaira, USA). Briefly, serially diluted pooled control serum (200%-3.125%) and appropriately diluted plasma samples from treated animals were analyzed using the Biophen VII kit according to manufacturer's instructions in 96-well, flat bottom, non-binding polystyrene assay plates (Corning, Corning, N.Y.) and absorbance at 405 nm was measured. A calibration curve was generated using the serial diluted control serum and used to determine levels of Factor VII in serum from treated animals.

Determination of Tolerability

The tolerability of empty DLin-K-C2-DMA lipid particles (DLin-K-C2-DMA/DSPC/Chol/PEG-C-DOMG (40/10/40/10)) was evaluated by monitoring weight change, cageside observations, clinical chemistry and, in some instances, hematology in femal Sprague Dawley rats and female C57BL/6 mice. Animal weights were recorded prior to treatment and at 24 hours after intravenous treatment with various dosages. Data was recorded as % Change in Body Weight. In addition to body weight measurements, clinical chemistry panel, including liver function markers, was obtained at each dose level at 24 hours post-injection using an aliquot of the serum collected for FVII analysis. Samples were sent to the Central Laboratory for Veterinarians (Langley, B C) for analysis. In some instances, additional animals were included in the treatment group to allow collection of whole blood for hematology analysis.

In Situ Determination of pKa Using TNS

In situ pKa measurements were made using the pH sensitive fluorescent probe TNS, using a modification of the approach previously published in Bailey, A. L. and Cullis, P. R., *Biochemistry* 33:12573-12580 (1994).

Results

Initial studies were performed in eight to 10 week old, female C57BL/6 mice in two stages. In the first stage, the activity associated with the benchmark lipid DLinDMA was compared to the activity associated with modified forms of DLinDMA. This stage resulted in the identification of DLin-K-DMA as having increased activity as compared to DLinDMA. Therefore, in the second stage, the activities of modified forms of DLinDMA were compared to the activity of DLin-K-DMA. Dose response curves were used to estimate an $ED_{50}$ for each formulation, which is defined as the siRNA dose required to reduce the concentration of serum FVII protein by 50%, and is ~1.0 mg/kg for the DLinDMA benchmark formulation. The $ED_{50}$ for formulations with poor activity is expressed as a range, e.g. 12-25 mg/kg, indicating that a 50% reduction in serum FVII protein levels occurs between these siRNA doses. If a formulation showed good activity ($ED_{50}$<2 mg/kg), then the dose response was repeated over a narrower dose range and head-to-head with DLinDMA for greater comparative accuracy.

Screen 1a: Headgroup Modifications to DLinDMA and In Vivo FVII Activity

For the purposes of this study, DLinDMA was divided into three key structural domains that were modified separately, including the headgroup, the linker, and the hydrocarbon chains. The dimethylaminopropane headgroup is hydrophilic and contains a tertiary amine function with an apparent pKa (in situ) of pH 6.4. Consequently, DLinDMA is almost completely charged at pH 4, the pH at which the LN-siRNA systems are formed through electrostatic interaction with siRNA. Whereas, at pH 7.4, ~5-10% of DLinDMA molecules are charged; therefore, the cationic charge density at the surface of these nanoparticles in the circulation is relatively low. In contrast, at endosomal pH's (~pH 5), the surface charge density is increased significantly, which is expected to promote the formation of ion pairs with anionic phospholipids and disrupt the endosomal membrane (Hafez, I. M. and Cullis, P. R., *Adv. Drug Deliv. Rev.* 4:139-148 (2001) and Xu, Y. and Szoka, F. C., *Biochemistry* 35:5616-5623 (1996)).

The headgroup modifications made to DLinDMA are shown in Table 3, and the first three were designed to alter the nature of the positive charge. DLinTMA contains a quaternary amino group and is permanently charged, and showed reduced activity with an estimated $ED_{50}$ between 2-5 mg/kg. A similar decrease in activity was observed when the dimethylamine function was replaced by a piperazine moiety (DLinMPZ, $ED_{50}$ 2-5 mg/kg), and reduced more significantly when substituted by a morpholino group (DLinMA, $ED_{50}$ 12-25 mg/kg).

One rationale for making the remaining two modifications shown in Table 3 was to compare the activities of two lipids with similar headgroup structures but with different rates of metabolism in vivo. Lipid degradation was not measured in vivo for any of the lipids screened here, but it is expected that an ethoxy group (DLin-EG-DMA) would be more resistant to enzymatic cleavage than an ester group (DLinDAC) (Martin, B. et al., *Curr. Pharm. Des* 11:375-394 (2005)); none the less, both lipids exhibited similar activity.

Screen 1b: Linker Modifications to DLinDMA and In Vivo FVII Activity

DLinDMA has two unsaturated hydrocarbon chains joined to the dimethylaminopropane headgroup through two ethoxy linkages. In a bilayer structure, the linker region resides at the membrane interface, an area of transition between the hydrophobic membrane core and hydrophilic headgroup surface. The approach to linker modification of DLinDMA was to introduce linker groups expected to exhibit different rates of chemical or enzymatic stability and spanning a range of hydrophilicity. The ethoxy moiety is considered to be more resistant to degradation than most other types of chemical bonds in vivo, which may be why these lipids have been found to be less well tolerated than cationic lipids with ester linkages for example (Martin, B. et al., *Curr. Pharm. Des* 11:375-394 (2005)). A variety of these rationally designed lipids were made, characterized, and tested, including those shown in Table 4.

TABLE 3

Headgroup modifications to DLinDMA

| Abbreviated Name | Chemical Name | $ED_{50}$ (mg/kg) | Headgroup Modification |
|---|---|---|---|
| DLinDMA (Benchmark) | 1,2-Dilinoleyloxy-3-dimethylaminopropane | ~1 | |
| DLinTMA.Cl | 1,2-Dilinoleyloxy-3-trimethylaminopropane chloride | 2-5 | |
| DLinMPZ | 1,2-Dilinoleyloxy-3-(N-methylpiperazino)propane | 2-5 | |
| DLinMA | 1,2-Dilinoleyloxy-3-morpholinopropane | 12-25 | |
| DLin-EG-DMA | 1,2-Dilinoleyloxy-3-(2-N,N-dimethylamino)ethoxypropane | 5-12 | |
| DLinDAC | 1,2-Dilinoleyloxy-3-(dimethyalmino)acetoxypropane | 5-12 | |

TABLE 4

Linker modifications to DLinDMA

| Abbreviated Name | Chemical Name | $ED_{50}$ (mg/kg) | Structure |
|---|---|---|---|
| DLinDMA (Benchmark) | 1,2-Dilinoleyloxy-3-dimethylaminopropane | ~1 | 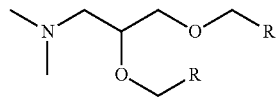 |
| DLinDAP | 1,2-Dilinoleoyl-3-dimethylaminopropane | 40-50 | 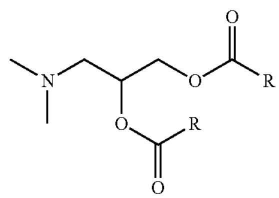 |
| DLin-2-DMAP | 1-Linoleoyl-2-linoeyloxy-3-dimethylaminopropane | 5-12 | 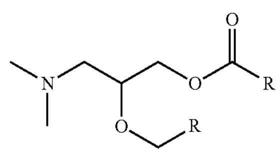 |
| DLin-C-DAP | 1,2-Dilinoleylcarbamoyloxy-3-dimethylaminopropane | 12-25 | 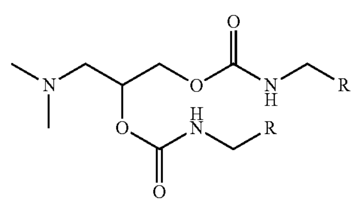 |
| DLin-S-DMA | 1,2-Dilinoleylthio-3-dimethylaminopropane | 12-25 | 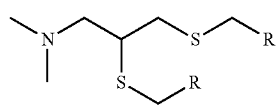 |
| DLin-K-DMA | 2,2-Dilinoleyl-4-dimethylaminomethyl-[1,3]-dioxolane | ~0.4 | 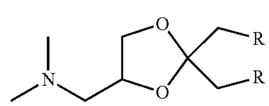 |

R = (linoleyl chain structure)

The first modification listed in Table 4 is DLinDAP, in which esters replace the ethoxy linkers of DLinDMA. Remarkably, nucleic acid lipid particles comprising Factor VII siRNA and containing DLinDAP showed significantly reduced in vivo activity as compared to those containing DLinDMA ($ED_{50}$ 12-25 mg/kg), despite its very similar structure to DLinDMA. Further, nucleic acid-lipid particles based on DLin-2-DMAP, a lipid with one ethoxy linkage and one ester linkage, yielded activity intermediate between DLinDAP- and DLinDMA-based nucleic acid-lipid particles. Nucleic acid-lipids particles based on lipids containing carbamate (DLin-C-DAP) or thioether (DLin-S-DMA) linkages also resulted in dramatically reduced in vivo activity.

The final modification was to insert a ketal ring linker, which introduced interesting structural changes to the lipid molecule. First, the ketal is known to be more acid labile than ethoxy linkers (Martin, B. et al., Curr. Pharm. Des 11:375-394 (2005)), which may decrease its half-life in the endocytic pathway. Second, the hydrocarbon chains now bond to the linker group through a single carbon. Interestingly, the introduction of a ketal ring linker into DLinDMA resulted in nucleic acid-lipid particles that were ~2.5-fold more potent in reducing serum FVII protein levels relative to the DLinDMA benchmark, with an $ED_{50}$ (i.e., dose to achieve 50% gene silencing) of ~0.4 mg/kg versus 1 mg/kg, respectively (FIG. 2).

Screen 1c: Reduce Unsaturation of DLinDMA Hydrocarbon Chains, Miscellaneous Modifications and In Vivo FVII Activity A variety of other cationic lipids containing modifications as compared to DLinDMA were tested in the Factor VII knockdown system. For example, the propensity of lipid molecules to adopt inverted non-bilayer phases is known to increase with increasing hydrocarbon chain unsaturation (Cullis, P. R., et al., Chem. Phys. Lipids 40:127-144 (1986)). Given the hypothesis that formation of these non-bilayer phases is responsible for endosome disruption and release of siRNA into the cytoplasm and the observation that SNALP activity in vitro also increases with increasing unsaturation (Heyes, J. et al., J. Control Release 107:276-287 (2005)), it was of interest to see what happened to LN-siRNA potency in vivo when DLinDMA, containing two C18:2 chains was replaced by DODMA, with two C18:1 chains. These cationic lipids and the results of these experiments are shown in Table 5.

TABLE 5

Miscellaneous modifications to headgroup, linker and hydrocarbon chains

| Abbreviated Name | ED$_{50}$ (mg/kg) | Modification |
|---|---|---|
| DLinDMA (Benchmark) | ~1 | 1,2-Dilinoleyloxy-3-dimethylaminopropane |
| DODMA | 2-5 | 1,2-Dioleyloxy-3-dimethylaminopropane |
| DODAP | >25 | $C_{41}H_{77}NO_4$<br>1,2-Dioleoyl-3-dimethylaminopropane |
| DO-C-DAP | >10 | 1,2-Dioeylcarbamoyloxy-3-dimethylaminopropane |
| DMDAP | >10 | 1,2-Dimyristoleoyl-3-dimethylaminopropane |
| DLinTAP.Cl | >25 | 1,2-Dilinoleoyl-3-trimethylaminopropane chloride |

TABLE 5-continued

Miscellaneous modifications to headgroup, linker and hydrocarbon chains

| Abbreviated Name | $ED_{50}$ (mg/kg) | Modification |
|---|---|---|
| DOTAP.Cl | >25 | $C_{42}H_{80}ClNO_4$<br>1,2-Dioleoyl-3-trimethylaminopropane chloride |
| DLinAP | 5-12 | 3-(N,N-Dilinoleylamino)-1,2-propanediol |

As shown in Table 5, DODMA was 2 to 5-fold less active than the more unsaturated DLinDMA, and substituting ether linkages for esters (DODAP) decreased activity more than 25-fold.

Carbamate linked C18:1 chains (DO-C-DAP) were also an inactive combination at 10 mg/kg, the maximum dose tested. DMDAP was synthesized to determine if the shorter C14:1 hydrocarbon chains might enable the ester-linked lipid through enhanced lipid mixing with the target endosomal membrane (Mui, B. et al., *Biochim. Biophys. Acta* 1467:281-292 (2000)); however, no activity was observed for DMDAP-LN-siRNA in the FVII model up to a maximum dose of 10 mg/kg. The permanently charged, ester linked lipids DLin-TAP and DOTAP were of interest, because the latter lipid is one of the most commonly used cationic lipids for transfection. However, in the LN-siRNA model, neither of these ester-linked lipids showed any signs of activity, ($ED_{50}$>25 mg/kg). The last lipid represented a radical structural change to DLinDMA, in which the dimethylpropane headgroup was reversed and the hydrocarbon chains bond directly to the amino nitrogen, leaving a dihydroxy headgroup; however, DLinAP showed poor activity with an $ED_{50}$ in the 5-12 mg/kg range.

In summary, the incremental modifications to DLinDMA successfully identified DLin-K-DMA as a cationic lipid that is significantly more potent than DLinDMA when tested head-to-head in the same in vivo model and LN-siRNA formulation.

Screen 2a: Headgroup Modifications to DLin-K-DMA and In Vivo FVII Activity

Given the importance of positive charge in the mechanism of action hypothesis guiding the lipid design, the effects of structural changes in the amine-based headgroup were investigated in the context of DLin-K-DMA as the new benchmark lipid. A series of headgroup modifications were made, characterized, and tested to explore the effect of size, acid dissociation constant, and number of ionizable groups (Table 6).

TABLE 6

Headgroup modifications to DLin-K-DMA

| Abbreviated Name | Chemical Name | $ED_{50}$ (mg/kg) | Modification |
|---|---|---|---|
| DLin-K-DMA (Benchmark) | 2,2-Dilinoleyl-4-dimethylamino methyl-[1,3]-dioxolane | ~0.4 | |
| DLin-K-MPZ | 2,2-Dilinoleyl-4-N-methyl piperazino-[1,3]-dioxolane | ~1.5 | |
| DLin-K-MA | 2,2-Dilinoleyl-4-N-morpholino-[1,3]-dioxolane | >15 | |

TABLE 6-continued

Headgroup modifications to DLin-K-DMA

| Abbreviated Name | Chemical Name | ED$_{50}$ (mg/kg) | Modification |
|---|---|---|---|
| DLin-K-TMA.Cl | 2,2-Dilinoleyl-4-trimethylamino-[1,3]-dioxolane Chloride | >5[a] | |
| DLin-K$^2$-DMA | 2,2-Dilinoleyl-4,5-bis(dimethylamino methyl)-[1,3]-dioxolane | ~0.4 | |
| DLin-K-C2-DMA | 2,2-Dilinoleyl-4-(2-dimethyl aminoethyl)-[1,3]-dioxolane | ~0.1 | |
| DLin-K-C3-DMA | 2,2-Dilinoleyl-4-(3-dimethyl aminopropyl)-[1,3]-dioxolane | ~0.6 | |
| DLin-K-C4-DMA | 2,2-Dilinoleyl-4-(4-dimethyl aminobutyl)-[1,3]-dioxolane | >3 | |

[a]No activity observed at 5 mg/kg and lethal at next dose of 15 mg/kg

DLin-K-DMA contains a chiral carbon at position 4 of the ketal ring structure. Therefore, the two optically pure (+) and (−) enantiomers were synthesized and their activities compared to that of the racemic mixture. All three formulations exhibited indistinguishable dose responses, each with an ED$_{50}$~0.3 mg/kg.

The first three modifications listed in Table 6 were also applied to DLinDMA in screen 1, the introduction of piperazino (DLin-K-MPZ) and morpholino (DLin-K-MA) amino moieties to modify the characteristics of the ionizable positive charge, and also converting the tertiary dimethylamine into the permanently charged quaternary amine of DLin-K-TMA. Although all these modifications significantly decreased activity, it is interesting to note that DLin-K-MPZ, with an ED$_{50}$~1.5, was almost as active as DLinDMA but approximately 5-fold less active than DLin-K-DMA, and the same modification to DLinDMA reduced its activity by a similar factor. Furthermore, the morpholino amine function made DLin-K-MA inactive at the maximum dose tested (15 mg/kg) similar to DLinMA, which has an ED$_{50}$ of 12-25 mg/kg. Another observation of note is that DLin-K-TMA (permanent positive charge) is toxic. No activity was observed at 5 mg/kg, but animals experienced significant weight loss (data not shown) and did not survive the next dose at 15 mg/kg.

The modification abbreviated as DLin-K$^2$-DMA denotes the presence of two dimethylamine moieties. Within error, this lipid had the same activity as DLin-K-DMA, despite the larger headgroup.

Figure 2A:
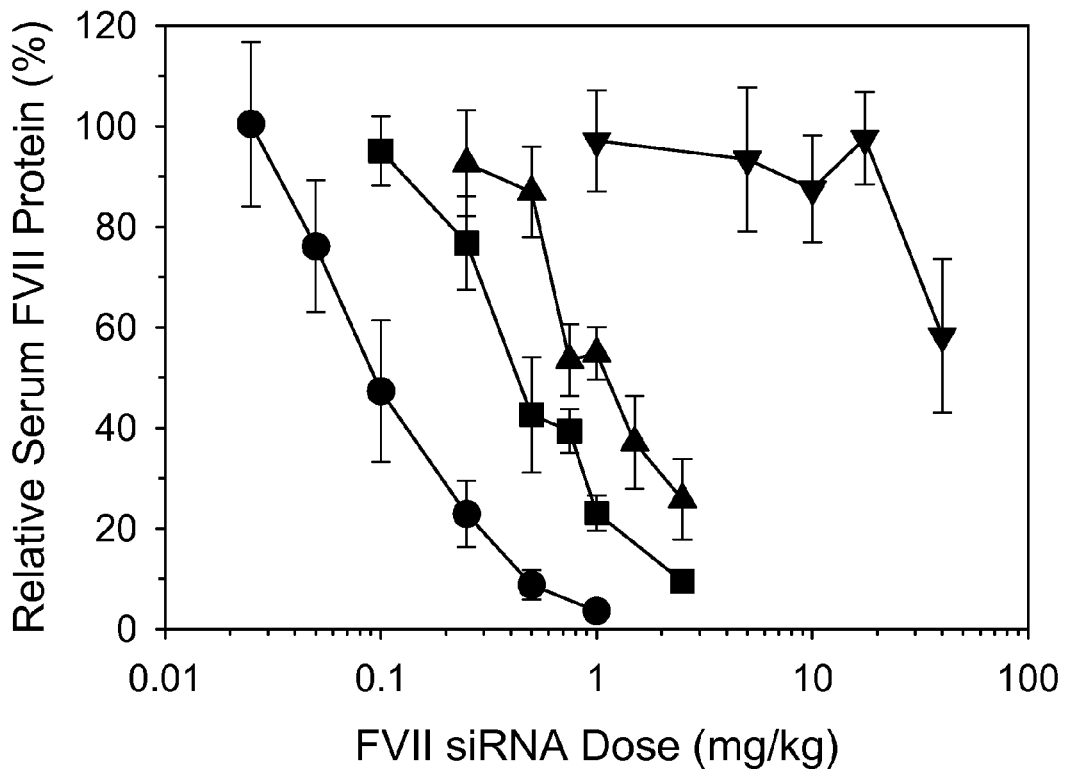
FIGS. 2A-B are graphs depicting the in vivo silencing activity of nucleic acid-lipid particles comprising various cationic lipids.
Figure 2B:
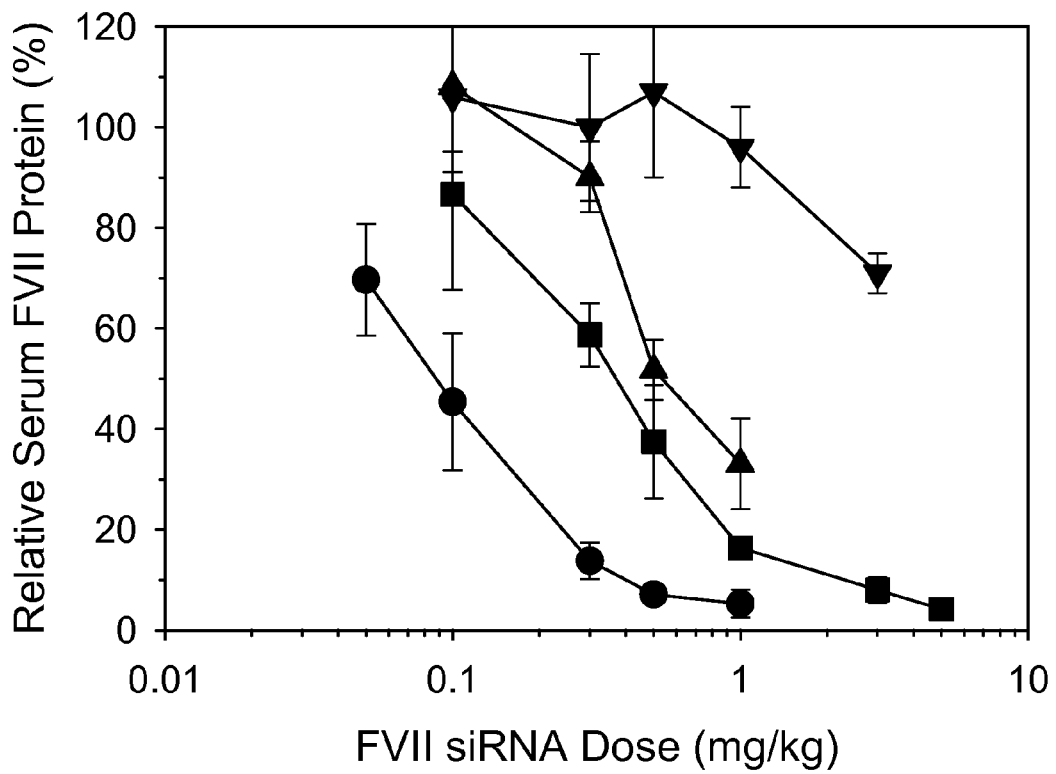

As an additional parameter, the distance between the dimethylamino group and the dioxolane linker was varied by introducing additional methylene groups. The remaining three lipids were closely related in structure, and were synthesized to determine what effect distancing the positive charge from the dioxolane ring had on activity. This parameter can affect both the pK$_a$ of the amine headgroup as well as the distance and flexibility of the charge presentation relative to the lipid bilayer interface. Inserting a single additional methylene group into the headgroup (DLin-K-C2-DMA) produced a dramatic increase in potency relative to DLin-K-DMA. The ED$_{50}$ for this lipid was ~0.1 mg/kg, making it 4-fold more potent than DLin-K-DMA and 10-fold more potent than the DLinDMA benchmark when compared head-to-head in the FVII model (FIG. 2A). Additional methylene groups decreased activity with a significant reduction occurring between DLin-K-C3-DMA (ED$_{50}$~0.6 mg/kg) and DLin-K-C4-DMA (ED$_{50}$>3 mg/kg) (FIG. 2B).

Screen 2b: Modifications to the Headgroup, Linker and Hydrocarbon Chains of DLin-K-DMA and In Vivo FVII Activity A number of additional structural modifications made to DLin-K-DMA are presented in Table 7. The first three in the series confirmed the importance of hydrocarbon chain unsaturation for in vivo activity. A progressive decrease in $ED_{50}$'s from ~0.3, to ~1.0 and ~8.0 mg/kg was observed going from DLin-K-DMA (C18:2) to DO-K-DMA (C18:1) and DS-K-DMA (C18:0), respectively. The next modification (DLin-K6-DMA) demonstrated that the 5-membered ketal ring of DLin-K-DMA could be substituted by a 6-membered dioxolane ring structure without loss of activity. The final lipid shown in Table 7 represented a more radical modification. DLin-M-DMA does not have a ketal ring linker, but the hydrocarbon chains still bond directly with a single carbon. Interestingly, this lipid remained relatively active with an $ED_{50}$~0.7 mg/kg.

Figure 3:
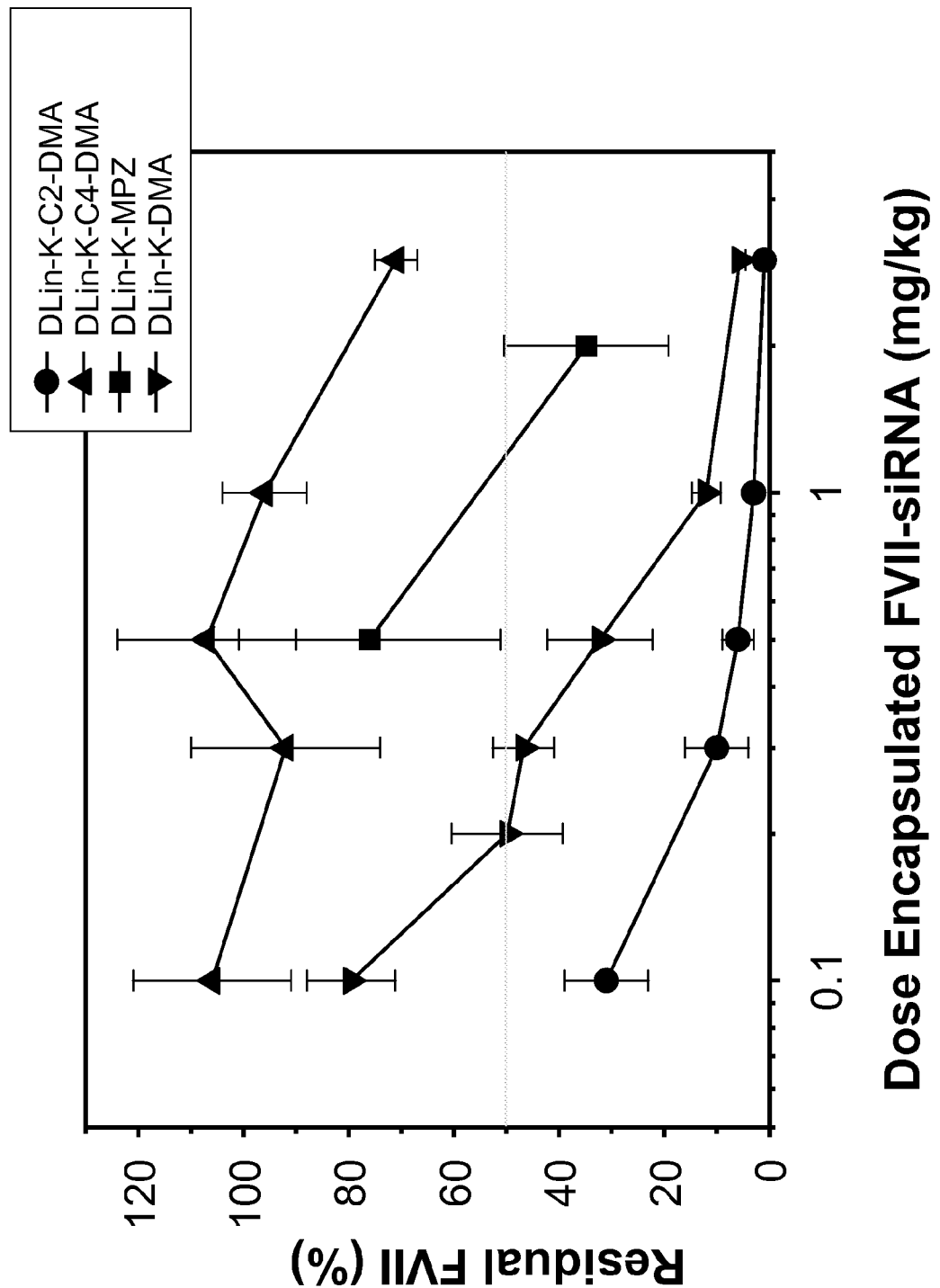
FIG. 3 is a graph depicting the amount of residual FVII following administration of various dosages of the indicated nucleic acid-lipid particle formulations comprising encapsulated FVII siRNA to mice.
Figure 4:
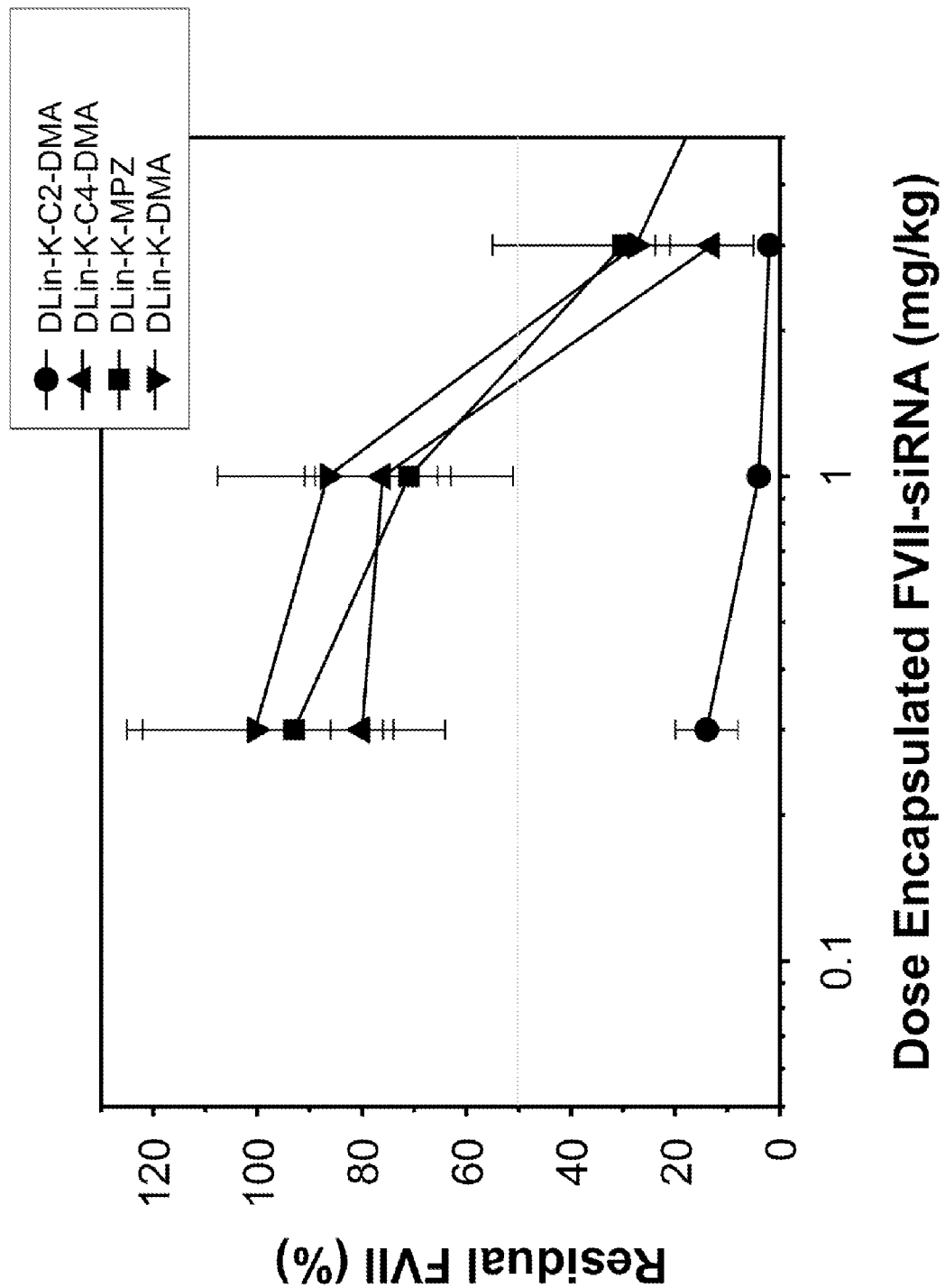
FIG. 4 is a graph depicting the amount of residual FVII following administration of various dosages of the indicated nucleic acid-lipid particle formulations comprising encapsulated FVII siRNA to rats.
Figure 5:
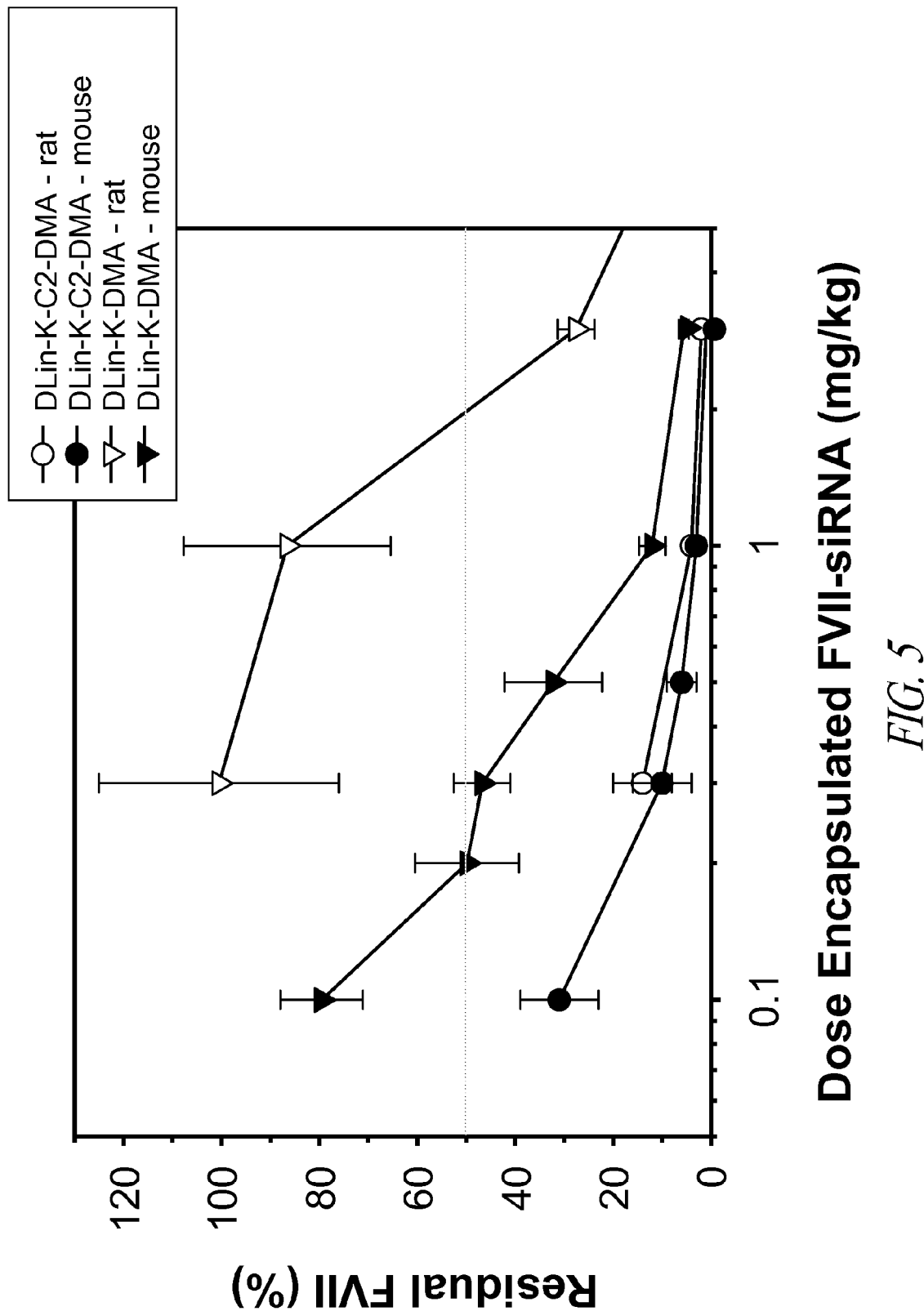
FIG. 5 is a graph comparing the amount of residual FVII following administration of two nucleic acid-lipid particle formulations (DLin-K-C2-DMA or DLin-K-DMA) comprising encapsulated FVII siRNA to mice or rats.

PEG-lipid. The formulations initially tested (which included either DLin-K-DMA, DLin-K-MPZ, DLin-K-C2-DMA, or DLin-K-C4-DMA) reduced residual FVII levels in both mice (FIG. 3) and rats (FIG. 4). However, the DLin-K-C2-DMA formulation showed a remarkably enhanced ability to reduce FVII levels in both mice and rats. The activity of the DLin-K-C2-DMA formulation was approximately 2-3-fold greater than the DLin-K-DMA formulation in mice, and approximately 10-20-fold greater than the DLin-K-DMA formulation in rats. A comparison of FVII reduction in mice and rats using the DLin-K-DMA formulation or the DLin-K-C2-DMA formulation is shown in FIG. 5. Formulations having

TABLE 7

Miscellaneous modifications to headgroup, linker and hydrocarbon chains of DLin-K-DMA

| Abbreviated Name | $ED_{50}$ (mg/kg) | Modification |
|---|---|---|
| DLin-K-DMA (Benchmark) | ~1 | 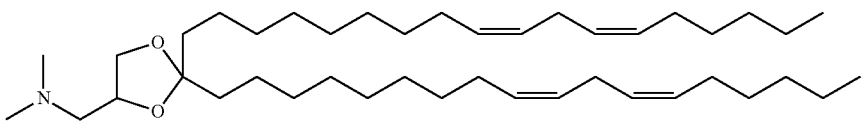 2,2-Dilinoleyl-4-dimethylaminomethyl-[1,3]-dioxolane |
| DO-K-DMA | ~1.0 | 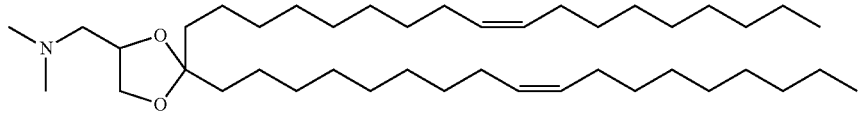 2,2-Dioleoyl-4-dimethylaminomethyl-[1,3]-dioxolane |
| DS-K-DMA | ~8.0 | 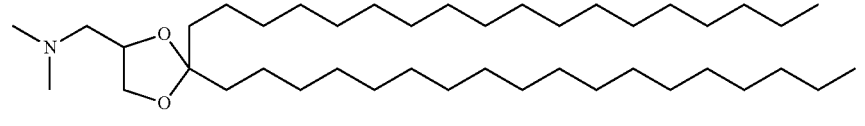 2,2-Distearoyl-4-dimethylaminomethyl-[1,3]-dioxolane |
| DLin-K6-DMA | ~0.3 | 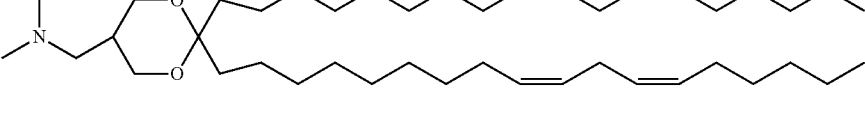 2,2-Dilinoleyl-5-dimethylaminomethyl-[1,3]-dioxolane |
| DLin-M-DMA | ~0.7 | 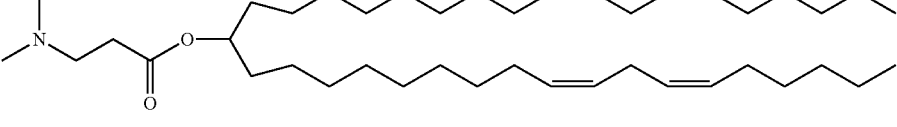 Dilinoleylmethyl-3-dimethylaminopropionate |

Comparison of the In Vivo Activity of Nucleic Acid-Lipid Formulations in Mice and Rats The ability of various nucleic acid-lipid formulations comprising different cationic lipids was further explored in mice and rats. Each of the tested nucleic acid-lipid formulations was prepared as described above using PEG-C-DOMG as the DLin-K-C4-DMA or DLin-K-MPZ (MPZ) as the cationic lipid showed similar activity to each other and to the DLinDMA formulation.

Figure 6:
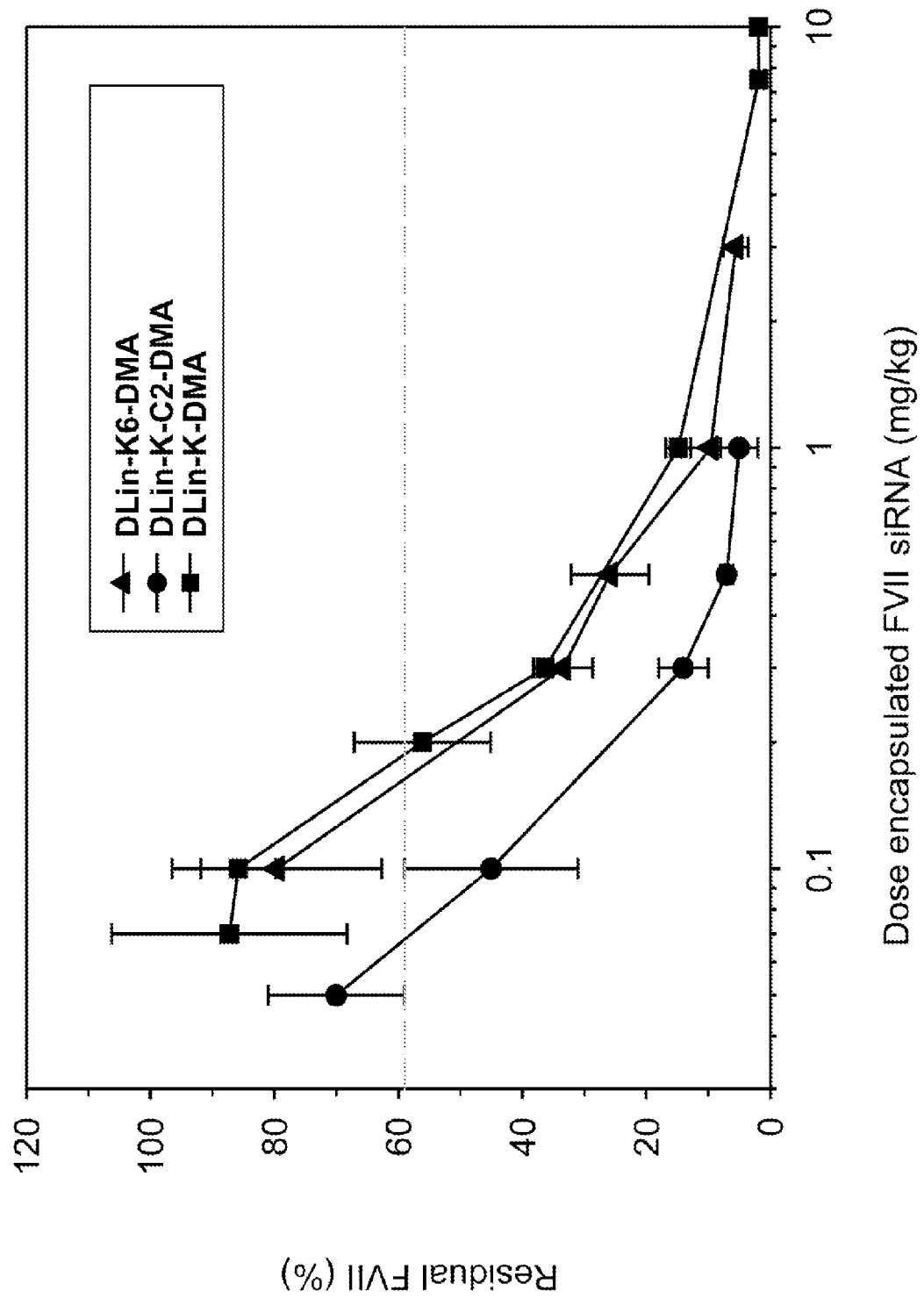
FIG. 6 is a graph comparing the amount of residual FVII following administration of various concentrations of three different nucleic acid-lipid particle formulations (DLin-K6-DMA, DLin-K-C2-DMA, and DLin-K-DMA) comprising encapsulated FVII siRNA to mice.
Figure 7:
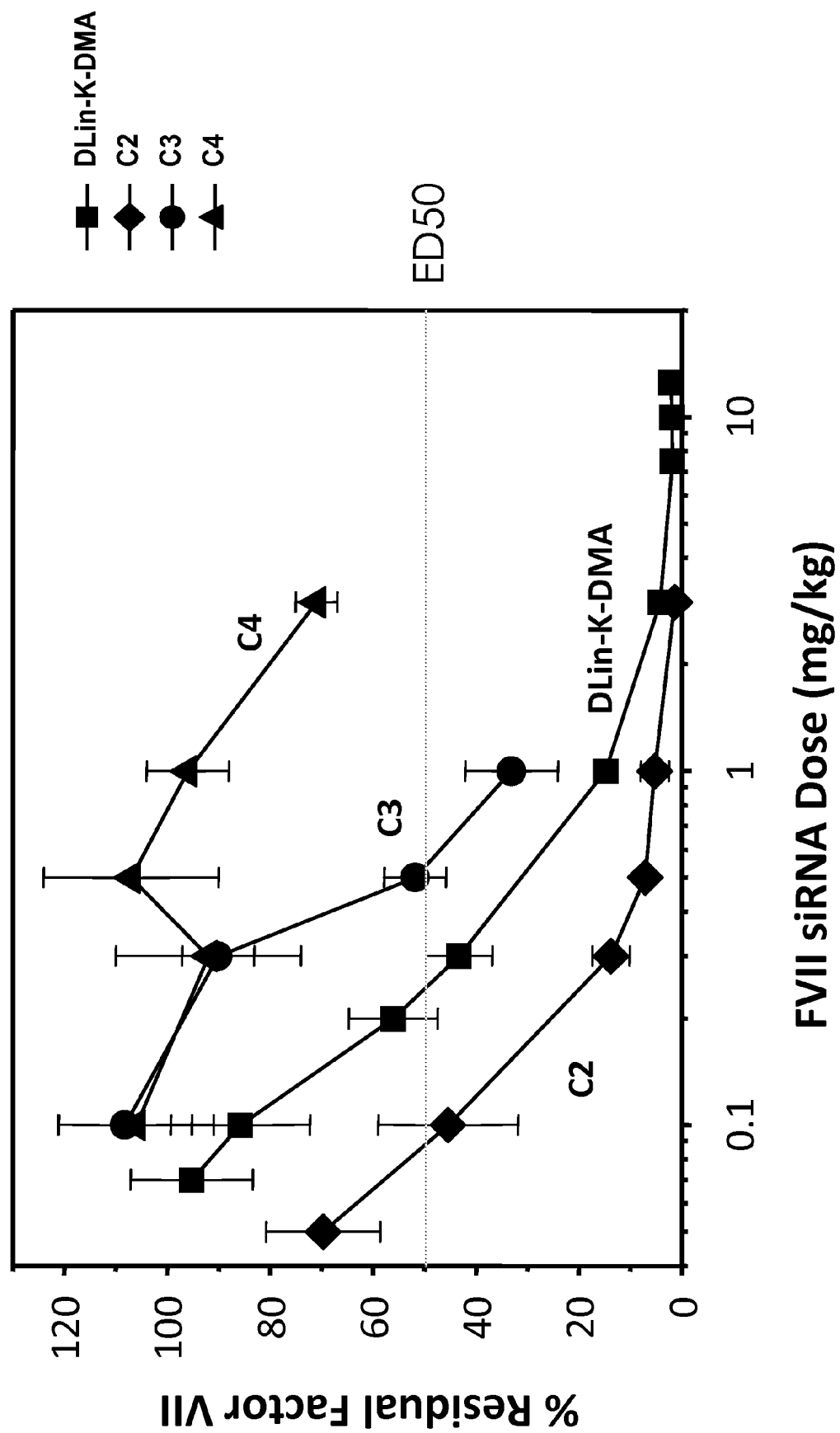
FIG. 7 is a graph depicting the amount of residual FVII following administration of various dosages of the indicated nucleic acid-lipid particle formulations comprising encapsulated FVII si RNA to animals. C2 indicates DLin-K-C2-DMA; C3 indicates DLin-K-C3-DMA; and C4 indicates DLin-K-C4-DMA.

The liposomal formulation having DLin-K6-DMA as the cationic lipid was also tested in comparison to DLin-K-C2-DMA and DLin-K-DMA. The DLin-K6-DMA formulation reduced FVII levels in mice similarly to DLin-K-DMA, as shown in FIG. 6.

Pharmacokinetics and Liver Accumulation of Cationic LN-siRNA Formulations

The correlation between levels of siRNA delivered to the liver and FVII reduction was determined by encapsulating Cy-3 labeled siRNA in the selection of LN-siRNA systems covering a spectrum of in vivo activities shown in Table 8. Cy-3 fluorescence was measured in plasma and liver tissue 0.5 and 3.0 h post injection. The plasma data indicated a wide variety of clearance rates at the early time point, but for the majority of the formulations, 20-50% of the injected siRNA dose was recovered in the liver within 0.5 h, whether they were highly active or exhibited poor activity. The most active formulations, DLinDMA and DLin-K-DMA, showed relatively high levels of siRNA in the liver at 0.5 h, 50% and 32% respectively. All formulations showed a decrease in liver Cy-3 levels after 3 h, which presumably reflected metabolism. This study suggests that gross delivery to the liver alone does not explain differences in activity.

TABLE 8

Plasma and liver concentrations of Cy-3 siRNA for a selection of active and inactive cationic lipid-containing LN-siRNA systems

| Lipid | 0.5 h (% injected dose) | | 3.0 h (% injected dose) | | $ED_{50}$ (mg/kg) |
|---|---|---|---|---|---|
| | Plasma | Liver | Plasma | Liver | |
| DLin-K-DMA | 1.1 | 32.0 | 0.4 | 4.0 | 0.3 |
| DLinDMA | 15.3 | 50.0 | 0.7 | 17.0 | 1.0 |
| DLinMPZ | 20.3 | 52.0 | 0.4 | 37.5 | 2-5 |
| DLinAP | 86.2 | 11.5 | 23.1 | 5.0 | 5-12 |
| DLin-2-DMAP | 17.5 | 20.5 | 8.8 | 2.5 | 5-12 |
| DLinDAC | 27.1 | 29.0 | 0.3 | 6.5 | 12-25 |
| DLinDAP | 46.6 | 20.5 | 3.3 | 16.5 | 12-25 |
| DLin-C-DAP | 69.4 | 28.5 | 19.0 | 13.5 | 12-25 |
| DLin-S-DMA | 10.7 | 2.5 | 5.4 | 0 | 12-25 |
| DLinMA | 20.2 | 10.5 | 0.4 | 4.5 | 12-25 |

Tolerability of DLin-K-C2-DMA-Containing LN-siRNA Systems

Rats administered the liposomal formulation containing DLin-K-C2-DMA showed a dose-dependent loss of weight. Rats administered 91 mg/kg appeared normal and had normal livers. Rats administered 182 mg/kg showed slower movement and a scruffy coat. Their livers were slightly pale, and one of three livers showed some slight mottling. Of the rats administered 364 mg/kg, one died, and they showed hunched, slower movement, quinting eyes, scruffy coats, piloerection, red/orange urine, with pale and some mottling livers. Rats showed significant increases in ALT/AST, as low as 182 mg/kg lipid.

Histopathology results for livers obtained from rats treated with 91 mg/kg ("5" mg/kg) were normal. The livers of rats treated with 182 mg/kg ("10" mg/kg) showed mild to moderate hepatocellular necrosis, centrilobular, and hepatocellular vacuolization. One of the livers of the surviving rats treated with 364 mg/kg ("20" mg/kg) showed moderate hepatocellular necrosis, centrilobular, and the other showed diffuse, mild to moderate hepatocellular necrosis (not concentrated in centrilobular region) with mild inflammation.

Mice treated with the liposomal formulation of DLin-K-C2-DMA also showed a dose-dependent loss of weight, although no mice died. Mice also showed a greater than 10-fold increase in ALT-AST at approximately 1100 mg/kg lipid. However, the mice showed no obvious clinical signs, except at greater than 1300 mg/kg, where the mouse exhibited hunched, slower movement and a scruffy coat.

The introduction of a ketal linker did not appear to impart any significant toxicity issues in mice and, in fact, the LN systems containing DLin-K-DMA and encapsulating FVII siRNA were extraordinarily well tolerated in mice. The data presented in Table 9 are from a study designed to determine appropriate dosing ranges, and extreme, single doses of lipid and siRNA were achieved. The toxicity criteria measured were % change in body weight and serum levels of the liver enzyme markers, ALT and AST.

TABLE 9

Key tolerability parameters for DLin-K-DMA-containing LN-siRNA systems in mice at extreme doses

| siRNA (mg/kg) | Total Lipid (mg/kg) | % Change Body Weight | ALT (IU/L) | AST (IU/L) |
|---|---|---|---|---|
| 0-10 | 0-164 | 0 | 45 | 90 |
| 46 | 750 | −5.0 | 174 | 340 |
| 61 | 1000 | −4.5 | 448 | 816 |
| 76 | 1250 | −5.5 | 1771 | 4723 |
| 92 | 1500 | −6.0 | 4723 | 2094 |

Compared to saline controls, no changes in blood chemistry or body weight were observed up to an siRNA dose of 10 mg/kg, which for this formulation was >30-fold greater than the $ED_{50}$ dose.

A massive siRNA dose of 46 mg/kg (150-fold more than the $ED_{50}$) was administered before significant toxicity signs were measured. This siRNA dose translated to a total lipid dose of 750 mg/kg at the siRNA-to-lipid ratio of 0.06 (wt/wt). Even at these levels, the increases in serum ALT and AST were relatively modest (<10-fold normal), and it is not until siRNA doses exceeded 61 mg/kg that severe (>10-fold) increases are observed. The maximum dose tested was 92 mg siRNA/kg, equivalent to 1500 mg total lipid/kg. Animals lost 6% body weight but no deaths occurred at any of the doses tested.

Characterization of Nucleic Acid-Lipid Particles

Characteristics of selected nucleic acid-lipid formulations are summarized in Table 10, wherein C2 indicates that the cationic lipid is DLin-K-C2-DMA; C4 indicates that the cationic lipid is DLin-K-C4-DMA; and MPZ indicates that the cationic lipid is DLin-K-MPZ. Each of the formulations described below contained PEG-C-DOMG as the PEG-lipid.

TABLE 10

Characteristics of Formulations Comprising Various Amino Lipids

| Formulation | Final Lipid Ratio (mol %) | | | | Particle Size (nm) | Final D/L Ratio (wt/wt)* | % Free siRNA |
|---|---|---|---|---|---|---|---|
| | Cat | DSPC | Chol | PEG-C-DOMG | | | |
| C2 | 37.4 | 11.5 | 41.3 | 9.8 | 72 ± 23 | 0.037 | 7.8 |
| C4 | 37.9 | 9.6 | 42.8 | 9.7 | 64 ± 15 | 0.058 | 1.2 |
| MPZ | ND | ND | ND | ND | 71 ± 21 | 0.056** | 5.1 |

*Based on encapsulated material;
**estimated from DSPC, Chol, PEG-C-DOMG results Apparent pKa's of Key Cationic Lipids Measured In Situ in LN-siRNA Formulations Two important parameters underlying the lipid design are the $pK_a$ of the ionizable cationic lipid and the abilities of these lipids, when protonated, to induce a non-bilayer (hexagonal $H_{II}$) phase structure when mixed with anionic lipids. The $pK_a$ of the ionizable cationic lipid determines the surface charge on the LNP under different pH conditions. The charge state at physiologic pH (e.g., in circulation) can influence plasma protein adsorption, blood clearance and tissue distribution behavior (Semple, S. C., et al., *Adv. Drug Deliv Rev* 32:3-17 (1998)), while the charge state at acidic pH (e.g., in endosomes) can influence the ability of the LNP to combine with endogenous anionic lipids to form endosomolytic non-bilayer structures (Hafez, I. M., et al., Gene Ther 8:1188-1196 (2001)). Consequently, the ability of these lipids to induce $H_{II}$ phase structure in mixtures with anionic lipids is a measure of their bilayer destabilizing capacity and relative endosomolytic potential.

The fluorescent probe 2-(p-toluidino)-6-napthalene sulfonic acid (TNS), which exhibits increased fluorescence in a hydrophobic environment, can be used to assess surface charge on lipid bilayers. Titrations of surface charge as a function of pH can then be used to determine the apparent $pK_a$ (hereafter referred to as $pK_a$) of constituent lipids (Cullis, P. R., et al., *Chem Phys Lipids* 40:127-144 (1986)). Using this approach, the $pK_a$ values for nucleic acid-lipid particles containing various cationic lipids were determined and are summarized in Table 11. The relative ability of the protonated form of certain ionizable cationic lipids to induce $H_{II}$ phase structure in anionic lipids was ascertained by measuring the bilayer-to-hexagonal $H_{II}$ transition temperature ($T_{BH}$) in equimolar mixtures with distearoylphosphatidylserine (DSPS) at pH 4.8, using $^{31}P$ NMR (Cullis, P. R. and de Kruijff, B., *Biochim Biophys Acta* 513:31-42 (1978)) and differential scanning calorimetric (DSC) analyses (Expand, R. M. et al., *Biochemistry* 28:9398-9402 (1989)). Both techniques gave similar results.

The data presented in Table 11 indicate that the highly active lipid DLin-K-C2-DMA has $pK_a$ and $T_{BH}$ values that are theoretically favorable for use in siRNA delivery systems. The $pK_a$ of 6.4 indicates that LNPs based on DLin-KC2-DMA have limited surface charge in circulation, but will become positively charged in endosomes. Further, the $T_{BH}$ for DLin-K-C2-DMA is 7° C. lower than that for DLinDMA, suggesting that this lipid has improved bilayer destabilizing capacity. However, the data also demonstrate that $pK_a$ and $T_{BH}$ do not fully account for the in vivo activity of lipids used in LNPs. For example, DLin-K-C3-DMA and DLin-K-C4-DMA have identical $pK_a$ and $T_{BH}$ values, yet DLin-KC4-DMA is more than 5-fold less active in vivo. Moreover, DLin-K-C2-DMA and DLin-K-C4-DMA, which have very similar $pK_a$ and $T_{BH}$ values, exhibit a >30-fold difference in in vivo activity. Thus, while the biophysical parameters of $pK_a$ and $T_{BH}$ are useful for guiding lipid design, the results presented in Table 11 support the strategy of testing variants of lead lipids, even ones with very similar $pK_a$ and $T_{BH}$ values.

TABLE 11 pKa's of key cationic lipids measured in situ in preformed vesicles using TNS fluorescence titrations

| Cationic Lipid | Apparent pKa | $H_{II}$ transition temperature (° C.) | FVII $ED_{50}$ (mg/kg) |
| --- | --- | --- | --- |
| DLin-K-C3-DMA | 6.8 | 18 | ~0.6 |
| DLin-K-C4-DMA | 6.8 | 18 | >3.0 |
| DLinDMA | 6.4 | 27 | ~1.0 |
| DLin-K-C2-DMA | 6.4 | 20 | ~0.1 |
| DLin-K6-DMA | 6.2 | n.d. | ~0.3 |
| DLin-K-MPZ | 6.2 | n.d. | ~1.5 |
| DLinDAP | 5.7 | 26 | >25 |
| DLin-K-DMA (racemic mixture) | 5.6 | n.d. | ~0.3 |
| DLin-K-MA | 5.6 | n.d. | >15 |
| DLin-K-DMA | 5.6 | 19 | ~0.4 |

As shown above, the potency of LN-siRNA systems containing 40 mole % DLin-K-C2-DMA was such that as little as ~100 picomoles of encapsulated siRNA administered as a single i.v. bolus to a mouse was sufficient to knockdown serum concentrations of FVII protein by 50% within 24 h of injection.

In this study, the ratios of lipid components and siRNA-to-lipid were kept constant for all formulations, so that any differences in surface charge could be attributed to cationic lipid pKa. The siRNA-to-lipid ratio used in the activity screen was 0.06 wt/wt, which means that positive charge was in excess of negative charge. Charge neutralization for formulations containing 40 mole % monobasic cationic lipid occurs at a ratio of approximately 0.17 wt/wt. Consequently, assuming one cationic lipid forms an ion pair with each negative charge on the siRNA backbone, then approximately 35% of the total cationic lipid was associated with siRNA inside the nanoparticle and, therefore, could not contribute to surface charge. Interestingly, increasing the siRNA-to-lipid ratio above ~0.08 (wt/wt) in a 40/10/40/10 formulation decreased the potency of LN-siRNA systems (data not shown). A similar response has been reported for siRNA delivered in vivo using lipidoid nanoparticles (A. Akinc, M. et al., Mol. Ther. (2009) and may reflect the importance of free cationic lipid (lipid not associated with siRNA) and/or the total cationic lipid dose injected.

One of the most striking observations was the dependence of activity on the extent of hydrocarbon chain unsaturation. For both DLinDMA and DLin-K-DMA, there was a significant decrease in potency for each drop in the number of double bonds. Without wishing to be bound by theory, it is proposed that (active) synthetic cationic lipid inserted into the endosomal membrane and endogenous anionic phospholipids (such as phosphatidylserine) form ion pairs (Hafez, I. M., et al., *Gene Ther.* 8:1188-1196 (2001) and Xu, Y. and Szoka, F. C., *Biochemistry* 35:5616-5623 (1996)). The resulting charge neutralization effectively reduces the cross-sectional area of the combined headgroups, which corresponds to a substantial decrease in their intrinsic radius of curvature. Applying the molecular shape arguments employed to describe lipid polymorphism, this means the cationic and anionic lipids go from a cylindrical shape they adopt in isolation to a cone shape formed by the neutral ion pair. Cylindrical shaped lipids are compatible with bilayer structure, whereas cone shaped lipids are not Cullis, P. R. et al., *Chem. Phys. Lipids* 40:127-144 (1986) and Hafez, I. M. and Cullis, P. R., *Adv. Drug Deliv. Rev.* 47:139-148 (2001)), they prefer to adopt inverted lipid phases, such as the hexagonal $H_{II}$ phase, that disrupt bilayer structure. As a consequence, the endosome membrane is lysed, enabling siRNA to access the cytoplasm where it can engage RISC and cleave FVII mRNA.

The results described herein are consistent with the shape concept introduced above, because adding cis double bonds to a given chain length increased the cross-sectional area swept out by the terminal methyl groups, thus promoting cone-like geometry. The propensity to adopt non-bilayer structures when paired with anionic phospholipids is also a plausible rationale for why the ketal-containing lipid family is so active. Both hydrocarbon chains bond through a single carbon into the ketal ring linker, the tetrahedral bond angle will tend to splay the chains apart favoring a cone shape.

were observed daily, and body weights, serum chemistry, and hematology parameters were measured at 72 hours post-dose. As shown in Table 12, KC2-SNALP was very well tolerated at the high dose levels examined (relative to the observed $ED_{50}$ dose) with no dose-dependent, clinically significant changes in key serum chemistry or hematology parameters.

TABLE 12

Clinical chemistry and hematology parameters in rats

| Vehicle | siRNA dose (mg/kg) | ALT (U/L) | AST (U/L) | Total Bilirubin (mg/dL) | BUN (mg/dL) | RBC (×10$^6$/μL) | Hemoglobin (g/dL) | WBC (×10$^3$/μL) | PLT (×10$^3$/μL) |
|---|---|---|---|---|---|---|---|---|---|
| PBS | | 56 ± 16 | 109 ± 31 | 2 ± 0 | 4.8 ± 0.8 | 5.5 ± 0.3 | 11.3 ± 0.4 | 11 ± 3 | 1166 ± 177 |
| KC2-SNALP | 1 | 58 ± 22 | 100 ± 14 | 2 ± 0 | 4.4 ± 0.6 | 5.6 ± 0.2 | 11.6 ± 0.6 | 13 ± 2 | 1000 ± 272 |
| KC2-SNALP | 2 | 73 ± 9 | 81 ± 10 | 2.2 ± 0.4 | 4.3 ± 0.6 | 5.9 ± 0.3 | 11.6 ± 0.3 | 13 ± 4 | 1271 ± 269 |
| KC2-SNALP | 3 | 87 ± 19 | 100 ± 30 | 2 ± 0 | 5.0 ± 0.8 | 6.0 ± 0.2 | 11.9 ± 0.4 | 15 ± 2 | 958 ± 241 |

Example 17

Efficacy and Tolerability of the DLin-K-C2-DMA SNALP Formulation

The efficacy and tolerability of nucleic acid lipid particles comprising DLin-K-C2-DMA was further validated in the context of nucleic acid-lipid particles formulated for delivery of siRNA in vivo, termed KC2-SNALP. These particles comprise a different ratio of lipids than the PFV-prepared nucleic acid-lipid particles described in Example 16.

siRNA were encapsulated in SNALP using a controlled step-wise dilution method process described by Jeffs et al. (Pharm Res 22:362-372 (2005)) The lipid constituents of KC2-SNALP were DLin-KC2-DMA (cationic lipid), dipalmitoylphosphatidylcholine (DPPC; Avanti Polar Lipids, Alabaster, Ala.), synthetic cholesterol (Sigma, St. Louis, Mo.) and PEG-C-DMA used at a molar ratio of 57.1:7.1:34.3:1.4, respectively. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final lipid-to-siRNA ratio in formulations used for in vivo testing was approximately 6.5:1 (wt:wt).

Figure 8:
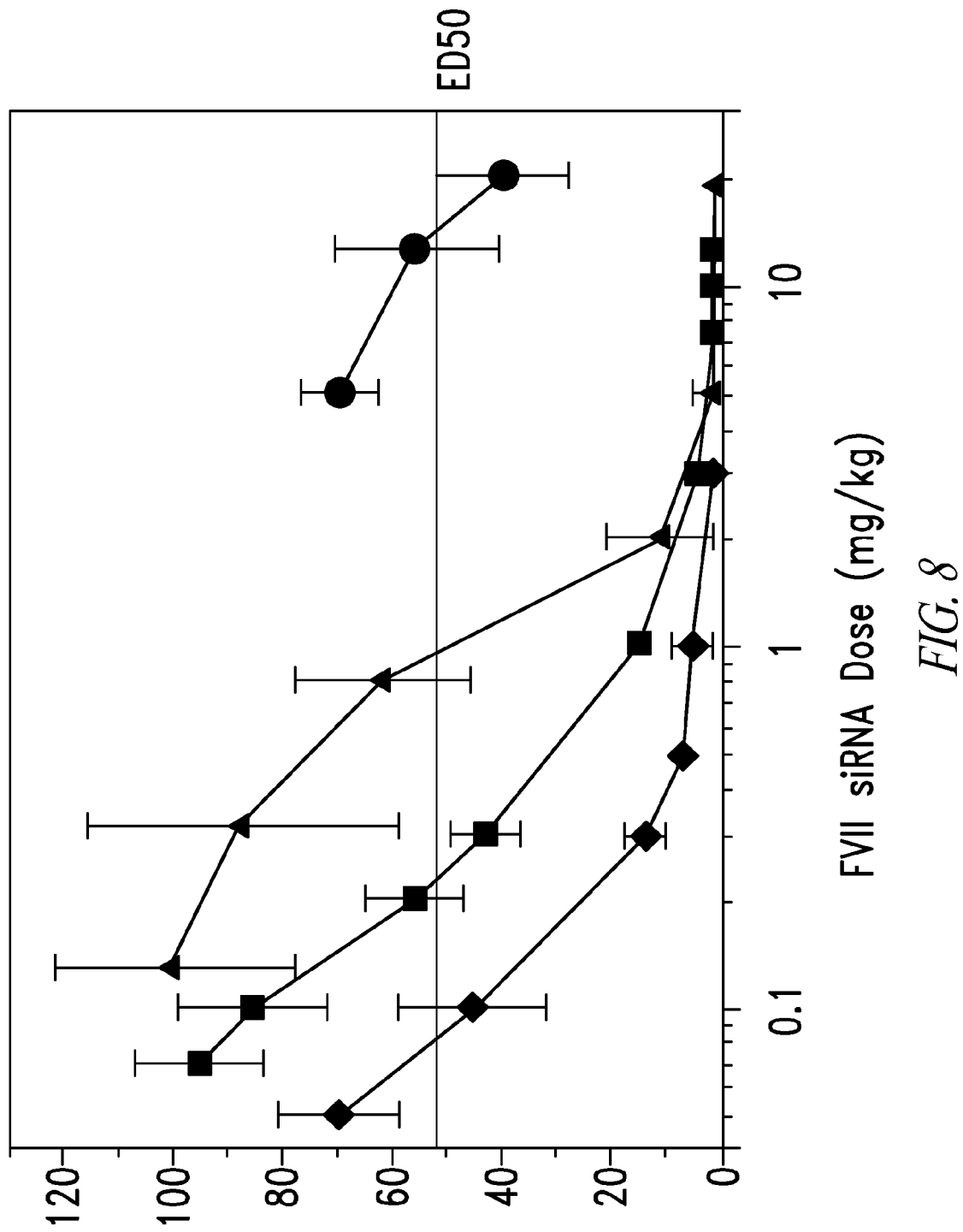
FIG. 8 is a graph showing the amount of residual FVII following administration of various dosages of the nucleic acid-lipid particle formulations comprising the different indicated cationic lipids: DLinDAP (•), DLinDMA (▲), DLin-K-DMA (■), or DLIN-K-C2-DMA (♦).
Figure 9A:
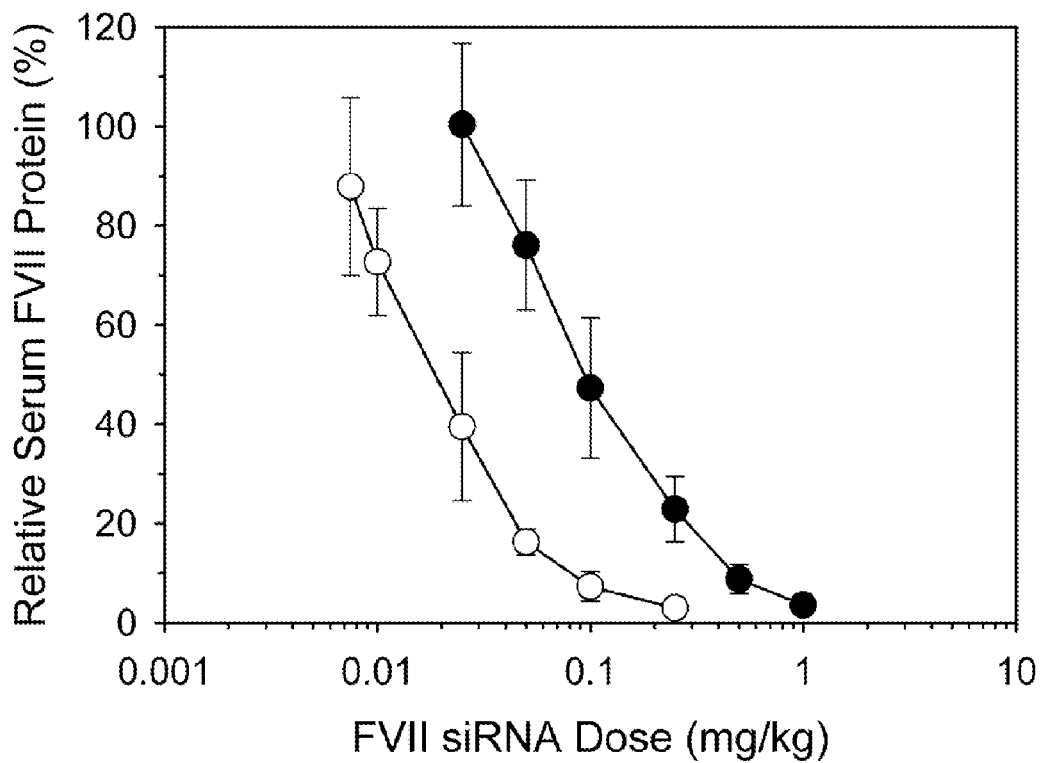
FIGS. 9A-B illustrate the efficacy of KC2-SNALP formulations.
Figure 9B:
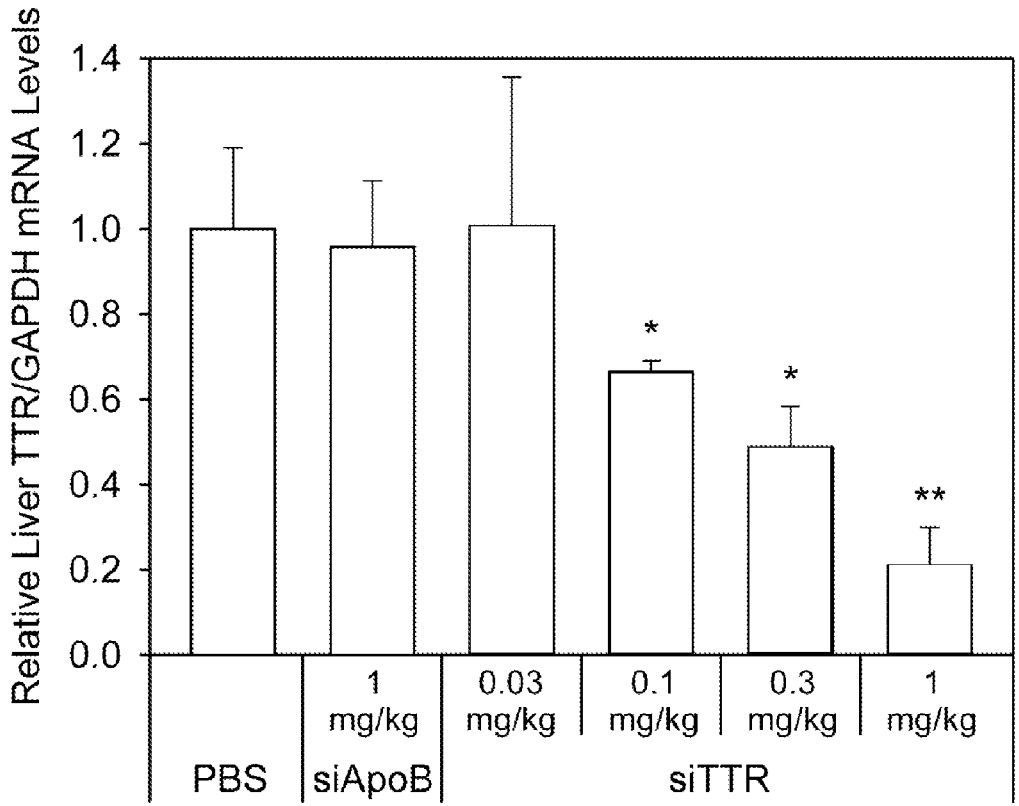

The KC2-SNALP formulation showed a marked improvement in potency in the mouse FVII model as compared to the DLin-K-C2-DMA formulation described in Example 16. The measured $ED_{50}$ decreased from ~0.1 mg/kg for the DLin-K-C2-DMA nucleic acid-lipid formulation described in Example 16 to ~0.02 mg/kg for the KC2-SNALP formulation (FIG. 8A). KC2-SNALP was also found to exhibit similar potency in rats (data not shown).

In addition to efficacy, tolerability is another critical attribute of a suitable nucleic acid-lipid particle delivery system for human use, so the single-dose tolerability of KC2-SNALP was studied in rats. Doses near the efficacious dose level were found to be very well tolerated (data not shown); therefore, single-dose escalation studies were conducted starting at doses ~50-fold higher (1 mg/kg) than the observed $ED_{50}$ of the formulation. To understand formulation toxicity in the absence of any toxicity or pharmacologic effects resulting from target silencing, these experiments were conducted using the non-targeting control siRNA sequence directed against luciferase described in Example 16. Clinical signs

Example 18

In Vivo Efficacy and Tolerability of KC2-SNALP in Primates

Given the promising activity and safety profile observed in rodents in the studies described in Example 17, studies were performed in non-human primates to investigate the translation of DLin-KC2-DMA activity in higher species. For these studies, transthyretin (TTR), a hepatic gene of high therapeutic interest, was targeted.

Cynomolgus monkeys were treated with a single 15 minute intravenous infusion of KC2-SNALP-formulated siTTR at siRNA doses of 0.03, 0.1, 0.3 and 1 mg/kg. Control animals received a single 15 minute intravenous infusion of PBS or KC2-SNALP-formulated ApoB siRNA at a dose of 1 mg/kg. All siRNAs were synthesized by Alnylam and were characterized by electrospray mass spectrometry and anion exchange HPLC. The sequences for the sense and antisense strands of FVII, ApoB, and Control siRNAs have been reported (Akinc, A. et al., Nat. Biotechnol 26:561-569 (2008)). The sequences for the sense and antisense strands of the TTR siRNA were as follows:

```
                                       (SEQ ID NO: 37)
siTTR sense:     5'-GuAAccAAGAGuAuuccAuTT-3';
and (SEQ ID NO: 38)
siTTR antisense: 5'-AUGGAAuACUCUUGGUuACTT-3',
``` with 2'-O-Me modified nucleotides shown in lower case. siRNAs were generated by annealing equimolar amounts of complementary sense and antisense strands.

Tissues were harvested at 48 hours post-administration, and liver mRNA levels of TTR were determined. A clear dose response was obtained with an apparent $ED_{50}$ of ~0.3 mg/kg (FIG. 8B). A toxicological analysis indicated that the treatment was well tolerated at the dose levels tested, with no treatment-related changes in animal appearance or behavior. No dose-dependent, clinically significant alterations in key clinical chemistry or hematological parameters were observed (Table 13).

TABLE 13

Clinical chemistry, and hematology parameters in NHPs

| Treatment | siRNA dose (mg/kg) | ALT (U/L) | AST (U/L) | Total Bilirubin (mg/dL) | BUN (mg/dL) | RBC (×10$^6$/μL) | Hemoglobin (g/dL) | WBC (×10$^3$/μL) | PLT (×10$^3$/μL) |
|---|---|---|---|---|---|---|---|---|---|
| PBS | — | 54 ± 25 | 51 ± 27 | 0.3 ± 0.1 | 27 ± 4 | 4.6 ± 0.5 | 13.8 ± 0.6 | 17.6 ± 3.0 | 515 ± 70 |
| siApoB | 1 | 42 ± 11 | 49 ± 12 | 0.3 ± 0.1 | 23 ± 3 | 6.0 ± 0.2 | 14.2 ± 0.9 | 13.6 ± 3.7 | 508 ± 49 |
| siTTR | 0.03 | 57 ± 11 | 47 ± 12 | 0.1 ± 0 | 15 ± 4 | 4.8 ± 0.4 | 11.5 ± 0.9 | 10.9 ± 2.2 | 495 ± 105 |
| siTTR | 0.1 | 50 ± 22 | 63 ± 47 | 0.13 ± 0.1 | 20 ± 3 | 5.0 ± 0.0 | 11.1 ± 0.4 | 12.9 ± 3.3 | 528 ± 22 |
| siTTR | 0.3 | 67 ± 38 | 66 ± 18 | 0.1 ± 0 | 21 ± 6 | 5.1 ± 0.2 | 11.0 ± 0.5 | 11.1 ± 5.5 | 529 ± 72 |
| siTTR | 1 | 47 ± 5 | 43 ± 7 | 0.13 ± 0.1 | 19 ± 1 | 4.9 ± 0.1 | 10.9 ± 0.4 | 10.7 ± 1.6 | 477 ± 34 |

In summary, a rational design approach was employed for the discovery of novel lipids for use in next-generation LNP systems to deliver RNAi therapeutics. Using this approach, important structure-activity considerations for ionizable cationic lipids were described, and multiple lipids based on the DLinDMA structure were designed and characterized. A SNALP formulation of the best performing lipid (DLin-K-C2-DMA) was well-tolerated in both rodent and non-human primates and exhibited in vivo activity at siRNA doses as low as 0.01 mg/kg in rodents, as well as silencing of a therapeutically significant gene (TTR) in non-human primates. Notably, the TTR silencing achieved in this work ($ED_{50}$~0.3 mg/kg), represents a significant improvement in activity relative to previous reports of LNP-siRNA mediated silencing in non-human primates. The efficacy observed in this study, to our knowledge, represents the highest level of potency observed for an RNAi therapeutic in non-human primates to date, and highlights the considerable progress that has been made in both RNAi and delivery technologies.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. An amino lipid having the structure:
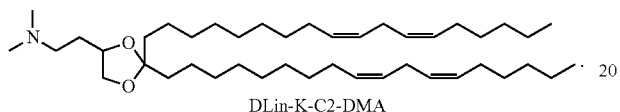
DLin-K-C2-DMA
\* \* \* \* \*